United States Patent
Weinschenk et al.

(10) Patent No.: US 10,561,718 B2
(45) Date of Patent: Feb. 18, 2020

(54) PEPTIDES AND COMBINATION OF PEPTIDES FOR USE IN IMMUNOTHERAPY AGAINST PANCREATIC CANCER AND OTHER CANCERS

(71) Applicant: Immatics biotechnologies GmbH, Tuebingen (DE)

(72) Inventors: Toni Weinschenk, Aichwald (DE); Jens Fritsche, Dusslingen (DE); Harpreet Singh, Munich (DE); Andrea Mahr, Tuebingen (DE); Martina Ott, Tuebingen (DE); Claudia Wagner, Tuebingen (DE); Oliver Schoor, Tuebingen (DE)

(73) Assignee: Immatics Biotechnologies GmbH, Tuebingen (DE)

( * ) Notice: Subject to any disclaimer, the term of this patent is extended or adjusted under 35 U.S.C. 154(b) by 0 days.

(21) Appl. No.: 16/563,096

(22) Filed: Sep. 6, 2019

(65) Prior Publication Data

US 2019/0388530 A1    Dec. 26, 2019

Related U.S. Application Data

(63) Continuation of application No. 16/409,393, filed on May 10, 2019, now Pat. No. 10,449,239, which is a continuation of application No. 15/869,471, filed on Jan. 12, 2018, now Pat. No. 10,357,551, which is a continuation of application No. 15/073,528, filed on Mar. 17, 2016, now Pat. No. 10,076,560.

(60) Provisional application No. 62/134,253, filed on Mar. 17, 2015.

(30) Foreign Application Priority Data

Mar. 17, 2015   (GB) .................................. 1504502.4

(51) Int. Cl.
| | | |
|---|---|---|
| *A61K 35/17* | (2015.01) | |
| *A61K 39/00* | (2006.01) | |
| *C07K 16/18* | (2006.01) | |
| *C07K 14/74* | (2006.01) | |
| *C12N 15/115* | (2010.01) | |
| *C07K 14/47* | (2006.01) | |
| *A61K 38/00* | (2006.01) | |

(52) U.S. Cl.
CPC .. *A61K 39/0011* (2013.01); *A61K 39/001174* (2018.08); *C07K 14/4748* (2013.01); *C07K 14/70539* (2013.01); *C07K 16/18* (2013.01); *C12N 15/115* (2013.01); *A61K 35/17* (2013.01); *A61K 38/00* (2013.01); *A61K 2039/5158* (2013.01); *C07K 2319/00* (2013.01); *C12N 2310/16* (2013.01)

(58) Field of Classification Search
CPC .................................................. A61K 35/17
See application file for complete search history.

(56) References Cited

U.S. PATENT DOCUMENTS

| | | |
|---|---|---|
| 8,080,634 B2 | 12/2011 | Singh et al. |
| 8,669,230 B2 | 3/2014 | Singh et al. |
| 9,101,585 B2 | 8/2015 | Fritsche et al. |
| 9,511,128 B2 | 12/2016 | Singh et al. |
| 9,717,774 B2 | 8/2017 | Fritsche et al. |
| 9,895,415 B2 | 2/2018 | Fritsche et al. |
| 9,950,048 B2 | 4/2018 | Singh et al. |
| 9,993,523 B2 | 6/2018 | Fritsche et al. |
| 10,064,913 B2 | 9/2018 | Weinschenk et al. |
| 2009/0274714 A1 | 11/2009 | Singh et al. |
| 2014/0065620 A1 | 3/2014 | Perez et al. |
| 2017/0304399 A1 | 10/2017 | Fritsche et al. |
| 2018/0125929 A1 | 5/2018 | Fritsche et al. |
| 2019/0076476 A1 | 3/2019 | Weinschenk et al. |

FOREIGN PATENT DOCUMENTS

| | | |
|---|---|---|
| EP | 1760089 A1 | 3/2007 |
| WO | 03/010327 A2 | 2/2003 |
| WO | 2004/030615 A2 | 4/2004 |
| WO | 2004/050858 A2 | 6/2004 |
| WO | 2009/015842 A2 | 2/2009 |
| WO | 2011/113819 A2 | 9/2011 |

OTHER PUBLICATIONS

Pastuszka et al., "Flipping the Switch on Clathrin-Mediated Endocytosis using Thermally Responsive Protein Microdomains." Advanced Functional Materials 24 (2014) 5340-5347.
Khotz et al., "Mapping two functional. domains of clathrin light chains with monoclonal antibodies." The Journal of Cell Biology 104 (1987) 897-903.
Yanagimoto et al., "A phase II study of personalized peptide vaccination combined with gemcitabine for non-resectable pancreatic cancer patients." Oncology Reports 24 (2010) 795-801.

(Continued)

*Primary Examiner* — Stephen L Rawlings
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 14 Drawing Sheets
(11 of 14 Drawing Sheet(s) Filed in Color)
Specification includes a Sequence Listing.

(56) References Cited

OTHER PUBLICATIONS

Rammensee et al., "HLA ligandome tumor antigen discovery for personalized vaccine approach." Expert Review of Vaccines 12 (2013) 1211-1217.
Yutani et al., "A phase II study of a personalized peptide vaccination for chemotherapy-resistant advanced pancreatic cancer patients." Oncology Reports 30 (2013) 1094-1100.
Great Britain Combined Search and Examination Report dated Dec. 15, 2015, issued in Application GB1504502.4.
Weinschenk et al., "Integrated functional genomics approach for the design of patient-individual antitumor vaccines", Cancer Research, Oct. 15, 2002, pp. 5818-5827, vol. 62, No. 20.
International Search Report of International Patent Application No. PCT/EP2016/055817 dated Aug. 30, 2016.

Peptide: FLAQQESEI (A*02) SEQ ID NO: 1

Peptide: SLQEEHVAVA (A*02) SEQ ID NO: 2

Peptide: FLVDGSSAL (A*02) SEQ ID NO: 10

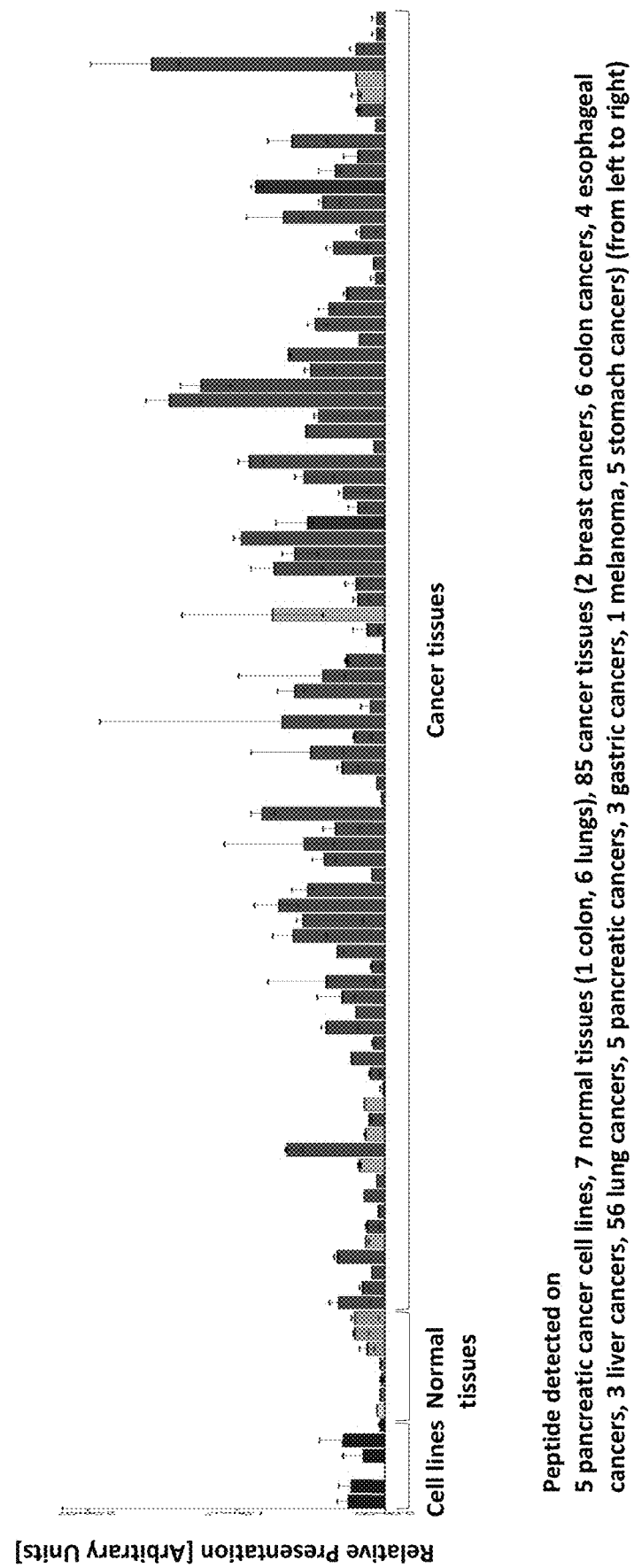

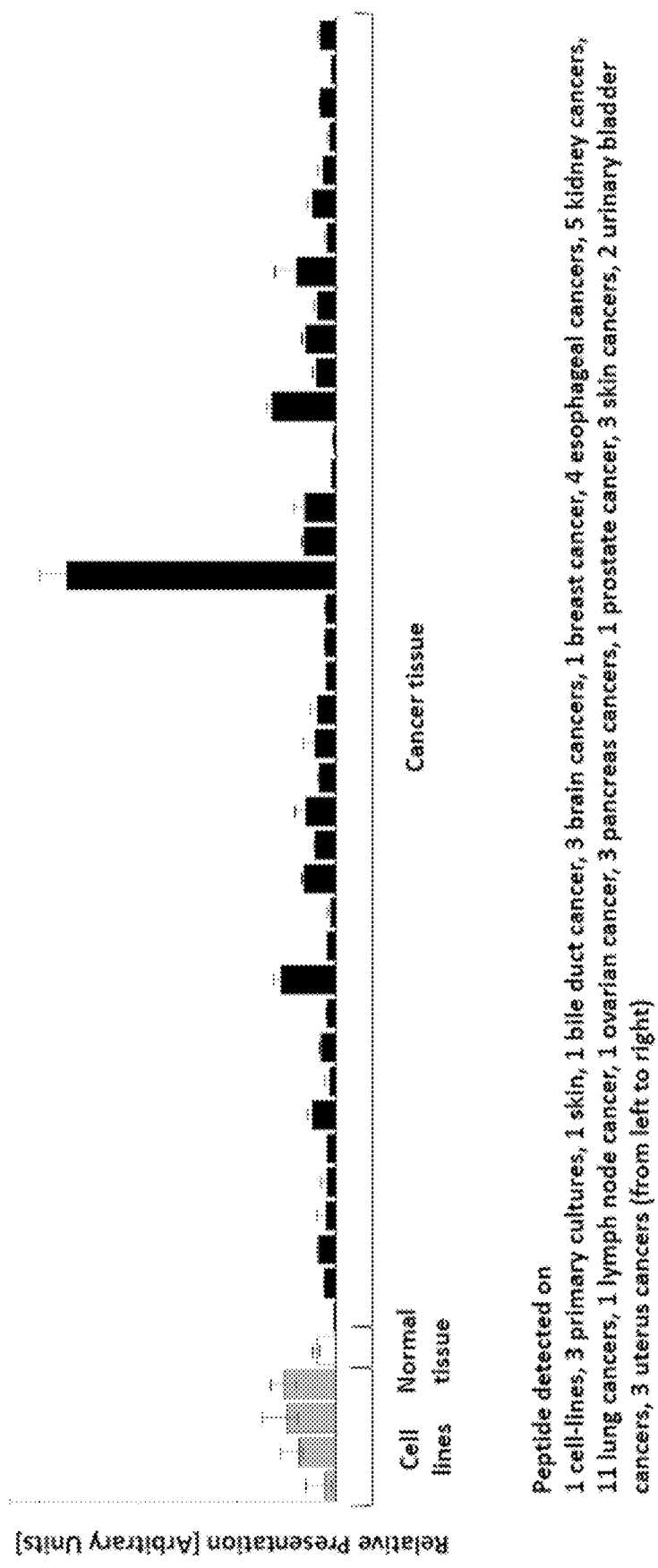

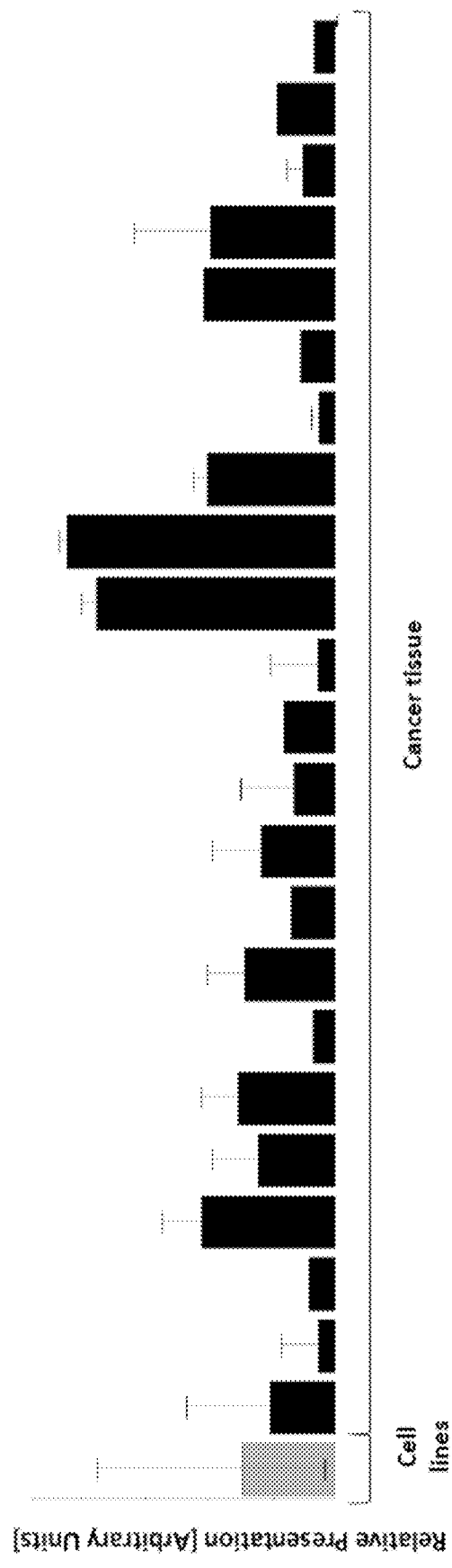

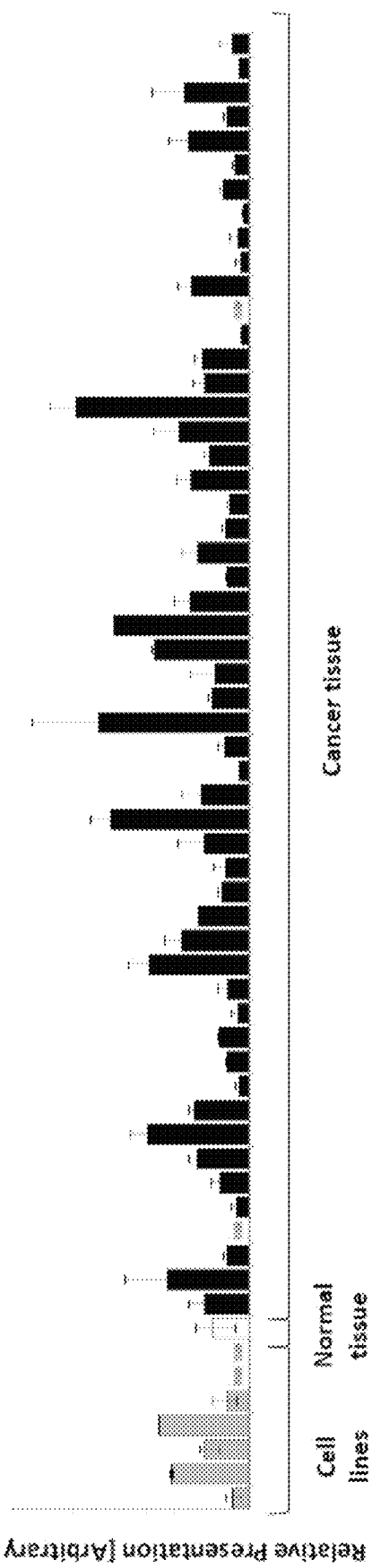

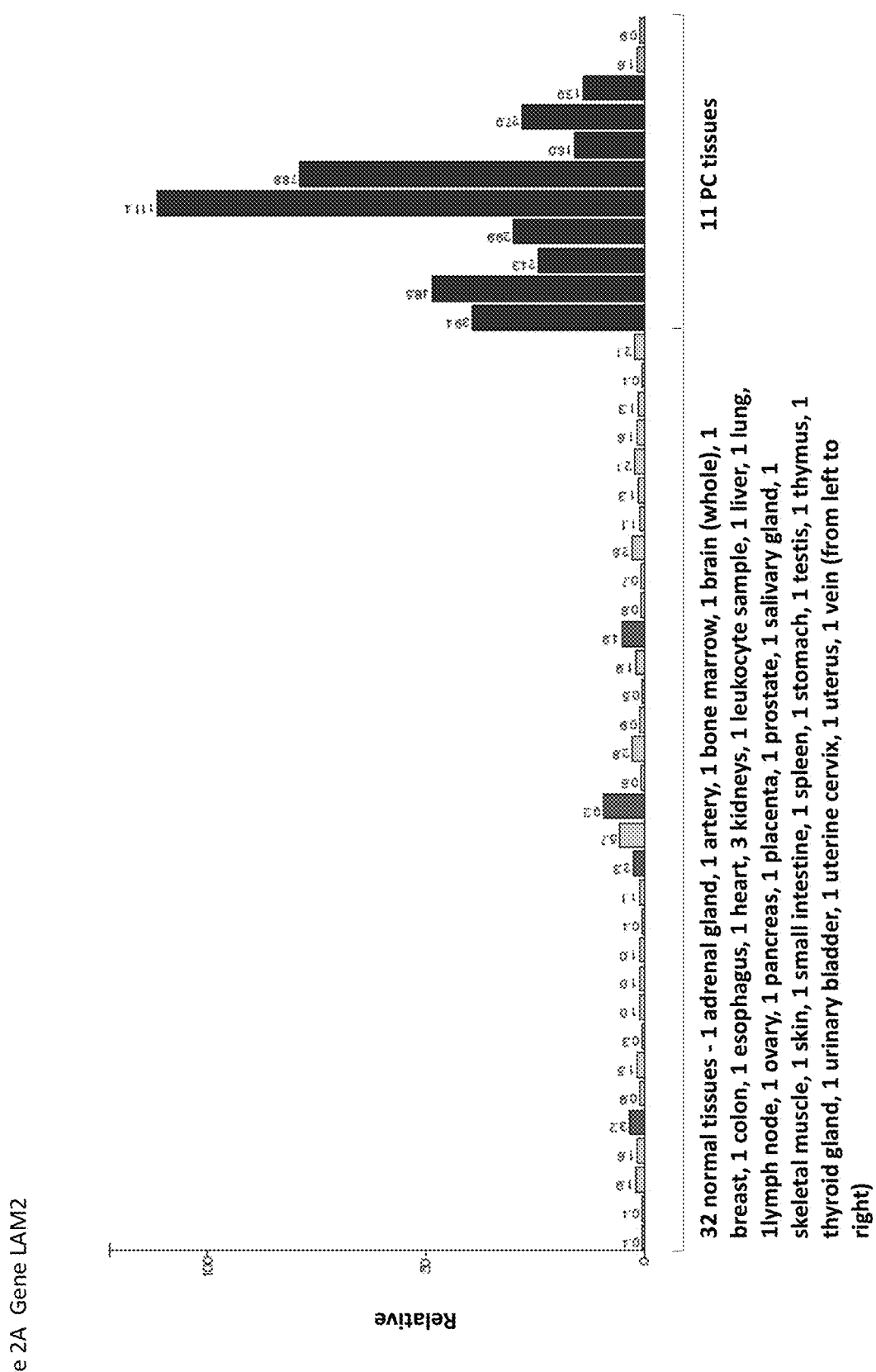
Figure 2A Gene LAM2

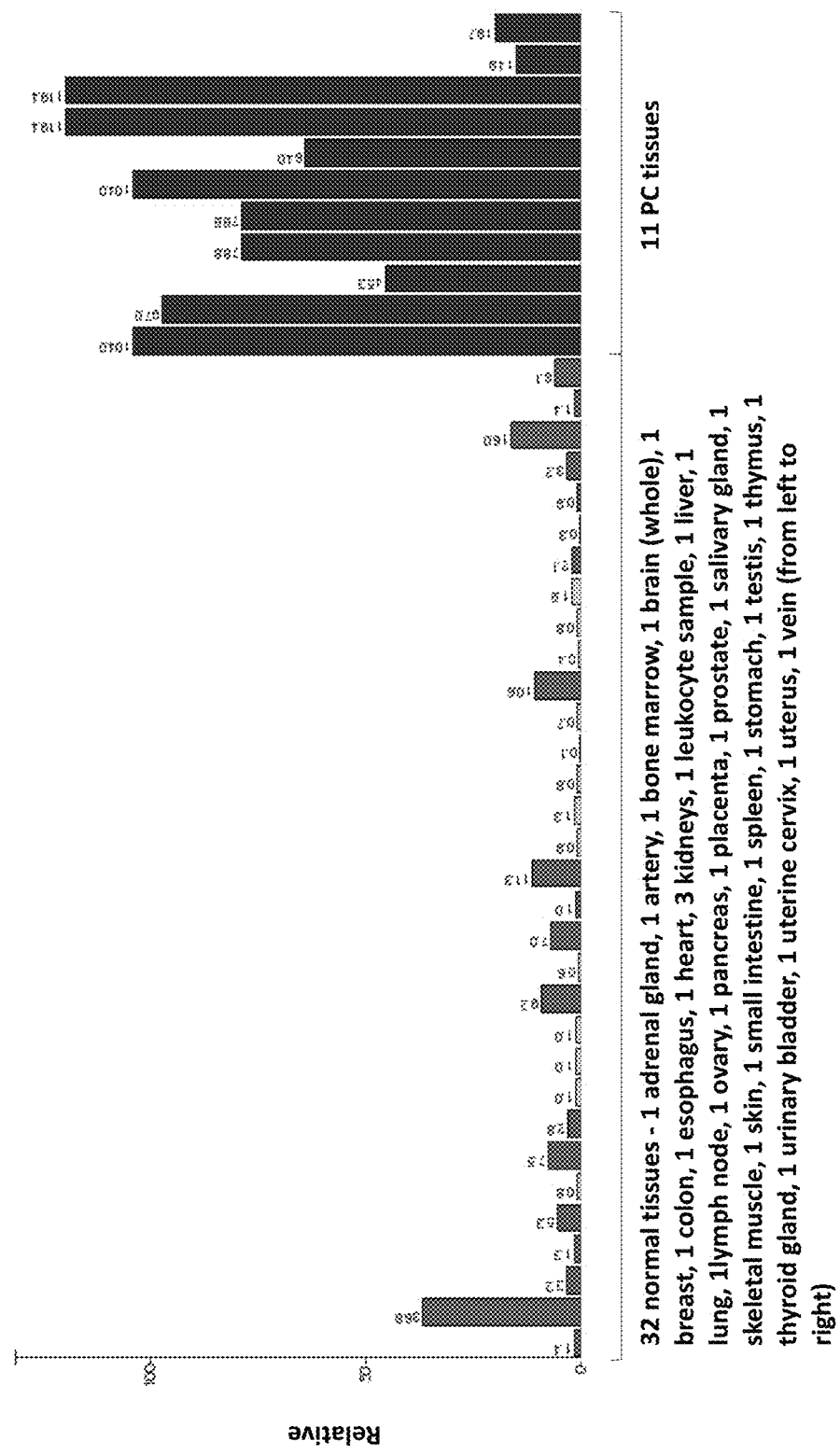
Figure 2B Gene VCAN

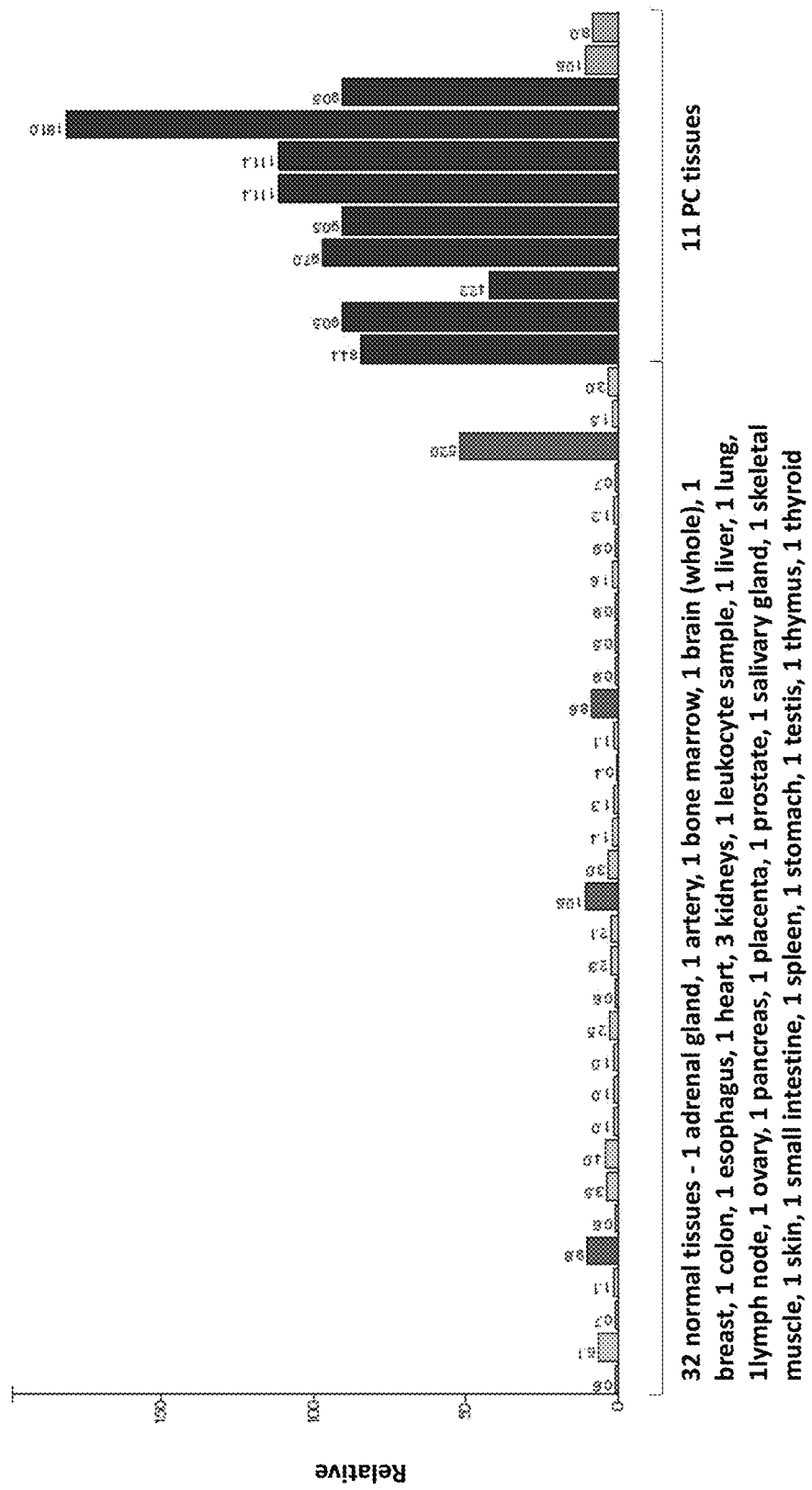
Figure 2C Gene: FAP

PEPTIDES AND COMBINATION OF PEPTIDES FOR USE IN IMMUNOTHERAPY AGAINST PANCREATIC CANCER AND OTHER CANCERS

CROSS REFERENCE TO RELATED APPLICATIONS

This application is a continuation application of U.S. patent application Ser. No. 16/409,393, filed May 10, 2019, now U.S. Pat. No. 10,449,239, which is a continuation application of U.S. patent application Ser. No. 15/869,471, filed Jan. 12, 2018 (now U.S. Pat. No. 10,357,551, issued Jul. 23, 2019), which is a continuation of U.S. patent application Ser. No. 15/073,528 filed Mar. 17, 2016 (now U.S. Pat. No. 10,076,560, issued Sep. 18, 2018), which claims priority to U.S. Application No. 62/134,253, filed Mar. 17, 2015, and GB 1504502.4, filed Mar. 17, 2015, the contents of which are incorporated herein by reference in their entireties.

This application is related to PCT/EP2016/055817, filed Mar. 17, 2016, the content of which is incorporated herein by reference in its entirety.

REFERENCE TO SEQUENCE LISTING SUBMITTED AS A COMPLIANT ASCII TEXT FILE (.txt)

A Sequence Listing is submitted herewith as an ASCII-compliant text file named "Sequence_Listing_2912919-041004_ST25", created on Aug. 22, 2019, and having a size of 14,320 bytes as permitted under 37 C.F.R. § 1.821(c). The material in the aforementioned file is hereby incorporated by reference in its entirety.

BACKGROUND

Field of the Invention

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

Description of Related Art

Pancreatic cancer is one of the most aggressive and deadly cancers in the world. In 2012, it was the 12th most common cancer in men with 178,000 cases and the 11th most common cancer in women with 160,000 cases worldwide. In the same year, 330,000 deaths were reported, making pancreatic cancer the seventh most common cause of death from cancer (World Cancer Report, 2014).

Pancreatic cancer is not one single cancer entity, but several distinct subtypes have to be distinguished. Exocrine tumors account for approximately 95% of all pancreatic cancers and include ductal and acinary adenocarcinomas, intraductal papillary mucinous neoplasms (IPMN), solid pseudopapillary neoplasms, mucinous cystic adenomas and serous cystadenomas. The remaining 5% of all pancreatic cancers belong to the subgroup of pancreatic neuroendocrine tumors (World Cancer Report, 2014).

Infiltrating ductal adenocarcinoma represents the most aggressive form of pancreatic cancer and due to its high frequency (90% of all pancreatic cancers), epidemiologic data mainly reflect this specific subtype (World Cancer Report, 2014).

In 2012, 68% of all new cases occurred in developed countries, with highest incidence rates in central and Eastern Europe, North America, Argentina, Uruguay and Australia. In contrast, most countries in Africa and East Asia display low incidence rates. Globally, incidence rates appear to be rather stable over time in both genders (World Cancer Report, 2014).

Due to a lack of specific symptoms, pancreatic cancer is typically diagnosed at an advanced and often already metastatic stage. The prognosis upon diagnosis is very poor, with a 5 years survival rate of 5% and a mortality-to-incidence ratio of 0.98 (World Cancer Report, 2014).

Several factors have been reported to increase the risk to develop pancreatic cancer, including older age, as most patients are older than 65 years at diagnosis, and race, as in the USA the Black population has an 1.5 fold increased risk compared to the White population. Further risk factors are cigarette smoking, body fatness, diabetes, non-0 AB0 blood type, pancreatitis and a familial history of pancreatic cancer (World Cancer Report, 2014).

Up to 10% of all pancreatic cancer cases are thought to have a familial basis. Germline mutations in the following genes are associated with an increased risk to develop pancreatic cancer: p16/CDKN2A, BRCA2, PALB2, PRSS1, STK11, ATM and DNA mismatch repair genes. Additionally, the sporadic cases of pancreatic cancer are also characterized by mutations in different oncogenes and tumor suppressor genes. The most common mutations in ductal adenocarcinoma occur within the oncogenes KRAS (95%) and AIB1 (up to 60%) and the tumor suppressor genes TP53 (75%), p16/CDKN2A (95%) and SMAD4 (55%) (World Cancer Report, 2014).

Therapeutic options for pancreatic cancer patients are very limited. One major problem for effective treatment is the typically advanced tumor stage at diagnosis. Additionally, pancreatic cancer is rather resistant to chemotherapeutics, which might be caused by the dense and hypovascular desmoplastic tumor stroma.

According to the guidelines released by the German Cancer Society, the German Cancer Aid and the Association of the Scientific Medical Societies in Germany, resection of the tumor is the only available curative treatment option. Resection is recommended if the tumor is restricted to the pancreas or if metastases are limited to adjacent organs. Resection is not recommended if the tumor has spread to distant sites. Resection is followed by adjuvant chemotherapy with gemcitabine or 5-fluorouracil+/−leucovorin for six months (S3-Leitlinie Exokrines Pankreaskarzinom, 2013).

Patients with inoperable tumors in advanced stage can be treated with a combination of chemotherapy with radiation-chemotherapy (S3-Leitlinie Exokrines Pankreaskarzinom, 2013).

The standard regimen for palliative chemotherapy is gemcitabine, either as monotherapy or in combination with the EGF receptor tyrosine kinase inhibitor erlotinib. Alternative options are a combination of 5-fluorouracil, leucovorin, irinotecan and oxaliplatin, also known as FOLFIRINOX protocol or the combination of gemcitabine with nab-paclitaxel, which was shown to have superior effects compared to gemcitabine monotherapy in the MPACT study (Von Hoff et al., 2013; S3-Leitlinie Exokrines Pankreaskarzinom, 2013).

The high mortality-to-incidence ratio reflects the urgent need to implement more effective therapeutic strategies in pancreatic cancer.

Targeted therapies, which have already been shown to be efficient in several other cancer entities, represent an interesting option. Therefore, several studies have been performed to evaluate the benefit of targeted therapies in advanced pancreatic cancers, unfortunately with very limited success (Walker and Ko, 2014). Nevertheless, the genetic diversity of pancreatic cancer might offer the possibility of personalized therapy, as invasive ductal adenocarcinoma with biallelic inactivation of BRCA2 or PALB2 was shown to be more sensitive to poly (ADP-ribose) polymerase inhibitors and mitomycin C treatment (World Cancer Report, 2014).

Targeting the tumor stroma constitutes an alternative approach to develop new treatments for pancreatic cancer. The typically dense and hypovascular stroma might function as barrier for chemotherapeutics and was shown to deliver signals that promote tumor proliferation, invasion and cancer stem cell maintenance. Thus, different preclinical and clinical studies were designed to analyze the effect of stromal depletion and inactivation (Rucki and Zheng, 2014).

Vaccination strategies are investigated as further innovative and promising alternative for the treatment of pancreatic cancer. Peptide-based vaccines targeting KRAS mutations, reactive telomerase, gastrin, survivin, CEA and MUC1 have already been evaluated in clinical trials, partially with promising results. Furthermore, clinical trials for dendritic cell-based vaccines, allogeneic GM-CSF-secreting vaccines and algenpantucel-L in pancreatic cancer patients also revealed beneficial effects of immunotherapy. Additional clinical trials further investigating the efficiency of different vaccination protocols are currently ongoing (Salman et al., 2013).

Considering the severe side-effects and expense associated with treating cancer, there is a need to identify factors that can be used in the treatment of cancer in general and pancreatic cancer in particular. There is also a need to identify factors representing biomarkers for cancer in general and pancreatic cancer in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:
a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.
b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.
c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.
d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor- (-associated) exon in case of proteins with tumor-specific (-associated) isoforms.
e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.
f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY

In a first aspect of the present invention, the present invention relates to a peptide comprising an amino acid sequence selected from the group consisting of SEQ ID NO: 1 to SEQ ID NO: 67 or a variant sequence thereof which is at least 77%, preferably at least 88%, homologous (preferably at least 77% or at least 88% identical) to SEQ ID NO: 1 to SEQ ID NO: 67, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 67 or a variant thereof, which is at least 77%, preferably at least 88%, homologous (preferably at least 77% or at least 88% identical) to SEQ ID NO: 1 to SEQ ID NO: 67, wherein said peptide or variant thereof has an overall length of between 8 and 100, preferably between 8 and 30, and most preferred of between 8 and 14 amino acids.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1I, 2A-2C, and 3A-3D depict embodiments according to the present disclosure.

DETAILED DESCRIPTION OF A PREFERRED EMBODIMENT

Figure 1A:
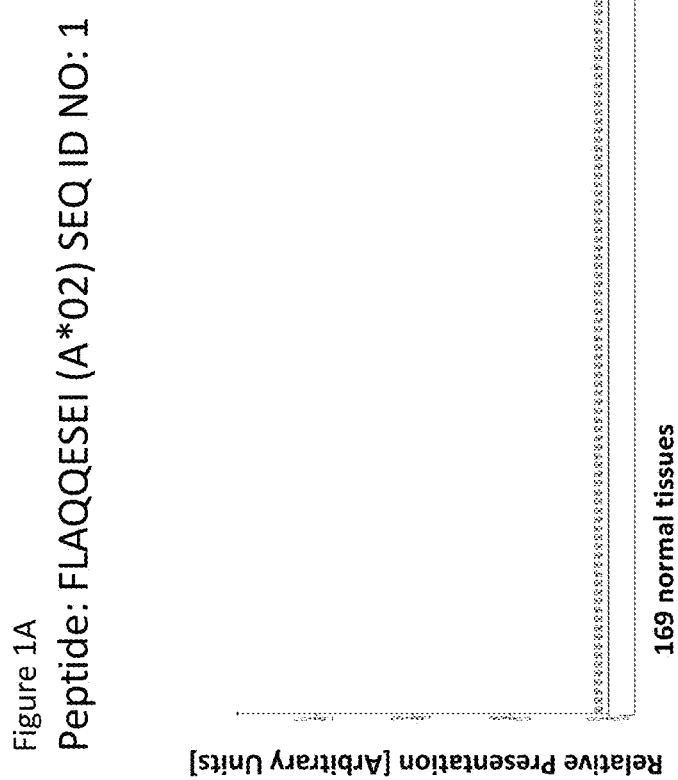

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before. The peptides in Table 3 are additional peptides that may be useful in combination with the other peptides of the invention. The peptides in Table 4 and 4-2 are furthermore useful in the diagnosis and/or treatment of various other malignancies that involve an over-expression or over-presentation of the respective underlying polypeptide.

TABLE 1

Peptides according to the present invention

| SEQ ID No. | Sequence | GeneID(s) | Official Gene Symbol(s) |
|---|---|---|---|
| 1 | FLAQQESEI | 1211, 1212 | CLTA, CLTB |
| 2 | SLQEEHVAVA | 5339 | PLEC |
| 3 | ALLTFMEQV | 165 | AEBP1 |
| 4 | SVDVSPPKV | 113146 | AHNAK2 |
| 5 | LLVDDSFLHTV | 253982 | ASPHD1 |
| 6 | VLISLKQAPLV | 1211 | CLTA |
| 7 | AQQESEIAGI | 1211, 1212 | CLTA, CLTB |
| 8 | IVDDLTINL | 1303 | COL12A1 |
| 9 | FLFDGSANLV | 1293 | COL6A3 |
| 10 | FLVDGSSAL | 1293 | COL6A3 |
| 11 | FLYKIIDEL | 1293 | COL6A3 |
| 12 | FVSEIVDTV | 1293 | COL6A3 |
| 13 | LLAGQTYHV | 1293 | COL6A3 |
| 14 | VLAKPGVISV | 1293 | COL6A3 |
| 15 | SLANNVTSV | 131566 | DCBLD2 |
| 16 | APVNVTTEVKSV | 158078, 1915 | EEF1A1P5, EEF1A1 |
| 17 | FLKSGDAAIV | 158078, 1915 | EEF1A1P5, EEF1A1 |
| 18 | SLLDDELMSL | 26088 | GGA1 |
| 19 | HLAPETDEDDL | 8100 | IFT88 |
| 20 | RLAGDGVGAV | 3855 | KRT7 |
| 21 | HLMDQPLSV | 3918 | LAMC2 |
| 22 | TLDGAAVNQV | 3918 | LAMC2 |
| 23 | SLSAFTLFL | 4060 | LUM |
| 24 | GLLEELVTV | 642475 | MROH6 |
| 25 | SLKEEVGEEAI | 4627 | MYH9 |
| 26 | SLKEEVGEEAIV | 4627 | MYH9 |
| 27 | YLQGQRLDNV | 6447 | SCG5 |
| 28 | YLQGQRLDNVV | 6447 | SCG5 |
| 29 | FLQEYLDAI | 6317, 6318 | SERPINB3, SERPINB4 |
| 30 | VVDEGPTGV | 9123 | SLC16A3 |
| 31 | SLAAAAGKQEL | 6750 | SST |
| 32 | SLAAAAGKQELA | 6750 | SST |
| 33 | SLDSRLELA | 81628 | T5C22D4 |
| 34 | MLMPVHFLL | 114131 | UCN3 |
| 35 | VMDSGDGVTHTV | 100996820, 344227, 345651, 440915, 445582, 60, 641455, 653269, 653781, 71, 728378 | ACTBL2, POTEKP, POTEE, ACTB, POTEM, POTEI, POTEJ, ACTG1, POTEF |
| 36 | KQEYDESGPSIVH | 100996820, 344227, 440915, 445582, 60, 641455, 653269, 653781, 71, 728378 | POTEKP, POTEE, ACTB, POTEM, POTEI, POTEJ, ACTG1, POTEF |
| 37 | GLLKKINSV | 55107 | ANO1 |
| 38 | NLVEKTPALV | 10632, 267020 | ATP5L, ATP5L2 |
| 39 | TLLSNLEEA | 1191 | CLU |
| 40 | FILDSAETTTL | 1293 | COL6A3 |
| 41 | FLLDGSEGV | 1293 | COL6A3 |
| 42 | KLVDKSTEL | 1293 | COL6A3 |
| 43 | RLDQRVPQI | 1293 | COL6A3 |
| 44 | VLLDKIKNLQV | 1293 | COL6A3 |
| 45 | VADKIHSV | 11072 | DUSP14 |
| 46 | TFAPVNVTTEVKSV | 158078, 1915 | EEF1A1P5, EEF1A1 |
| 47 | KMDASLGNLFA | 10447, 51384 | FAM3C, WNT16 |
| 48 | ALTQTGGPHV | 2316 | FLNA |
| 49 | NLKGTFATL | 100187828, 3043, 3045 | HBB, HBD |
| 50 | ALAAILTRL | 80201 | HKDC1 |
| 51 | ALMLQGVDL | 3329 | HSPD1 |
| 52 | RMVEEIGVEL | 10525 | HYOU1 |
| 53 | SSFGGLGGGSV | 3880 | KRT19 |
| 54 | VLLSEIEVA | 4134 | MAP4 |
| 55 | YLDAMMNEA | 103910, 10627 | MYL12B, MYL12A |
| 56 | GLLDYATGAIGSV | 117583 | PARD3B |
| 57 | FLGKVVIDV | 100271927, 10156 | RASA4B, RASA4 |

TABLE 1-continued

Peptides according to the present invention

| SEQ ID No. | Sequence | GeneID (s) | Official Gene Symbol (s) |
|---|---|---|---|
| 58 | GLAAFKAFL | 5999 | RGS4 |
| 59 | KLFNLSKEDDV | 6194 | RPS6 |
| 60 | YLEEDVYQL | 23255 | SOGA2 |
| 61 | ALEKDYEEVGV | 10376, 113457, 7278, 7846 | TUBA1B, TUBA3D, TUBA3C, TUBA1A |
| 62 | ALEKDYEEV | 10376, 113457, 51807, 7277, 7278, 7846, 84790 | TUBA1B, TUBA3D, TUBA8, TUBA4A, TUBA3C, TUBA1A, TUBA1C |
| 63 | FAGDDAPR | 100996820, 344227, 445582, 58, 59, 60, 653269, 653781, 70, 71, 72, 728378 | POTEE, ACTA1, ACTA2, ACTB, POTEI, POTEJ, ACTC1, ACTG1, ACTG2, POTEF |
| 64 | FLVSNMLLAEA | 113791 | PIK3IP1 |

TABLE 2

Additional peptides according to the present invention with no prior known cancer association

| SEQ ID No. | Sequence | GeneID (s) | Official Gene Symbol (s) |
|---|---|---|---|
| 65 | YLYDSETKNA | 4316 | MMP7 |
| 66 | ALLSGLREA | 23028 | KDM1A |
| 67 | KMFFLIDKV | 4599 | MX1 |

TABLE 3

Peptides useful for e.g. personalized cancer therapies

| SEQ ID No. | Sequence | GeneID (s) | Official Gene Symbol (s) |
|---|---|---|---|
| 68 | KLLTEVHAA | 101 | ADAM8 |
| 69 | VMAPFTMTI | 338 | APOB |
| 70 | FLVDGSWSV | 1303 | COL12A1 |
| 71 | FLLDGSANV | 1293 | COL6A3 |
| 72 | YVYQNNIYL | 2191 | FAP |
| 73 | TLVAIVVGV | 60681 | FKBP10 |
| 74 | KIQEILTQV | 10643 | IGF2BP3 |
| 75 | RLDDLKMTV | 3918 | LAMC2 |
| 76 | RLLDSVSRL | 3918 | LAMC2 |
| 77 | GLTDNIHLV | 25878 | MXRA5 |
| 78 | TLSSIKVEV | 25878 | MXRA5 |
| 79 | VLAPRVLRA | 5954 | RCN1 |
| 80 | TLYPHTSQV | 1462 | VCAN |
| 81 | AMSSKFFLV | 7474 | WNT5A |
| 82 | SISDVIAQV | 56172 | ANKH |
| 83 | FLIDSSEGV | 1293 | COL6A3 |
| 84 | NLLDLDYEL | 1293 | COL6A3 |
| 85 | TVAEVIQSV | 55083 | KIF26B |
| 86 | SLLAQNTSWLL | 7070 | THY1 |
| 87 | LLLGSPAAA | 23544 | SEZ6L |

The present invention furthermore generally relates to the peptides according to the present invention for use in the treatment of proliferative diseases, such as, for example, lung cancer, kidney cancer, brain cancer, colon or rectal cancer, esophageal cancer, breast cancer, ovarian cancer, stomach cancer, liver cancer, prostate cancer, melanoma and leukemias.

Particularly preferred are the peptides—alone or in combination—according to the present invention selected from the group consisting of SEQ ID NO: 1 to SEQ ID NO: 67. More preferred are the peptides—alone or in combination—selected from the group consisting of SEQ ID NO: 1 to SEQ ID NO: 34 (see Table 1), and their uses in the immunotherapy of pancreatic cancer, lung cancer, kidney cancer, brain cancer, colon or rectal cancer, esophageal cancer, breast cancer, ovarian cancer, stomach cancer, liver cancer, prostate cancer, melanoma and leukemias, and preferably pancreatic cancer. As shown in the following Table 4 and 4-2, many of the peptides according to the present invention are also found on other tumor types and can, thus, also be used in the immunotherapy of other indications. Also refer to FIGS. 1A-1I and Example 1.

TABLE 4

Peptides according to the present invention and their specific uses in other proliferative diseases, especially in other cancerous diseases. The table shows for selected peptides on which additional tumor types they were found and over-presented on at least 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
|---|---|---|
| 3 | ALLTFMEQV | Lung, Kidney, Brain, Colon, Rectum, Esophagus |
| 4 | SVDVSPPKV | Lung, Kidney, Melanoma |
| 5 | LLVDDSFLHTV | Kidney, Brain, Liver, Melanoma, Ovary |
| 8 | IVDDLTINL | Esophagus |
| 9 | FLFDGSANLV | Lung, Colon, Rectum, Breast, Esophagus |
| 10 | FLVDGSSAL | Lung, Stomach, Breast |
| 11 | FLYKIIDEL | Lung, Colon, Rectum, Breast |
| 12 | FVSEIVDTV | Lung, Breast, Esophagus |
| 14 | VLAKPGVISV | Lung |
| 15 | SLANNVTSV | Lung, Kidney, Brain, Stomach, Melanoma, Ovary, Esophagus |
| 16 | APVNVTTEVKSV | Leukocytes |
| 21 | HLMDQPLSV | Lung |
| 23 | SLSAFTLFL | Lung, Prostate |
| 24 | GLLEELVTV | Lung, Stomach, Ovary |
| 30 | VVDEGPTGV | Lung, Kidney, Brain, Stomach, Liver, Leukocytes, Breast, Ovary |
| 34 | MLMPVHFLL | Stomach |
| 36 | KQEYDESGPSIVH | Lung, Brain |
| 39 | TLLSNLEEA | Brain, Prostate |
| 40 | FILDSAETTTL | Lung |
| 41 | FLLDGSEGV | Lung, Breast, Ovary, Esophagus |
| 42 | KLVDKSTEL | Lung, Colon, Rectum, Esophagus |
| 43 | RLDQRVPQI | Lung, Colon, Rectum, Breast, Esophagus |
| 44 | VLLDKIKNLQV | Lung, Stomach, Colon, Rectum, Liver, Breast, Melanoma |
| 45 | VADKIHSV | Kidney, Stomach |
| 47 | KMDASLGNLFA | Brain |
| 50 | ALAAILTRL | Kidney, Stomach, Colon, Rectum |
| 51 | ALMLQGVDL | Esophagus |
| 53 | SSFGGLGGGSV | Lung |
| 55 | YLDAMMNEA | Brain, Colon, Rectum, Liver, Ovary |
| 58 | GLAAFKAFL | Lung, Kidney, Liver |
| 60 | YLEEDVYQL | Lung, Kidney, Colon, Rectum, Breast |
| 64 | FLVSNMLLAEA | Prostate |
| 65 | YLYDSETKNA | Kidney, Colon, Rectum, Liver, Ovary, Esophagus |
| 66 | ALLSGLREA | Kidney, Leukocytes, Melanoma |
| 67 | KMFFLIDKV | Brain, Liver |
| 68 | KLLTEVHAA | Lung, Kidney, Stomach, Colon, Rectum, Liver, Breast, Ovary |
| 69 | VMAPFTMTI | Lung, Liver, Prostate, Ovary, Esophagus |
| 70 | FLVDGSWSV | Lung, Stomach, Colon, Rectum, Ovary, Esophagus |
| 71 | FLLDGSANV | Lung, Stomach, Colon, Rectum, Liver, Breast, Ovary, Esophagus |

TABLE 4-continued

Peptides according to the present invention and their specific uses in other proliferative diseases, especially in other cancerous diseases. The table shows for selected peptides on which additional tumor types they were found and over-presented on at least 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs/diseases |
|---|---|---|
| 72 | YVYQNNIYL | Lung, Stomach, Colon, Rectum, Liver, Breast, Melanoma, Ovary, Esophagus |
| 73 | TLVAIVVGV | Lung, Kidney, Brain, Stomach, Colon, Rectum, Liver, Prostate, Breast, Ovary, Esophagus |
| 74 | KIQEILTQV | Lung, Kidney, Brain, Stomach, Colon, Rectum, Liver, Leukocytes, Ovary, Esophagus |
| 75 | RLDDLKMTV | Lung, Kidney, Colon, Rectum, Ovary, Esophagus |
| 76 | RLLDSVSRL | Lung, Kidney, Colon, Rectum, Liver, Ovary |
| 77 | GLTDNIHLV | Lung, Kidney, Colon, Rectum, Ovary, Esophagus |
| 78 | TLSSIKVEV | Lung, Kidney, Stomach, Colon, Rectum, Prostate, Breast, Melanoma |
| 79 | VLAPRVLRA | Lung, Kidney, Brain, Colon, Rectum, Liver |
| 81 | AMSSKFFLV | Lung, Brain, Stomach, Colon, Rectum, Liver, Prostate, Esophagus |
| 82 | SISDVIAQV | Lung, Brain, Colon, Rectum, Liver, Prostate |
| 83 | FLIDSSEGV | Lung, Colon, Rectum, Breast, Ovary, Esophagus |
| 84 | NLLDLDYEL | Lung, Stomach, Colon, Rectum, Breast, Ovary, Esophagus |
| 85 | TVAEVIQSV | Lung, Esophagus |
| 86 | SLLAQNTSWLL | Lung, Kidney, Brain, Stomach, Colon, Rectum, Liver, Melanoma |
| 87 | LLLGSPAAA | Brain |

TABLE 4-2

Peptides according to the present invention and their specific uses in other proliferative diseases, especially in other cancerous diseases (amendment of Table 4). The table shows, like Table 4, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, cartilage, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, and urinary bladder.

| SEQ ID No. | Sequence | Additional Entities |
|---|---|---|
| 3 | ALLTFMEQV | SCLC, BRCA, Melanoma, Urinary bladder cancer, Gallbladder Cancer, Bile Duct Cancer |
| 4 | SVDVSPPKV | Melanoma, Esophageal Cancer |
| 5 | LLVDDSFLHTV | SCLC, BRCA, Melanoma, Esophageal Cancer, Uterine Cancer, Gallbladder Cancer, Bile Duct Cancer |
| 6 | VLISLKQAPLV | BRCA, Urinary bladder cancer, Gallbladder Cancer, Bile Duct Cancer |
| 8 | IVDDLTINL | NSCLC, GC, Melanoma, Uterine Cancer, Gallbladder Cancer, Bile Duct Cancer, NHL |
| 9 | FLFDGSANLV | SCLC, Melanoma, OC, Urinary bladder cancer, Gallbladder Cancer, Bile Duct Cancer |
| 10 | FLVDGSSAL | SCLC, CRC, Melanoma, Esophageal Cancer, Urinary bladder cancer, Gallbladder Cancer, Bile Duct Cancer |
| 11 | FLYKIIDEL | SCLC, Melanoma, Urinary bladder cancer, Gallbladder Cancer, Bile Duct Cancer |
| 12 | FVSEIVDTV | SCLC, GC, CRC, Urinary bladder cancer, Gallbladder Cancer, Bile Duct Cancer |
| 13 | LLAGQTYHV | NSCLC, BRCA, OC, Esophageal Cancer, Urinary bladder cancer, Gallbladder Cancer, Bile Duct Cancer |
| 14 | VLAKPGVISV | BRCA, Gallbladder Cancer, Bile Duct Cancer |
| 15 | SLANNVTSV | Urinary bladder cancer, Uterine Cancer, Gallbladder Cancer, Bile Duct Cancer |
| 16 | APVNVTTEVKSV | AML |
| 19 | HLAPETDEDDL | Gallbladder Cancer, Bile Duct Cancer |
| 20 | RLAGDGVGAV | Urinary bladder cancer |
| 21 | HLMDQPLSV | OC, Esophageal Cancer, Uterine Cancer, Gallbladder Cancer, Bile Duct Cancer |
| 22 | TLDGAAVNQV | Esophageal Cancer, Uterine Cancer, Gallbladder Cancer, Bile Duct Cancer |

TABLE 4-2-continued

Peptides according to the present invention and their specific uses in other proliferative diseases, especially in other cancerous diseases (amendment of Table 4). The table shows, like Table 4, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, cartilage, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, and urinary bladder.

| SEQ ID No. | Sequence | Additional Entities |
|---|---|---|
| 23 | SLSAFTLFL | SCLC, BRCA, Melanoma, OC, Esophageal Cancer, Urinary bladder cancer, Gallbladder Cancer, Bile Duct Cancer, NHL |
| 24 | GLLEELVTV | SCLC, CRC, BRCA, Uterine Cancer, Gallbladder Cancer, Bile Duct Cancer |
| 29 | FLQEYLDAI | Urinary bladder cancer |
| 30 | VVDEGPTGV | SCLC, CRC, Melanoma, Urinary bladder cancer, Uterine Cancer, Gallbladder Cancer, Bile Duct Cancer, NHL |
| 34 | MLMPVHFLL | BRCA |
| 37 | GLLKKINSV | BRCA, Esophageal Cancer, Urinary bladder cancer, Gallbladder Cancer, Bile Duct Cancer, OC |
| 38 | NLVEKTPALV | AML |
| 39 | TLLSNLEEA | Urinary bladder cancer, Uterine Cancer, NHL |
| 40 | FILDSAETTTL | SCLC, BRCA, OC, Esophageal Cancer |
| 41 | FLLDGSEGV | SCLC, Melanoma, Urinary bladder cancer, Gallbladder Cancer Bile Duct Cancer |
| 42 | KLVDKSTEL | SCLC, BRCA, Melanoma, Gallbladder Cancer, Bile Duct Cancer |
| 43 | RLDQRVPQI | SCLC, Gallbladder Cancer, Bile Duct Cancer |
| 44 | VLLDKIKNLQV | SCLC, OC, Esophageal Cancer, Urinary bladder cancer, Gallbladder Cancer, Bile Duct Cancer, NHL |
| 45 | VADKIHSV | BRCA, Melanoma, Esophageal Cancer, Urinary bladder cancer |
| 46 | TFAPVNVTTEVKSV | Gallbladder Cancer, Bile Duct Cancer |
| 47 | KMDASLGNLFA | Esophageal Cancer, Urinary bladder cancer |
| 50 | ALAAILTRL | Uterine Cancer, Gallbladder Cancer, Bile Duct Cancer |
| 51 | ALMLQGVDL | BRCA |
| 53 | SSFGGLGGGSV | BRCA |
| 54 | VLLSEIEVA | Melanoma, Uterine Cancer |
| 55 | YLDAMMNEA | PrC, Melanoma, Urinary bladder cancer, Gallbladder Cancer, Bile Duct Cancer |
| 58 | GLAAFKAFL | SCLC, BRCA, Melanoma, OC, Esophageal Cancer, Uterine Cancer, Gallbladder Cancer, Bile Duct Cancer, NHL, OC |
| 60 | YLEEDVYQL | Melanoma, Esophageal Cancer, Urinary bladder cancer, Uterine Cancer, Gallbladder Cancer, Bile Duct Cancer, NHL |
| 64 | FLVSNMLLAEA | Urinary bladder cancer |
| 65 | YLYDSETKNA | SCLC, BRCA, Uterine Cancer, Gallbladder Cancer, Bile Duct Cancer |
| 66 | ALLSGLREA | GC, BRCA |
| 67 | KMFFLIDKV | BRCA, Melanoma, OC, Urinary bladder cancer, Uterine Cancer, Gallbladder Cancer, Bile Duct Cancer, NHL, OC |

NSCLC = non-small cell lung cancer, SCLC = small cell lung cancer, RCC= kidney cancer, CRC = colon or rectum cancer, GC = stomach cancer, HCC = liver cancer, PC= pancreatic cancer, PrC = prostate cancer, BRCA = breast cancer, MCC = Merkel cell carcinoma, OC = ovarian cancer, NHL = non-Hodgkin lymphoma, AML = acute myeloid leukemia, CLL = chronic lymphocytic leukemia.

Thus, another aspect of the present invention relates to the use of at least one peptide according to the present invention selected from SEQ ID No. 3, 4, 9, 10, 11, 12, 14, 15, 21, 23, 24, 30, 36, 40, 41, 42, 43, 44, 50, 53, 58, 60, 68, 69, 70, 71, 72, 73, 74, 75, 76, 77, 78, 79, 81, 82, 83, 84 85, and 86 for the—in one preferred embodiment combined—treatment of lung cancer.

Thus, another aspect of the present invention relates to the use of at least one peptide according to the present invention selected from SEQ ID No. 3, 4, 5, 15, 30, 45, 50, 58, 60, 65, 66, 68, 73, 74, 75, 76, 77, 78, 79, and 86 for the—in one preferred embodiment combined—treatment of kidney cancer.

Thus, another aspect of the present invention relates to the use of at least one peptide according to the present invention selected from SEQ ID No. 3, 5, 15, 30, 36, 39, 47, 55, 67, 73, 74, 79, 81, 82, 86, and 87 for the—in one preferred embodiment combined—treatment of brain cancer.

Thus, another aspect of the present invention relates to the use of at least one peptide according to the present invention selected from SEQ ID No. 3, 9, 11, 42, 43, 44, 50, 55, 60, 65, 68, 70, 71, 72, 73, 74, 75, 76, 77, 78, 79, 81, 82, 83, 84, and 86 for the—in one preferred embodiment combined—treatment of colon cancer.

Thus, another aspect of the present invention relates to the use of at least one peptide according to the present invention selected from SEQ ID No. 3, 9, 11, 42, 43, 44, 50, 55, 60, 65, 68, 70, 71, 72, 73 74, 75, 76, 77, 78, 79, 81, 82, 83, 84, and 86 for the—in one preferred embodiment combined—treatment of rectal cancer.

Thus, another aspect of the present invention relates to the use of at least one peptide according to the present invention selected from SEQ ID No. 3, 8, 9, 12, 15, 41, 42, 43, 51, 65, 69, 70, 71, 72 73, 74, 75, 77, 81, 83, 84, and 85 for the—in one preferred embodiment combined—treatment of esophageal cancer.

Thus, another aspect of the present invention relates to the use of at least one peptide according to the present invention selected from SEQ ID No. 4, 5, 15, 44, 66, 72, 78, and 86 for the—in one preferred embodiment combined—treatment of melanoma.

Thus, another aspect of the present invention relates to the use of at least one peptide according to the present invention selected from SEQ ID No. 5, 15, 24, 30, 41, 55, 65, 68, 69, 70, 71, 72, 73, 74, 75, 76, 77, 83, and 84 for the—in one preferred embodiment combined—treatment of ovarian cancer.

Thus, another aspect of the present invention relates to the use of at least one peptide according to the present invention selected from SEQ ID No. 9, 10, 11, 12, 41, 43, 60, 71, 72, 73, 78, 83, and 84 for the—in one preferred embodiment combined—treatment of breast cancer.

Thus, another aspect of the present invention relates to the use of at least one peptide according to the present invention selected from SEQ ID No. 5 30, 44, 55, 58, 65, 67, 68, 69, 71, 72, 73, 74, 76, 79, 81, 82, 85, and 86 for the—in one preferred embodiment combined—treatment of liver cancer.

Thus, another aspect of the present invention relates to the use of at least one peptide according to the present invention selected from SEQ ID No. 10, 15, 24, 30, 34, 44, 45, 50, 68, 70, 71, 72, 73, 74, 78, 81, 84, and 86 for the—in one preferred embodiment combined—treatment of stomach cancer.

Thus, another aspect of the present invention relates to the use of at least one peptide according to the present invention selected from SEQ ID No. 23, 39, 64, 69, 73, 78, 81, and 82 for the—in one preferred embodiment combined—treatment of prostate cancer.

Thus, another aspect of the present invention relates to the use of at least one peptide according to the present invention selected from SEQ ID No. 16, 30, 66, and 74 for the—in one preferred embodiment combined—treatment of leukocytic cancer.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 67.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention.

The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 67, preferably containing SEQ ID No. 1 to SEQ ID No. 34, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is for a cellular therapy, a vaccine, a protein or based on a soluble TCR or antibody.

The present invention further relates to a use according to the present invention, wherein said cancer cells are pancreatic cancer, lung cancer, kidney cancer, brain cancer, colon or rectal cancer, esophageal cancer, breast cancer, ovarian cancer, stomach cancer, liver cancer, prostate cancer, melanoma and leukemias, and preferably pancreatic cancer cells.

The present invention further relates to biomarkers based on the peptides according to the present invention, herein called "targets" that can be used in the diagnosis of cancer, preferably pancreatic cancer. The marker can be over-presentation of the peptide (s) themselves, or over-expression of the corresponding gene (s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

Both therapeutic and diagnostic uses against additional cancerous diseases are disclosed in the following more detailed description of the underlying expression products (polypeptides) of the peptides according to the invention.

The gene for ACAT2 encodes acetyl-CoA acetyltransferase 2, a thiolase involved in lipid metabolism. ACAT2 expression is up-regulated in hepatocellular carcinoma (Song et al., 2006). ACAT2 expression is associated with radioresistance in pancreatic cancer cell lines (Souchek et al., 2014).

The gene for ACTA1 encodes the skeletal muscle alpha actin, a member of the actin family of proteins, which are highly conserved proteins that play a role in cell motility, structure and integrity. ACTA1, a classical myoepithelial marker, was shown to be highly expressed in cancer-associated fibroblasts in urinary bladder cancer, oral squamous cell carcinoma, invasive breast cancer, gastric cancer, cholangiocarcinoma and metastatic liver carcinoma and to contribute to epithelial-mesenchymal transition, tumor stroma formation and fibrosis (Schulte et al., 2012; Franz et al., 2010; Kuroda et al., 2005; Nakayama et al., 2002; Terada et al., 1996).

The gene for ACTA2 encodes the smooth muscle alpha actin, a member of the actin family of proteins, which are highly conserved proteins that play a role in cell motility, structure and integrity (RefSeq, 2002). Single nucleotide polymorphisms or copy number variations of ACTA2 have been identified in chronic lymphocytic leukemia, brain metastases of non-small cell lung cancer and cell lines derived from metastatic melanoma (Berndt et al., 2013; Lee et al., 2012; Dutton-Regester et al., 2012). Functionally, high expression levels of ACTA2 appear to be associated with enhanced tumor cell invasion and metastasis formation (Kojima et al., 2014; Lee et al., 2013b; Tatenhorst et al., 2004).

The gene for ACTB encodes beta actin, a major constituent of the contractile apparatus and one of the two non-muscle cytoskeletal actins (RefSeq, 2002). ACTB was shown to be de-regulated in liver cancer, melanoma, renal cancer, colorectal cancer, gastric cancer, pancreatic cancer, esophageal cancer, lung cancer, breast cancer, prostate cancer, ovarian cancer, leukemia and lymphoma. The abnormal expression and polymerization of ACTB and the resulting changes to the cytoskeleton appear to be associated with the invasiveness and metastasis of cancers (Guo et al., 2013).

The gene for ACTBL2 encodes kappa actin, a member of the actin family of proteins, which are highly conserved proteins that play a role in cell motility, structure and integrity (RefSeq, 2002). Increased expression of ACTBL2 was observed in hepatocellular carcinoma and hepatoma cells, where it altered cell growth properties and contributed to poor postoperative prognosis (Chang et al., 2006; Chang et al., 2011).

The gene for ACTC1 encodes the cardiac muscle alpha actin 1, which is a major constituent of the contractile apparatus in cardiac myocytes (RefSeq, 2002). Altered expression of ACTC1 was reported in bladder cancer, paclitaxel-treated non-small lung cancer cells and chemoresistant ovarian cancer (Zaravinos et al., 2011; Che et al., 2013; Pan et al., 2009). Furthermore, ACTC1 might be a useful diagnostic marker for prostate cancer and rhabdomyosarcoma (Huang et al., 2010; Clement et al., 2003).

The gene for ACTG1 encodes actin gamma 1, a cytoplasmic actin found in non-muscle cells, which acts as mediator of internal cell motility (RefSeq, 2002). ACTG1 was shown to be over-expressed in small cell lung cancer and osteosarcoma and down-regulated in epithelial ovarian cancer (Li et al., 2010; Jeong et al., 2011; Chow et al., 2010). Alterations in ACTG1 levels have been reported to promote invasion and metastasis formation in different types of cancer cells. In colon cancer cells and hepatocellular carcinoma cells overexpression of ACTG1 enhances migration and invasion, whereas in melanoma cells and salivary gland adenocarcinoma cells down-regulation of ACTG1 is associated with this phenotype (Simiczyjew et al., 2014; Luo et al., 2014; Zhang et al., 2006; Gutgemann et al., 2001; Suzuki et al., 1998).

The gene for ACTG2 encodes actin gamma 2; a smooth muscle actin found in enteric tissues, which mediates internal cell motility (RefSeq, 2002). ACTG2 is discussed as potential biomarker for prostate cancer diagnosis and was shown to be up-regulated in transdifferentiated prostate stromal cells (Fillmore et al., 2014; Untergasser et al., 2005). Regarding chemotherapy, ACTG2 is up-regulated upon paclitaxel treatment of laryngeal cancer cells, appears to be implicated in cisplatin resistance in breast cancer cells and was shown to positively correlate with the sensitivity of colorectal cancer with liver metastases to the FOLFOX4 regimen (Xu et al., 2013; Watson et al., 2007; Lu et al., 2013b).

The gene for ADAM8 encodes ADAM metallopeptidase domain 8, a member of the disintegrin and metalloprotease domain family that is involved in cell-cell and cell-matrix interactions (RefSeq, 2002). ADAM8 over-expression in pancreatic cancer is associated with increased migration and invasiveness of pancreatic ductal adenocarcinoma cells (Schlomann et al., 2015). ADAM8 is involved in tumor cell migration and invasion in lung cancer, renal cell carcinoma and brain cancers (Mochizuki and Okada, 2007).

The gene for AEBP1 encodes adipocyte enhancer binding protein 1, a carboxypeptidase A that may function as a transcriptional co-repressor with importance for adipogenesis and smooth muscle cell differentiation (RefSeq, 2002). AEBP1 is up-regulated in melanoma and contributes to acquired resistance to mutant v-raf murine sarcoma viral oncogene homolog B1 (BRAF) inhibition (Hu et al., 2013). AEBP1 is up-regulated in the majority of primary glioblastoma (Reddy et al., 2008).

The gene for AHNAK2 encodes the scaffold protein AHNAK nucleoprotein 2 (Marg et al., 2010). AHNAK2 is an important element of the non-classical secretion pathway of fibroblast growth factor 1 (FGF1), a factor involved in tumor growth and invasion (Kirov et al., 2015).

The gene for ANKH encodes ankylosis, progressive homolog (mouse)/ANKH inorganic pyrophosphate transport regulator, a multipass transmembrane protein that controls pyrophosphate levels (RefSeq, 2002).

The gene for ANO1 encodes anoctamin 1, a calcium-activated chloride channel associated with small intestinal sarcoma and oral cancer (RefSeq, 2002). ANO1 is amplified in esophageal squamous cell cancer (ESCC), gastrointestinal stromal tumor (GIST), head and neck squamous cell carcinoma (HNSCC), pancreatic and breast cancers (Qu et al., 2014).

The gene for APOB encodes apolipoprotein B, the main apolipoprotein of chylomicrons and low density lipoproteins (LDH) (RefSeq, 2002). In alpha-fetoprotein-negative HBV-related HCC, APOB was found to be one of the 14 differentially expressed proteins which could be associated with HCC progression (He et al., 2014). In advanced breast cancer, APOB was found to be the one of 6 differentially expressed proteins which could predict the responsiveness to neoadjuvant chemotherapy and relapse-free survival of patients (Hyung et al., 2011).

The gene for ASPHD1 encodes aspartate beta-hydroxylase domain containing 1. ASPHD1 is located on chromosome 16p11.2 (RefSeq, 2002).

The gene for ATM encodes ataxia telangiectasia mutated, a PI3/PI4-kinase family member and master controller of cell cycle checkpoint signaling pathways that are required for cell response to DNA damage and for genome stability (RefSeq, 2002). ATM is a tumor suppressor which is frequently mutated in a broad range of human cancers including lung, colorectal, breast and hematopoietic cancers (Weber and Ryan, 2014).

The gene for ATP5B encodes ATP synthase, H+ transporting, mitochondrial F1 complex, beta polypeptide, the beta subunit of the catalytic core of mitochondrial ATP synthase (RefSeq, 2002). ATP5B gene expression was significantly higher in colorectal cancer tissues compared to healthy tissues (Geyik et al., 2014). ATP5B down-regulation in tumor tissues is closely related to the metastasis, invasion, and poor-prognosis of gallbladder cancer (Sun et al., 2015b).

The gene for ATP5L encodes ATP synthase, H+ transporting, mitochondrial Fo complex, subunit G of the membrane-spanning component of the mitochondrial ATP synthase, which comprises the proton channel (RefSeq, 2002).

The gene for ATP5L2 encodes ATP synthase, H+ transporting, mitochondrial Fo complex, subunit G2 of the membrane-spanning component of the mitochondrial ATP synthase, which comprises the proton channel (RefSeq, 2002).

The gene for BACE2 encodes beta-site APP-cleaving enzyme 2, an integral membrane glycoprotein and aspartic protease. BACE2 cleaves amyloid precursor protein into amyloid beta peptide (RefSeq, 2002). BACE2 is involved in pancreatic beta-cell function (Vassar et al., 2014).

The gene for CCNB1 encodes cyclin B1, a regulatory protein involved in mitosis (RefSeq, 2002). CCNB1 is a well-described tumor antigen and CCNB1 over-expression has been described for breast, head and neck, prostate, colorectal, lung and liver cancers (Egloff et al., 2006).

The gene for CEACAM6 encodes carcinoembryonic antigen-related cell adhesion molecule 6 (non-specific cross reacting antigen), a member of the CEACAM family of tumor markers (RefSeq, 2002). CEACAM6 is up-regulated in gastric cancers (Yasui et al., 2004). CEACAM6 is a candidate breast tumor antigen (Sood, 2010).

The gene for CLTA encodes clathrin, light chain A, a structural component of coated pits with regulatory function (RefSeq, 2002). The CLTA gene shows an alternative splice pattern in glioma (Cheung et al., 2008).

The gene for CTLB encodes clathrin, light chain B, a structural component of coated pits with regulatory function (RefSeq, 2002).

The gene for CLU encodes a secreted chaperone that might be involved in several basic biological events such as cell death, tumor progression, and neurodegenerative disorders (RefSeq, 2002). Its role in tumorigenesis appears to be ambivalent as in normal cells and during early phases of carcinogenesis, CLU may inhibit tumor progression, whereas in advanced neoplasia, it may offer a significant survival advantage in the tumor by suppressing many therapeutic stressors and enhancing metastasis. CLU has been shown to play a critical role in prostate cancer pathogenesis, to regulate the aggressive behavior of human clear renal cell carcinoma cells through modulating ERK1/2 signaling and MMP-9 expression and to confer resistance to treatment in advanced stages of lung cancer (Trougakos, 2013; Panico et al., 2009; Takeuchi et al., 2014; Wang et al., 2014b).

The gene for COL12A1 encodes the alpha chain of type XII collagen, a member of the FACIT (fibril-associated collagens with interrupted triple helices) collagen family and thus is a part of extracellular matrix (ECM) (RefSeq, 2002). COL12A1 is over-expressed in drug-resistant variants of ovarian cancer cell lines (Januchowski et al., 2014). In colorectal cancer, COL12A1 is over-expressed in desmoplastic stroma by and around cancer-associated fibroblasts, as well as in cancer cells lining the invasion front (Karagiannis et al., 2012).

The gene for COL6A3 encodes the alpha-3 chain of type VI collagen, a beaded filament collagen found in most connective tissues, playing an important role in the organization of matrix components (RefSeq, 2002). COL6A3 expression was reported to be increased in pancreatic cancer, colon cancer, gastric cancer, mucoepidermoid carcinomas and ovarian cancer. Cancer associated transcript variants including exons 3, 4 and 6 were detected in colon cancer, bladder cancer, prostate cancer and pancreatic cancer (Arafat et al., 2011; Smith et al., 2009; Yang et al., 2007; Xie et al., 2014; Leivo et al., 2005; Sherman-Baust et al., 2003; Gardina et al., 2006; Thorsen et al., 2008). In ovarian cancer COL6A3 levels correlated with higher tumor grade and in pancreatic cancer COL6A3 was shown to represent a suitable diagnostic serum biomarker (Sherman-Baust et al., 2003; Kang et al., 2014).

The gene for DCBLD2 encodes discoidin, CUB and LCCL domain-containing protein 2 also referred to as endothelial and smooth muscle cell-derived neuropilin-like protein, a transmembrane co-receptor protein (RefSeq, 2002). DCBLD2 is up-regulated in glioblastomas and head and neck cancers (HNCs) and is required for EGFR-stimulated tumorigenesis (Feng et al., 2014). Furthermore, DCBLD2 is up-regulated in highly metastatic lung cancer sublines and tissue samples (Koshikawa et al., 2002). In contrast, the expression of DCBLD2 is silenced by hypermethylation of its promoter in gastric cancer (Kim et al., 2008).

The gene for DUSP14, the dual-specificity phosphatase 14, can de-phosphorylate tyrosine as well as serine/threonine residues and plays a role in the inactivation of MAP kinase signaling (RefSeq, 2002). Single nucleotide polymorphisms in the DUSP14 gene are associated with altered melanoma risk (Yang et al., 2014a; Liu et al., 2013a).

The gene for EEF1A1 encodes an isoform of the alpha subunit of the elongation factor-1 complex, which is responsible for the enzymatic delivery of aminoacyl tRNAs to the ribosome (RefSeq, 2002). EEF1A1 was shown to be up-regulated in a variety of cancer entities, including colorectal cancer, ovarian cancer, gastric cancer, prostate cancer, glioblastoma and squamous cell carcinoma and was described as potential serum biomarker for prostate cancer (Matassa et al., 2013; Vui-Kee et al., 2012; Lim et al., 2011; Kuramitsu et al., 2010; Kido et al., 2010; Scrideli et al., 2008; Qi et al., 2005; Rehman et al., 2012). Mechanistically, EEF1A1 inhibits apoptosis through an interaction with p53 and p73, promotes proliferation by transcriptional repression of the cell cycle inhibitor p21 and participates in the regulation of epithelial-mesenchymal transition (Blanch et al., 2013; Choi et al., 2009; Hussey et al., 2011).

The gene for EEF1A1P5 encodes eukaryotic translation elongation factor 1 alpha 1 pseudogene 5 and is located on chromosome 9q34.13 (RefSeq, 2002).

The gene for FAMC3 is a member of the family with sequence similarity 3 (FAM3) family and encodes a secreted protein with a GG domain. A change in expression of this protein has been noted in pancreatic cancer-derived cells (RefSeq, 2002). In melanoma, FAMC3 has been identified as a candidate biomarker for autophagy, an important tumor cell survival mechanism (Zou et al., 2002; Kraya et al., 2015). FAMC3 plays an essential role in the epithelial-mesenchymal transition which correlates with aggressiveness, metastatic progression of tumors and poor survival especially in hepatocellular cancer, colorectal cancer, lung and breast cancers (Csiszar et al., 2014; Gao et al., 2014c; Song et al., 2014; Chaudhury et al., 2010; Lahsnig et al., 2009).

The gene for FAP encodes a transmembrane serine protease which is selectively expressed in reactive stromal fibroblasts of epithelial cancers (cancer-associated fibroblasts or CAFs), granulation tissue of healing wounds, and malignant cells of bone and soft tissue sarcomas (RefSeq, 2002). FAP plays an important role in cancer growth and metastasis through its involvement in cell adhesion, migration processes and remodeling of the extracellular matrix (ECM) (Jacob et al., 2012). The over-expression of FAP correlates with poor prognosis, advanced tumor staging, metastasis formation and invasive potential in various cancers, thereunder in colon cancer, esophageas squamous cell carcinoma, pancreatic adenocarcinoma, glioblastoma, osteosarcoma, ovarian cancer and breast cancer (Wikberg et al., 2013; Kashyap et al., 2009; Cohen et al., 2008; Mentlein et al., 2011; Yuan et al., 2013; Zhang et al., 2011; Ariga et al., 2001).

The gene for FKBP10 encodes the FK506 binding protein 10, which belongs to the FKBP-type peptidyl-prolyl cis/trans isomerase family. The FKBP10 gene product localizes to the endoplasmic reticulum and acts as a molecular chaperone (RefSeq, 2002). FKBP10 was identified as a novel gene that participates in the acquisition and maintenance of the adriamycin-resistant phenotype in leukemia cells (Sun et al., 2014). FKBP10 has been associated with colorectal cancer through its up-regulation (Olesen et al., 2005). In contrast, the under-expression of FKBP10 was characteristic for epithelial ovarian carcinomas (Quinn et al., 2013).

The gene for FLNA encodes filamin A, an actin-binding protein that crosslinks actin filaments and links actin filaments to membrane glycoproteins. The encoded protein is involved in the remodeling of the cytoskeleton which induces changes in cell shape and migration and interacts with integrins, transmembrane receptor complexes, and second messengers (RefSeq, 2002). Depending on its subcellular localization, filamin A plays a dual role in cancer: In the cytoplasm, filamin A functions in various growth signaling pathways, in addition to being involved in cell migration and adhesion pathways. Thus, its over-expression has a tumor-promoting effect. In contrast to full-length filamin A, the C-terminal fragment, which is released upon proteolysis of the protein, localizes to the nucleus, where it interacts with transcription factors and thereby suppresses tumor growth and metastasis (Savoy and Ghosh, 2013).

The gene for GGA1 encodes a member of the Golgi-localized, gamma adaptin ear-containing, ARF-binding (GGA) protein family. Members of this family are ubiquitous coat proteins that regulate the trafficking of proteins between the trans-Golgi network and the lysosome (RefSeq, 2002).

The gene for HBB encodes the beta chain of human hemoglobin, the iron-containing oxygen-transport metalloprotein in the red blood cell (RefSeq, 2002). The ability of breast cancer to generate bone and visceral metastases represents a clear indication of poor clinical outcome compared to cases of breast cancer with metastasis restricted to bone. The increased expression of HBB in bone metastasis correlated with their ability to rapidly spread to other organs (Capulli et al., 2012). HBB was shown to be over-expressed in uterine cervix carcinoma tissue. The ectopic expression of HBB in cervical cancer cells suppressed oxidative stress and improved cell viability (Li et al., 2013).

The gene for HBD encodes the delta chain of human hemoglobin, the iron-containing oxygen-transport metalloprotein in the red blood cell. Two alpha chains plus two delta chains constitute hemoglobin A2, which with HbF comprises 3% of adult hemoglobin (RefSeq, 2002).

The gene for HKDC1 encodes hexokinase domain containing 1, which exhibits the hexokinase activity in vitro (Guo et al., 2015). Using a novel method to identify potential therapeutic targets from heterogeneous data, HKDC1, among other well-known therapeutic targets, was discovered as a novel potential therapeutic target for lung cancer (Li and Huang, 2014).

The gene for HSPD1 encodes a mitochondrial heat shock 60 kDa protein 1, a member of the chaperonin family, which is essential for the folding and assembly of newly imported proteins in the mitochondria and may function as a signaling molecule in the innate immune system (RefSeq, 2002). Although HSPD1 is considered an intramitochondrial protein, it has been found in the cytosol, cell membrane, vesicles, cell surface, extracellular space, and blood. As cytosolic HSPD1 levels gradually increase or decrease during carcinogenesis in various organs, HSPD1 can be used as a biomarker for the diagnosis and prognosis of pre-neoplastic and neoplastic lesions. Furthermore, some newly identified functions of HSPD1 are associated with carcinogenesis, specifically with tumor cell survival and proliferation and it has been intensively discussed as a promising target for anti-tumor therapy (Pace et al., 2013; Nakamura and Minegishi, 2013; Cappello et al., 2013; Cappello et al., 2011; Cappello et al., 2008).

The gene for HYOU1 encodes hypoxia up-regulated 1 protein, better known as 170 kDa glucose-regulated protein (GRP170), which belongs to the heat shock protein 70 family. The expression of HYOU1 is induced in stress-dependent manner under hypoxic conditions and results in the accumulation of the protein in the endoplasmic reticulum (ER). The protein encoded by HYOU1 is thought to play an important role in protein folding and secretion in the ER (RefSeq, 2002). The activity of intracellular HYOU1 protein has been shown to provide a survival benefit in cancer cells during tumor progression or metastasis. The extracellular HYOU1 protein plays an essential role in the generation of an anti-tumor immune response by facilitating the delivery of tumor antigens for their cross-presentation (Fu and Lee, 2006; Wang et al., 2014a). HYOU1 protein has been introduced in cancer immunotherapy and showed a positive immunomodulating effect (Yu et al., 2013; Chen et al., 2013a; Yuan et al., 2012; Wang and Subjeck, 2013). In prostate cancer cells, the suppression of HYOU1 showed an anti-tumor effect (Miyagi et al., 2001).

The gene for IFT88 encodes a member of the tetratrico peptide repeat (TPR) family (RefSeq, 2002). In mitosis, IFT88 is part of a dynein1-driven complex that transports peripheral microtubule clusters to spindle poles to ensure proper spindle orientation. IFT88 depletion induces mitotic defects in human cultured cells (Delaval et al., 2011). Loss of IFT88 (also called Tg737) gene expression results in the proliferation of liver stem cells (oval cells) and is therefore a liver neoplasia tumor suppressor gene (Isfort et al., 1997). In 2012 a mutation was found to be responsible for a novel form of ciliopathy and anosmia in humans capable of remedy in mice by adenoviral mediated gene therapy (McIntyre et al., 2012).

The gene for IGF2BP3 encodes insulin-like growth factor II mRNA binding protein 3, an oncofetal protein, which represses translation of insulin-like growth factor II (RefSeq, 2002). Several studies have shown that IGF2BP3 acts in various important aspects of cell function, such as cell polarization, migration, morphology, metabolism, proliferation and differentiation. In vitro studies have shown that IGF2BP3 promotes tumor cell proliferation, adhesion, and invasion. Furthermore, IGF2BP3 has been shown to be associated with aggressive and advanced cancers (Bell et al., 2013; Gong et al., 2014). IGF2BP3 over-expression has been described in numerous tumor types and correlated with poor prognosis, advanced tumor stage and metastasis, as for example in neuroblastoma, colorectal carcinoma, intrahepatic cholangiocarcinoma, hepatocellular carcinoma, prostate cancer, and renal cell carcinoma (Bell et al., 2013; Findeis-Hosey and Xu, 2012; Hu et al., 2014; Szarvas et al., 2014; Jeng et al., 2009; Chen et al., 2011; Chen et al., 2013b; Hoffmann et al., 2008; Lin et al., 2013b; Yuan et al., 2009).

The gene for ITGB4 encodes for a protein of the Integrin family. Integrins are heterodimers comprised of alpha and beta subunits that are non-covalently associated transmembrane glycoprotein receptors. They mediate cell-matrix or cell-cell adhesion, and transduce signals that regulate gene expression and cell growth (RefSeq, 2002). ITGB4 (also called CD104) tends to associate with the alpha 6 subunit and is likely to play a pivotal role in the biology of several invasive carcinomas such as esophageal squamous cell carcinoma, bladder and ovarian carcinoma (Kwon et al., 2013; Pereira et al., 2014; Chen et al., 2014b). A single nucleotide polymorphism in ITGB4 seems to influence tumor aggressiveness and survival and may have prognostic value for breast cancer patients (Brendle et al., 2008).

The gene for KCNK6 encodes one of the members of the superfamily of potassium channel proteins containing two pore-forming P domains. This channel protein, considered an open rectifier, is widely expressed. It is stimulated by arachidonic acid, and inhibited by internal acidification and volatile anesthetics (RefSeq, 2002). KCNK6 (also called K2P6.1) together with K2P1.1, K2P3.1, K2P5.1, K2P6.1, K2P7.1 and K2P10.1 showed significant under-expression across the cancer types examined using the online cancer microarray database, Oncomine (www.oncomine.org) (Williams et al., 2013).

The gene for KCNN3 belongs to the KCNN family of potassium channels. It encodes an integral membrane protein that forms a voltage-independent calcium-activated channel, which is thought to regulate neuronal excitability by contributing to the slow component of synaptic after hyperpolarization (RefSeq, 2002). KCNN3 (also called TASK-1) expression was down-regulated by 17beta-estradiol in mouse neuroblastoma N2A cells and improved cell proliferation (Hao et al., 2014). KCNN3 expression was up-regulated by exposure of breast cancer organotypic culture to 1,25 dihydroxy vitamin D (3) in physiological and supra-physiological concentrations (Milani et al., 2013). KCNN3 (also called K2P3.1) together with K2P1.1 and K2P12.1, were over-expressed in a range of cancers examined using the online cancer microarray database, Oncomine (www.oncomine.org) (Williams et al., 2013).

The gene for KDM1A (also called LSD1) encodes a nuclear protein containing a SWIRM domain, a FAD-binding motif, and an amine oxidase domain. This protein is a component of several histone deacetylase complexes, though it silences genes by functioning as a histone demethylase (RefSeq, 2002). Over-expression of KDM1A promotes tumor cell proliferation, migration and invasion and was associated with poor prognosis in NSCLC and HCC (Lv et al., 2012; Zhao et al., 2013). Elevated expression of KDM1A correlates with prostate cancer recurrence and with increased VEGF-A expression (Kashyap et al., 2013). Inhibition of KDM1A with a combination of trichostatin A (TSA) and 5-aza-2'-deoxycytidine (decitabine) suppresses the tumorigenicity of the ovarian cancer ascites cell line SKOV3 (Meng et al., 2013).

The gene for KIF26B encodes for a member of the kinesin superfamily proteins (KIFs) which is essential for kidney development. KIF26B expression is restricted to the metanephric mesenchyme, and its transcription is regulated by a zinc finger transcriptional regulator Sall1 (Terabayashi et al., 2012). High expression of KIF26B in breast cancer associates with poor prognosis (Wang et al., 2013b). KIF26B up-regulation was significantly correlated with tumor size analyzing CRC tumor tissues and paired adjacent normal mucosa. KIF26B plays an important role in colorectal carcinogenesis and functions as a novel prognostic indicator and a potential therapeutic target for CRC (Wang et al., 2015).

The gene for KRT19 encodes a member of the keratin family. The keratins are intermediate filament proteins responsible for the structural integrity of epithelial cells and are subdivided into cytokeratins and hair keratins. KRT19 is specifically expressed in the periderm, the transiently superficial layer that envelopes the developing epidermis (RefSeq, 2002). KRT19 expression in tumor cells is a prognostic marker for several tumor entities such as breast, lung, ovarian and hepatocellular cancer (Skondra et al., 2014; Gao et al., 2014b; Liu et al., 2013b; Lee et al., 2013a). KRT19 has been shown to be an independent prognostic factor for pancreatic neuroendocrine tumors, especially the insulin-negative tumors. KRT19 positive tumors are associated with poor outcome irrespective of the established pathologic parameters such as size, mitoses, lymphovascular invasion, and necrosis (Jain et al., 2010).

The gene for KRT7 encodes a member of the keratin gene family. The type II cytokeratins consist of basic or neutral proteins which are arranged in pairs of heterotypic keratin chains co-expressed during differentiation of simple and stratified epithelial tissues. This type II cytokeratin is specifically expressed in the simple epithelia lining the cavities of the internal organs and in the gland ducts and blood vessels (RefSeq, 2002). KRT7 is used in immunohistochemistry to differentiate between several phenotypes and as biomarker for prognosis of certain cancers as renal cell carcinoma, ovarian carcinoma, epithelial skin tumor etc. (Kuroda et al., 2013; McCluggage and Young, 2005; Alhumaidi, 2012).

The gene for LAMC2 belongs to the family of laminins, a family of extracellular matrix glycoproteins. Laminins are the major non-collagenous constituent of basement membranes. They have been implicated in a wide variety of biological processes including cell adhesion, differentiation, migration, signaling, neurite outgrowth and metastasis. LAMC2 encodes a protein which is expressed in several fetal tissues and is specifically localized to epithelial cells in skin, lung and kidney (RefSeq, 2002). LAMC2 is highly expressed in anaplastic thyroid carcinoma and is associated with tumor progression, migration, and invasion by modulating signaling of EGFR (Garg et al., 2014). LAMC2 expression predicted poorer prognosis in stage II colorectal cancer patients (Kevans et al., 2011). LAMC2 expression together with three other biomarkers was found to be significantly associated with the presence of LN metastasis in oral squamous cell carcinoma patients (Zanaruddin et al., 2013).

The gene for LUM encodes a member of the small leucine-rich proteoglycan (SLRP) family that includes decorin, biglycan, fibromodulin, keratocan, epiphycan, and osteoglycin. Lumican is the major keratan sulfate proteoglycan of the cornea but is also distributed in interstitial collagenous matrices throughout the body. Lumican may regulate collagen fibril organization and circumferential growth, corneal transparency, and epithelial cell migration and tissue repair (RefSeq, 2002). LUM protein is up-regulated in most tumor tissues such as breast cancer, colorectal cancer and pancreatic cancer compared to normal tissue and is associated with higher tumor grade and poor outcome. However extracellular lumican inhibits pancreatic cancer cell growth and is associated with prolonged survival after surgery (Leygue et al., 1998; Seya et al., 2006; Ishiwata et al., 2007; Li et al., 2014). LUM and other genes related to extracellular matrix integrity (DCN and DPT) are differentially expressed and may serve as biomarkers for metastatic and recurrent giant cell tumor of bone (Lieveld et al., 2014). LUM is down-regulated in cisplatin-, doxorubicin-, topotecan-, and paclitaxel-resistant variants of the A2780 ovarian cancer cell line (Januchowski et al., 2014).

The gene for MAP4 encodes a major non-neuronal microtubule-associated protein, which promotes microtubule assembly and counteracts destabilization of interphase microtubule catastrophe promotion. Phosphorylation of this protein affects microtubule properties and cell cycle progression (RefSeq, 2002). High levels of MAP4 were shown to positively correlate with bladder cancer grade, whereas phosphorylation of the protein by protein kinase A reduces bladder cancer cell migration and invasion (Ou et al., 2014). A study in non-small cell lung cancer patients reported an increased ratio of MAP4 to stathmin mRNA in tumor samples compared to normal samples, indicating that this ratio could serve as biomarker for non-small cell lung cancer (Cucchiarelli et al., 2008). MAP4 levels, which are negatively regulated by the tumor suppressor p53, influence the efficacy of microtubule-targeting agents. High levels increase the effect of microtubule stabilizing drugs (taxanes) and reduce the effect of microtubule destabilizing drugs (vinca alkaloids), while low MAP4 levels have the opposite effect (Hait and Yang, 2006; Galmarini et al., 2003; Zhang et al., 1999).

The gene for MMP7 encodes an enzyme that degrades proteoglycans, fibronectin, elastin and casein and differs from most MMP family members in that it lacks a conserved C-terminal protein domain. Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis (RefSeq, 2002). MMP7 is frequently over-expressed in human cancer tissue, including colorectal cancer, metastatic lung carcinoma and gastric cancer and is associated with cancer progression and metastasis formation (Ii et al., 2006; Sun et al., 2015a; Han et al., 2015; Long et al., 2014). MMP7 has been shown to play important tumor promoting roles, like degradation of extracellular matrix proteins, activation of tumor cell proliferation by increasing the bioavailability of insulin-like growth factor and heparin-binding epidermal growth factor and induction of apoptosis in tumor-adjacent cells by cleaving membrane bound Fas ligand (Ii et al., 2006).

The gene for MROH6, also known as C8orf73, is located on chromosome 8q24.3 (RefSeq, 2002).

The gene for MX1 encodes a guanosine triphosphate (GTP)-metabolizing protein that is induced by type I and type II interferons and participates in the cellular antiviral response (RefSeq, 2002). The role of MX1 in cancer is not fully elucidated yet. On the one hand MX1 expression inversely correlates with prostate cancer, reduces metastasis formation and enhances the sensitivity to docletaxel. Furthermore, epigenetic silencing of MX1 by hypermethylation has been detected in head and neck squamous cell carcinoma and MX1 expression reduces cell motility and invasion of prostate cancer and melanoma cell lines, all favoring tumor suppressive actions of MX1 (Brown et al., 2015; Calmon et al., 2009; Mushinski et al., 2009). On the other hand, a single nucleotide polymorphism within the MX1 gene is associated with prostate cancer and high expression of MX1 is associated with lymph node metastasis in colorectal cancer, which indicates oncogenic properties of MX1 (Croner et al., 2014; Glymph et al., 2013).

The gene for MXRA5 encodes one of the matrix-remodeling associated proteins, which contains 7 leucine-rich repeats and 12 immunoglobulin-like C2-type domains related to perlecan (RefSeq, 2002). A Chinese study identified MXRA5 as the second most frequently mutated gene in non-small cell lung cancer (Xiong et al., 2012). In colon cancer, MXRA5 was shown to be over-expressed and might serve as a biomarker for early diagnosis and omental metastasis (Zou et al., 2002; Wang et al., 2013a).

The gene for MYH9 encodes a conventional non-muscle myosin IIA heavy chain that contains an IQ domain and a myosin head-like domain which is involved in several important functions, including cytokinesis, cell motility and maintenance of cell shape (RefSeq, 2002). High expression of MYH9 was shown to be associated with poor prognosis in esophageal squamous cell carcinoma and, in combination with annexin II and kindling-2, might serve as predictive biomarker for overall and disease free survival in this disease (Xia et al., 2012; Cao et al., 2014). Mutations within the MYH9 gene have been identified in human breast cancer samples and it is differentially expressed in colon carcinoma (Ellis et al., 2012; Mu et al., 2013). In vitro and xenograft studies indicate that MYH9 promotes tumor cell growth and invasion of different tumor cell lines, including breast cancer and non-small lung cancer cells (Robinson et al., 2013; Lin et al., 2013a; Lund et al., 2012; Derycke et al., 2011; Medjkane et al., 2009).

The gene for MYL12A encodes a non-sarcomeric myosin regulatory light chain, which regulates smooth muscle and non-muscle cell contraction (Amatschek et al., 2004; RefSeq, 2002). Phosphorylation of MYL12A was reported to promote tumor cell motility and invasion in vitro and in the animal model (Manning, Jr. et al., 2000; Kaneko et al., 2002; Khuon et al., 2010). Furthermore, MYL12A appears to regulate DNA damage repair and p53-driven apoptosis, by sequestering the transcriptional regulator apoptosis-antagonizing transcription factor (Hopker et al., 2012a; Hopker et al., 2012b).

The gene for MYL12B encodes a regulatory light chain of the non-muscle myosin II (MYH9). Phosphorylation of MYL12B results in higher MgATPase activity and the assembly of myosin II filaments (RefSeq, 2002). The protein was shown to be up-regulated in grade 3 ovarian cancer and pharmacologic block of MYL12B phosphorylation or activation decreased tumor cell migration and invasion in vitro and metastasis formation in an animal model for breast cancer. These data indicate a pro-metastatic role for MYL12B (Lim et al., 2011; Menhofer et al., 2014; Zhang et al., 2013; Patel et al., 2012).

The gene for PARD3B encodes a protein that localizes to tight junctions of epithelial cells and participates in the establishment of cell polarity (Izaki et al., 2005). A single nucleotide polymorphism within the PARD3B gene was shown to be significantly associated with severe treatment-related hepatotoxicity in children with acute lymphoblastic leukemia or lymphoblastic lymphoma (Horinouchi et al., 2010).

The gene for PDIA6 (also called ERp5) encodes a protein disulfide isomerase which is an endoplasmic reticulum (ER) resident protein that catalyzes formation, reduction, and isomerization of disulfide bonds in proteins and is thought to play a role in folding of disulfide-bonded proteins (RefSeq, 2002). Immunostaining of prostate tissue microarrays for PDIA6 showed a significantly higher immunoreactivity in pre-malignant lesions compared with non-malignant epithelium ($P<0.0001$, Mann-Whitney U-test), and in high Gleason grade (4-5) versus low grade (2-3) cancers ($P<0.05$) (Glen et al., 2010). High ERp5/ADAM10 expression leads to MICA shedding and impaired NKG2D ligands recognition in lymph node microenvironment in Hodgkin lymphomas. This leads to down-modulation of NKG2D surface expression on CD8 T cells and an inefficient anti-tumor response (Zocchi et al., 2012). The protein disulfide isomerases PDIA4 and PDIA6 mediate resistance to cisplatin-induced cell death in lung adenocarcinoma (Horibe et al., 2014).

The gene for PIK3IP1 encodes phosphoinositide-3-kinase interacting protein 1, a PI3K inhibitor (RefSeq, 2002). PIK3IP1 down-regulation leads to increased tumor growth in human T-cell lymphoblastic lymphoma cells (Wong et al., 2014). PIK3IP1 is down-regulated in hepatocellular carcinoma (HCC) and PIK3IP1 suppresses the development of HCC (He et al., 2008).

The gene for PLEC encodes the plakin family member plectin, a protein involved in the cross-linking and organization of the cytoskeleton and adhesion complexes (Bouameur et al., 2014). PLEC is over-expressed in colorectal adenocarcinoma, head and neck squamous cell carcinoma and pancreatic cancer (Lee et al., 2004; Katada et al., 2012; Bausch et al., 2011).

The gene for POTEE encodes POTE ankyrin domain family, member E, one of 13 paralogs belonging to the POTE gene family. POTE genes are thought to represent a new family of cancer-testis antigens. The biological function of the POTE gene family is not fully elucidated yet, but some evidence suggests a pro-apoptotic role (Liu et al., 2009; Bera et al., 2006). POTEE is predominantly expressed in prostate, breast, colon, lung and ovarian cancer (Bera et al., 2006). One study described POTEE to be closely related to breast cancer, using a combined transcriptomic and proteomic approach (Cine et al., 2014).

The gene for POTEF encodes POTE ankyrin domain family, member J, one of 13 paralogs belonging to the POTE gene family. POTE genes are thought to represent a new family of cancer-testis antigens. The biological function of the POTE gene family is not fully elucidated yet, but some evidence suggests a pro-apoptotic role (Liu et al., 2009; Bera et al., 2006). POTEF was shown to induce apoptosis in Hela cells through a mitochondrial pathway (Liu et al., 2009). POTEF is predominantly expressed in prostate, breast, colon, lung and ovarian cancer (Bera et al., 2006).

The gene for POTEI is located on chromosome 2q21.1 and encodes POTE ankyrin domain family, member I, one of 13 paralogs belonging to the POTE gene family. POTE genes are thought to represent a new family of cancer-testis antigens. The biological function of the POTE gene family is not fully elucidated yet, but some evidence suggests a pro-apoptotic role (Liu et al., 2009; Bera et al., 2006). POTEI is predominantly expressed in prostate, breast, colon, lung and ovarian cancer (Bera et al., 2006).

The gene for POTEJ encodes POTE ankyrin domain family, member J, one of 13 paralogs belonging to the POTE gene family. POTE genes are thought to represent a new family of cancer-testis antigens. The biological function of the POTE gene family is not fully elucidated yet, but some evidence suggests a pro-apoptotic role (Liu et al., 2009; Bera et al., 2006). POTEJ is predominantly expressed in prostate, breast, colon, lung and ovarian cancer (Bera et al., 2006).

The gene for POTEKP encodes POTE ankyrin domain family, member K, pseudogene and is located on chromosome 2q21.1 (RefSeq, 2002).

The gene for POTEM encodes POTE ankyrin domain family, member M, one of 13 paralogs belonging to the POTE gene family. POTE genes are thought to represent a new family of cancer-testis antigens. The biological function of the POTE gene family is not fully elucidated yet, but some evidence suggests a pro-apoptotic role (Liu et al., 2009; Bera et al., 2006). POTEM was identified as specific transcript for normal and malignant prostate tissue (Stolk et al., 2004).

The gene for PTRF encodes polymerase I and transcript release factor, a regulator of rRNA transcription that promotes the dissociation of transcription complexes and the re-initiation of polymerase I on nascent rRNA transcripts (RefSeq, 2002). PTRF is down-regulated in breast cancer cell lines and breast tumor tissue (Bai et al., 2012). PTRF is a non-small cell lung cancer biomarker (Gamez-Pozo et al., 2012). PTRF expression is down-regulated in prostate cancer and the absence of PTRF in prostate cancer cells contributes significantly to tumor progression and metastasis by promoting the angiogenic potential of cancer cells (Nassar et al., 2013).

The gene for PUS7L encodes pseudouridylate synthase 7 homolog (s. cerevisiae)-like, a protein with possible pseudouridine synthase activity. The PUS7L gene is located on chromosome 12q12 (RefSeq, 2002).

The gene for RAN encodes RAN, member RAS oncogene family, a small GTP binding protein that is involved in the translocation of RNA and proteins through the nuclear pore complex, in the control of DNA synthesis and cell cycle progression, in the formation and organization of the microtubule network, and in the activation of the androgen receptor (RefSeq, 2002). RAN is a key protein in the metastatic progression of cancer. RAN is over-expressed in a range of tumors, such as breast and renal (Matchett et al., 2014).

The gene for RANP1 encodes RAN, member RAS oncogene family pseudogene 1, a pseudogene located on chromosome 6p21.33 (RefSeq, 2002).

The gene for RASA4 encodes RAS p21 protein activator 4, a Ca (2+)-dependent Ras GTPase-activating protein that switches off the Ras-MAPK pathway in response to Ca (2+) (RefSeq, 2002). RASA4 is significantly amplified in primary effusion lymphoma (Roy et al., 2011). RASA4 is differentially expressed in endometrial adenocarcinoma compared to normal endometrium (Jeda et al., 2014).

The gene for RASA4B encodes RAS p21 protein activator 4B, a Ca (2+)-dependent Ras GTPase-activating protein with possible involvement in the regulation of the Ras-MAPK pathway (RefSeq, 2002).

The gene for RCN1 encodes reticulocalbin 1, EF-hand calcium binding domain, a calcium-binding protein located in the lumen of the endoplasmic reticulum. RCN1 is localized to the plasma membrane in human endothelial and prostate cancer cell lines (RefSeq, 2002). RCN1 is over-expressed in breast cancer (Amatschek et al., 2004).

The gene for RGS4 encodes regulator of G-protein signaling 4, a GTPase activating protein (GAP) for G alpha subunits of heterotrimeric G proteins (RefSeq, 2002). RGS4 revealed a statistically significant down-regulation in liver metastases and at the tumor invasion front compared with the primary pancreatic tumor (Niedergethmann et al., 2007). RGS4 is over-expressed very commonly in thyroid carcinoma, though it is not expressed in normal human tissues (Nikolova et al., 2008). RGS4 transcript was detected in non-cancerous immortalized ovarian surface epithelial cells at levels several thousand fold higher than its expression level in ovarian cancer cell lines (Hurst et al., 2009).

The gene for RPS6 encodes ribosomal protein S6, a cytoplasmic ribosomal protein that is a component of the 40S subunit of ribosomes. RPS6 may contribute to the control of cell growth and proliferation through the selective translation of particular classes of mRNA (RefSeq, 2002). RPS6 is a downstream target of mTOR and has been found to be associated with multiple physiological and pathophysiological functions (Chen et al., 2014a). RPS6 phosphorylation attenuates DNA damage and tumor suppression during development of pancreatic cancer (Khalaileh et al., 2013).

The gene for RPS8 encodes ribosomal protein S8, a cytoplasmic ribosomal protein that is a component of the 40S subunit of ribosomes. RPS8 expression is increased in colorectal tumors and colon polyps compared to matched normal colonic mucosa (RefSeq, 2002). RPS8 up-regulation in pancreatic ductal adenocarcinoma patients is correlated with short-term survival (Chen et al., 2015).

The gene for RPS8P10 encodes ribosomal protein S8 pseudogene 10, a pseudogene located on chromosome 15q11.2 (RefSeq, 2002).

The gene for SCG5 encodes secretogranin V (7B2 protein), a neuroendocrine secretory protein (Portela-Gomes et al., 2008). A duplication spanning the 3' end of the SCG5 gene and a region upstream of the GREM1 locus may increase the risk of developing colorectal cancer (Jaeger et al., 2012; Yang et al., 2014b).

The gene for SERPINB2 encodes serpin peptidase inhibitor, clade B (ovalbumin), member 2, an inhibitor of extracellular protease urokinase plasminogen activator and tissue plasminogen activator (Schroder et al., 2014). SERPINB2 is expressed in a number of different tumors. SERPINB2 expression is associated with favorable prognosis in breast and pancreatic cancers, but poor prognosis in endometrial, ovarian, and colorectal cancers (Schroder et al., 2014).

The gene for SERPINB3 encodes the protease inhibitor serpin peptidase inhibitor, clade B (ovalbumin), member 3 (RefSeq, 2002). SERPINB3 is a Ras-responsive factor that plays an important role in Ras-associated cytokine production and tumorigenesis (Catanzaro et al., 2014). SERPINB3 expression is up-regulated in hepatocellular carcinoma (Pontisso, 2014). SERPINB3 is associated with the development of ovarian cancer (Lim and Song, 2013).

The gene for SERPINB4 encodes the protease inhibitor serpin peptidase inhibitor, clade B (ovalbumin), member 4 (RefSeq, 2002). SERPINB4 is a Ras-responsive factor that plays an important role in Ras-associated cytokine production and tumorigenesis (Catanzaro et al., 2014). SERPINB4 expression is up-regulated in hepatocellular carcinoma (Pontisso, 2014).

The gene for SERPINH1 encodes serpin peptidase inhibitor, clade H (heat shock protein 47), member 1, (collagen binding protein 1), a serine proteinase inhibitor. SERPINH1 functions as a collagen-specific molecular chaperone in the endoplasmic reticulum (RefSeq, 2002). SERPINH1 is over-expressed in many human cancers, including stomach cancer, lung cancer, pancreatic ductal adenocarcinoma, glioma, and ulcerative colitis-associated carcinomas (Zhao et al., 2014).

The gene for SEZ6L encodes seizure related 6 homolog (mouse)-like, a transmembrane protein with multiple domains involved in protein-protein interaction and signal transduction (Nishioka et al., 2000). SEZ6L is hypermethylated in gastric cancer (Kang et al., 2008). SEZ6L expression is up-regulated in non-small cell lung cancer and small cell lung cancer cell lines as well as in primary tumor samples compared to normal lung tissues (Gorlov et al., 2007).

The gene for SLC16A3 encodes solute carrier family 16 member 3, a proton-linked monocarboxylate transporter (RefSeq, 2002). Most solid tumors are known to rely on glycolysis for energy production. High rates of glycolysis result in an increased production of lactate which has been associated with poor clinical outcome and direct contribution to tumor growth and progression. SLC16A3 is one of few monocarboxylate transporters which facilitate the lactate export in cancer cells (Dhup et al., 2012; Draoui and Feron, 2011). The SLC16A3 expression has been associated with poor prognosis in hepatocellular cancer patients and increased cell proliferation, migration and invasion in cell line experiments (Gao et al., 2014a). The functional involvement of SLC16A3 in the tumorigenesis was shown in a subset of pancreatic cancer (Baek et al., 2014).

The gene for MTCL1 encodes microtubule crosslinking factor 1. MTCL1 was shown to be involved in the polarity-dependent microtubule remodeling and to mediate the epithelial-cell-specific reorganization of non-centrosomal microtubules through its microtubule-crosslinking activity (Sato et al., 2013).

The gene for SST encodes the pre-pro-protein of the hormone somatostatin. Somatostatin is expressed throughout the body and inhibits the release of numerous secondary hormones. This hormone is an important regulator of the endocrine system through its interactions with pituitary growth hormone, thyroid stimulating hormone, and most hormones of the gastrointestinal tract. Somatostatin also affects rates of neurotransmission in the central nervous system and proliferation of both normal and tumorigenic cells (RefSeq, 2002). SST analogues are successfully used and further investigated as a therapeutic approach in the treatment of gastroenteropancreatic neuroendocrine (carcinoid) tumors, hepatocellular cancer and breast cancer (Pivonello et al., 2014; Culler, 2011; Appetecchia and Baldelli, 2010; Modlin et al., 2010; Watt et al., 2008).

The gene for THY1 is a candidate tumor suppressor gene in nasopharyngeal carcinoma bearing anti-invasive activity (Lung et al., 2010).

The gene for TSC22D4 encodes a protein which is a member of the TSC22 domain family of leucine zipper transcriptional regulators (RefSeq, 2002). Hepatic levels of TSC22D4 were increased in cancer cachexia (Jones et al., 2013).

The gene for TUBA1A encodes tubulin, alpha 1a. The expression of TUBA1A is predominantly found in morphologically differentiated neurologic cells. Mutations in this gene cause lissencephaly type 3 (LIS3)—a neurological condition characterized by microcephaly, mental retardation, and early-onset epilepsy and caused by defective neuronal migration (RefSeq, 2002). De-regulated expression of TUBA1A and some other genes, caused by chromosomal rearrangements in radiation-transformed and tumorigenic breast cell lines, might reflect early molecular events in breast carcinogenesis (Unger et al., 2010). Using comparative proteomic analysis of advanced serous epithelial ovarian carcinoma, TUBA1A was identified as one potential predictor for chemoresistance (Kim et al., 2011).

The gene for TUBA1B encodes tubulin, alpha 1 b (RefSeq, 2002). The differential expression of TUBA1B in combination with the expression of some other genes was associated with prognosis in mantle cell lymphoma, prediction of relapse among patients with stage II colorectal cancer and differentiation between uveal melanomas that subsequently metastasized and those that did not (Blenk et al., 2008; Agesen et al., 2012; Linge et al., 2012). TUBA1B expression was up-regulated in hepatocellular cancer tissues and proliferating hepatocellular cancer cells. An increased TUBA1B expression was associated with poor overall survival and resistance to paclitaxel of hepatocellular cancer patients (Lu et al., 2013a). In ovarian cancer cells, the reduced expression of TUBA1B was associated with oxaliplatin resistance (Tummala et al., 2009).

The gene for TUBA1C encodes tubulin, alpha 1c (RefSeq, 2002). The expression of TUBA1C was shown to be up-regulated in osteosarcoma and HCV-associated hepatocellular cancer and may be a potential biomarker for osteosarcoma tumorigenesis or well-differentiated HCV-associated hepatocellular cancer (Kuramitsu et al., 2011; Li et al., 2010).

The gene for TUBA3C encodes tubulin, alpha 3c (RefSeq, 2002). The gene for TUBA3D encodes tubulin, alpha 3d (RefSeq, 2002). The gene for TUBA4A encodes tubulin, alpha 4a (RefSeq, 2002). The comparative proteomic analysis of esophageal squamous cell carcinoma (ESCC) showed an increased expression of TUBA4A (Qi et al., 2005).

The gene for TUBA8 encodes tubulin, alpha 8. Mutations in TUBA8 are associated with polymicrogyria and optic nerve hypoplasia (RefSeq, 2002). In mouse liver, TUBA8 was induced after treatment with phenobarbital, a non-genotoxic carcinogen. In hepatocellular carcinoma cell lines, the over-expression of TUBA8 was shown to affect cell growth, proliferation and migration (Kamino et al., 2011).

The gene for UCN3 is a member of the sauvagine/corticotropin-releasing factor/urotensin I family. It is structurally related to the corticotropin-releasing factor (CRF) gene and the encoded product is an endogenous ligand for CRF type 2 receptors. In the brain it may be responsible for the effects of stress on appetite (RefSeq, 2002). Ucn3 is produced in normal adrenal and adrenal tumors (both adrenocortical tumors and pheochromocytomas), and acts as an autocrine or paracrine regulator in normal adrenal and adrenal tumors (Takahashi et al., 2006). Urocortin 3 activates AMPK and AKT pathways and enhances glucose disposal in rat skeletal muscle (Roustit et al., 2014).

The gene for VCAN is a member of the aggrecan/versican proteoglycan family. The encoded protein is a large chondroitin sulfate proteoglycan and is a major component of the extracellular matrix. This protein is involved in cell adhesion, proliferation, migration and angiogenesis and plays a central role in tissue morphogenesis and maintenance (RefSeq, 2002). VCAN expression was regulated in cancer-associated fibroblasts through TGF-beta receptor type II and SMAD signaling. up-regulated VCAN promoted the motility and invasion of ovarian cancer cells by activating the NF-kappaB signaling pathway and by up-regulating expression of CD44, matrix metalloproteinase-9, and the hyaluronan-mediated motility receptor (Yeung et al., 2013). A collagen-remodeling gene signature including VCAN regulated by TGF-beta signaling is associated with metastasis and poor survival in serous ovarian cancer (Cheon et al., 2014). VCAN is significantly up-regulated in CRC comparing paired samples of healthy colon mucosa and tumor tissues of 53 patients (Pitule et al., 2013).

The gene for WNT16, wingless-type MMTV integration site family, member 16 encodes a secreted signaling protein which is implicated in oncogenesis and in several developmental processes, including regulation of cell fate and patterning during embryogenesis (RefSeq, 2002). The expression of WNT16 was shown to be up-regulated in t (1; 19) chromosomal translocation-containing acute lymphoblastoid leukemia (ALL) and play an important role in leukemogenesis (Casagrande et al., 2006; Mazieres et al., 2005). A study of ALL cell lines and samples from patients with ALL showed that the up-regulation of WNT16 and few other Wnt target genes was caused by the methylation of Wnt inhibitors which was further associated with significantly decreased 10-year disease-free survival and overall survival (Roman-Gomez et al., 2007).

The gene for WNT5A belongs to the WNT gene family that consists of structurally related genes which encode secreted signaling proteins. These proteins have been implicated in oncogenesis and in several developmental processes, including regulation of cell fate and patterning during embryogenesis. The WNT5A gene encodes a member of the WNT family that signals through both the canonical and non-canonical WNT pathways. This protein is a ligand for the seven transmembrane receptor frizzled-5 and the tyrosine kinase orphan receptor 2. This protein plays an essential role in regulating developmental pathways during embryogenesis. This protein may also play a role in oncogenesis (RefSeq, 2002). WNT5A is over-expressed in CRC and had a concordance rate of 76% between the primary tumor and metastatic site (Lee et al., 2014). WNT5A is up-regulated and a key regulator of the epithelial-to-mesenchymal transition and metastasis in human gastric carcinoma cells, nasopharyngeal carcinoma and pancreatic cancer (Kanzawa et al., 2013; Zhu et al., 2014; Bo et al., 2013).

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14 or longer, and in case of MHC class II peptides (elongated variants of the peptides of the invention) they can be as long as 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 5

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1-Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |

TABLE 5-continued

Expression frequencies F of HLA-A*02 and HLA-A*24
and the most frequent HLA-DR serotypes. Frequencies are
deduced from haplotype frequencies Gf within the
American population adapted from Mori et al. (Mori et al., 1997)
employing the Hardy-Weinberg formula $F = 1 - (1-Gf)^2$. Combinations
of A*02 or A*24 with certain HLA-DR alleles might be enriched or less
frequent than expected from their single frequencies due to linkage
disequilibrium. For details refer to Chanock et al. (Chanock et al., 2004).

| Allele | Population | Calculated phenotype from allele frequency |
|---|---|---|
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid (s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein
  (i) each base or amino acid in the Reference Sequence that does not have a corresponding aligned base or amino acid in the Compared Sequence and
  (ii) each gap in the Reference Sequence and
  (iii) each aligned base or amino acid in the Reference Sequence that is different from an aligned base or amino acid in the Compared Sequence, constitutes a difference and
  (iiii) the alignment has to start at position 1 of the aligned sequences;
and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 67 or a variant thereof which is 88% homologous to SEQ ID NO: 1 to SEQ ID NO: 67, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 67. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 67, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or —II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the T-cell receptor can be modified by replacement with other amino acids whose incorporation do not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 6

Variants and motif of the peptides according to SEQ ID NO: 4, 29, and 30.

| Position | 1 | 2 | 3 | 4 | 5 | 6 | 7 | 8 | 9 |
|---|---|---|---|---|---|---|---|---|---|
| SEQ ID NO. 4 | S | V | D | V | S | P | P | K | V |
| Variants |   |   |   |   |   |   |   |   | I |
|   |   |   |   |   |   |   |   |   | L |
|   |   |   |   |   |   |   |   |   | A |
|   |   |   | L |   |   |   |   |   | I |
|   |   |   | L |   |   |   |   |   | L |
|   |   |   | L |   |   |   |   |   |   |
|   |   |   | L |   |   |   |   |   | A |
|   |   |   | A |   |   |   |   |   | I |
|   |   |   | A |   |   |   |   |   | L |
|   |   |   | A |   |   |   |   |   |   |
|   |   |   | A |   |   |   |   |   | A |
|   |   |   |   |   |   |   |   | M | I |
|   |   |   |   |   |   |   |   | M | L |
|   |   |   |   |   |   |   |   | M |   |
|   |   |   |   |   |   |   |   | M | A |
|   |   |   |   |   |   |   |   | T | I |
|   |   |   |   |   |   |   |   | T | L |
|   |   |   |   |   |   |   |   | T |   |
|   |   |   |   |   |   |   |   | T | A |
|   |   |   |   |   |   |   |   | Q | I |
|   |   |   |   |   |   |   |   | Q | L |

TABLE 6-continued

Variants and motif of the peptides according to SEQ ID NO: 4, 29, and 30.

| Position | 1 | 2 | 3 | 4 | 5 | 6 | 7 | 8 | 9 |
|---|---|---|---|---|---|---|---|---|---|
|  |  | Q |  |  |  |  |  |  |  |
|  |  | Q |  |  |  |  |  |  | A |
| SEQ ID NO. 29 | F | L | Q | E | Y | L | D | A | I |
| Variants |  | I |  |  |  |  |  |  | L |
|  |  | I |  |  |  |  |  |  | V |
|  |  | I |  |  |  |  |  |  |  |
|  |  | I |  |  |  |  |  |  | A |
|  |  | M |  |  |  |  |  |  | L |
|  |  | M |  |  |  |  |  |  | V |
|  |  | M |  |  |  |  |  |  |  |
|  |  | M |  |  |  |  |  |  | A |
|  |  | A |  |  |  |  |  |  | L |
|  |  | A |  |  |  |  |  |  | V |
|  |  | A |  |  |  |  |  |  |  |
|  |  | A |  |  |  |  |  |  | A |
|  |  | V |  |  |  |  |  |  | L |
|  |  | V |  |  |  |  |  |  | V |
|  |  | V |  |  |  |  |  |  |  |
|  |  | V |  |  |  |  |  |  | A |
|  |  | T |  |  |  |  |  |  | L |
|  |  | T |  |  |  |  |  |  | V |
|  |  | T |  |  |  |  |  |  |  |
|  |  | T |  |  |  |  |  |  | A |
|  |  | Q |  |  |  |  |  |  | L |
|  |  | Q |  |  |  |  |  |  | V |
|  |  | Q |  |  |  |  |  |  |  |
|  |  | Q |  |  |  |  |  |  | A |
| SEQ ID NO. 30 | V | V | D | E | G | P | T | G | V |
| Variants |  |  |  |  |  |  |  |  | L |
|  |  |  |  |  |  |  |  |  | I |
|  |  |  |  |  |  |  |  |  | A |
|  |  | M |  |  |  |  |  |  | L |
|  |  | M |  |  |  |  |  |  | I |
|  |  | M |  |  |  |  |  |  |  |
|  |  | M |  |  |  |  |  |  | A |
|  |  | L |  |  |  |  |  |  | L |
|  |  | L |  |  |  |  |  |  | I |
|  |  | L |  |  |  |  |  |  |  |
|  |  | L |  |  |  |  |  |  | A |
|  |  | A |  |  |  |  |  |  | L |
|  |  | A |  |  |  |  |  |  | I |
|  |  | A |  |  |  |  |  |  |  |
|  |  | A |  |  |  |  |  |  | A |
|  |  | T |  |  |  |  |  |  | L |
|  |  | T |  |  |  |  |  |  | I |
|  |  | T |  |  |  |  |  |  |  |
|  |  | T |  |  |  |  |  |  | A |
|  |  | Q |  |  |  |  |  |  | L |
|  |  | Q |  |  |  |  |  |  | I |
|  |  | Q |  |  |  |  |  |  |  |
|  |  | Q |  |  |  |  |  |  | A |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |
| N-terminus | C-terminus |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid (s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 μM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 67.

"Consisting essentially of" shall mean that a peptide according to the present invention, in addition to the sequence according to any of SEQ ID NO: 1 to SEQ ID NO 67 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from pancreatic cancer samples (N=18 A*02-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 18 pancreatic cancer patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from pancreatic cancer tissue samples were purified and HLA-associated peptides were isolated and analyzed by LC-MS (see examples). All TUMAPs contained in the present application were identified with this approach on primary pancreatic cancer samples confirming their presentation on primary pancreatic cancer.

TUMAPs identified on multiple pancreatic cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

The present invention provides peptides that are useful in treating cancers/tumors, preferably pancreatic cancer that over- or exclusively present the peptides of the invention. These peptides were shown by mass spectrometry to be naturally presented by HLA molecules on primary human pancreatic cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy pancreas cells or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from pancreatic cancer, but not on normal tissues (see Example 1).

HLA-bound peptides can be recognized by the immune system, specifically T lymphocytes. T cells can destroy the cells presenting the recognized HLA/peptide complex, e.g. pancreatic cancer cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutics such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 67, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide (s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide (s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly (lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly (I:C) and derivates thereof (e.g. AmpliGen®, Hiltonol®, poly-(ICLC), poly (IC-R), poly (I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex (es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 67, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 67, or a variant thereof which is at least 88% homologous (preferably identical) to SEQ ID NO: 1 to SEQ ID NO: 67 or a variant thereof that induces T cells cross-reacting with said peptide, wherein said peptide is not the underlying full-length polypeptide The present invention further relates to a peptide comprising a sequence that is selected from the group consisting of SEQ ID NO: 1 to SEQ ID NO: 67 or a variant thereof which is at least 88% homologous (preferably identical) to SEQ ID NO: 1 to SEQ ID NO: 67, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 67.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of pancreatic cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 67 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are pancreatic cancer cells or other solid or hematological tumor cells such as pancreatic cancer, brain cancer, kidney cancer, colon or rectal cancer, leukemia.

The present invention further relates to particular marker proteins and biomarkers based on the peptides according to the present invention, herein called "targets" that can be used in the diagnosis and/or prognosis of pancreatic cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a pancreatic cancer marker (poly)peptide, delivery of a toxin to a pancreatic cancer cell expressing a cancer marker gene at an increased level, and/or inhibiting the activity of a pancreatic cancer marker polypeptide) according to the invention.

Whenever possible, the antibodies of the invention may be purchased from commercial sources. The antibodies of the invention may also be generated using well-known methods. The skilled artisan will understand that either full length pancreatic cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 67 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the pancreatic cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F (ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (µg/kg to up to 100 mg/kg of body weight or more per day, depending on the factors mentioned above. Following administration of an antibody, preferably for treating pancreatic cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^3$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than $1 \times 10$ µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 67, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively eliciting high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, and vaccinia-infected target cells.

In addition plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 67.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule (s) of the invention or (a) known molecule (s).

The present invention further provides a medicament that is useful in treating cancer, in particular pancreatic cancer and other malignancies.

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from pancreatic cancer, the medicament of the invention is preferably used to treat pancreatic cancer.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of pancreatic cancer patients with various HLA-A HLA-B and HLA-C alleles. It may contain MHC class I and MHC class II peptides or elongated MHC class I peptides. In addition to the tumor associated peptides collected from several pancreatic cancer tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®)). The approach assures that only TUMAPs truly present on a high percentage of tumors but not or only minimally expressed on normal tissue, are chosen for further analysis. For initial peptide selection, pancreatic cancer samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue (pancreatic cancer) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from pancreatic cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 μm sterile filter. The final bulk solution is obtained.

Final bulk solution is filled into vials and stored at −20° C. until use. One vial contains 700 μL solution, containing 0.578 mg of each peptide. Of this, 500 μL (approx. 400 μg per peptide) will be applied for intradermal injection.

In addition to being useful for treating cancer, the peptides of the present invention are also useful as diagnostics. Since the peptides were generated from pancreatic cancer cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for pancreatic cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying Figures, nevertheless, without being limited thereto. For the purposes of the present invention, all references as cited herein are incorporated by reference in their entireties.

Figure 1B:
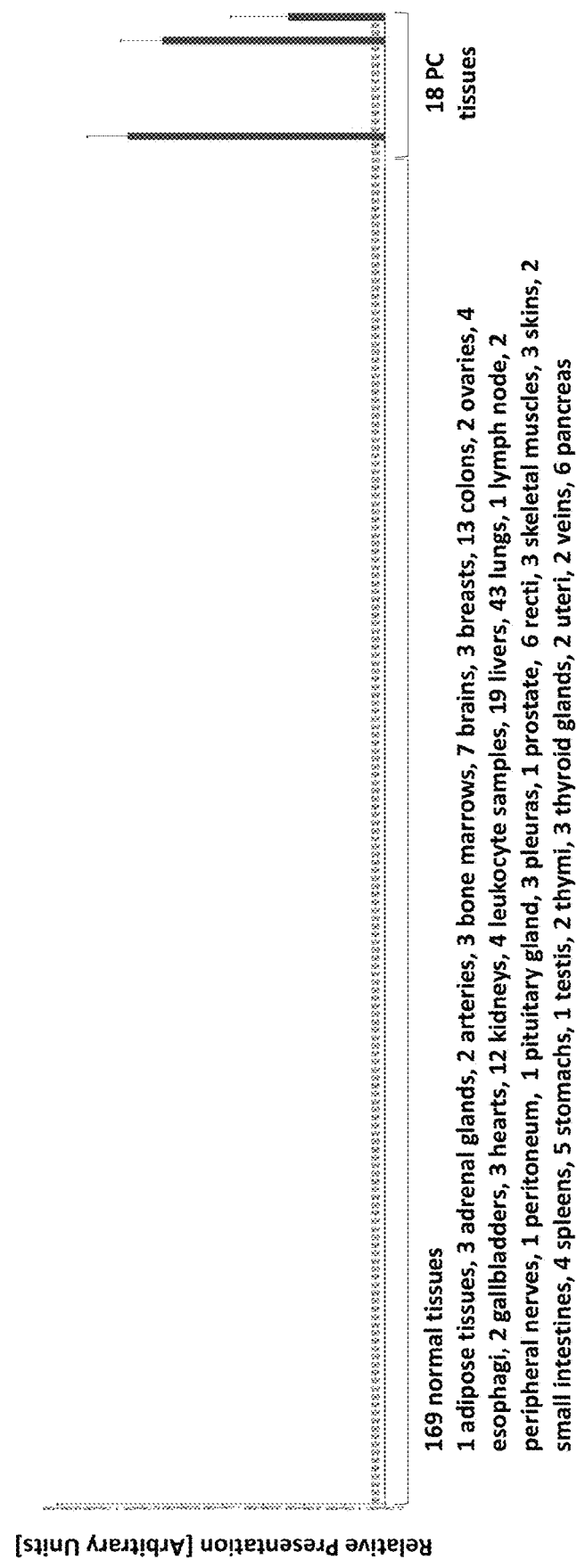
Figure 1C:
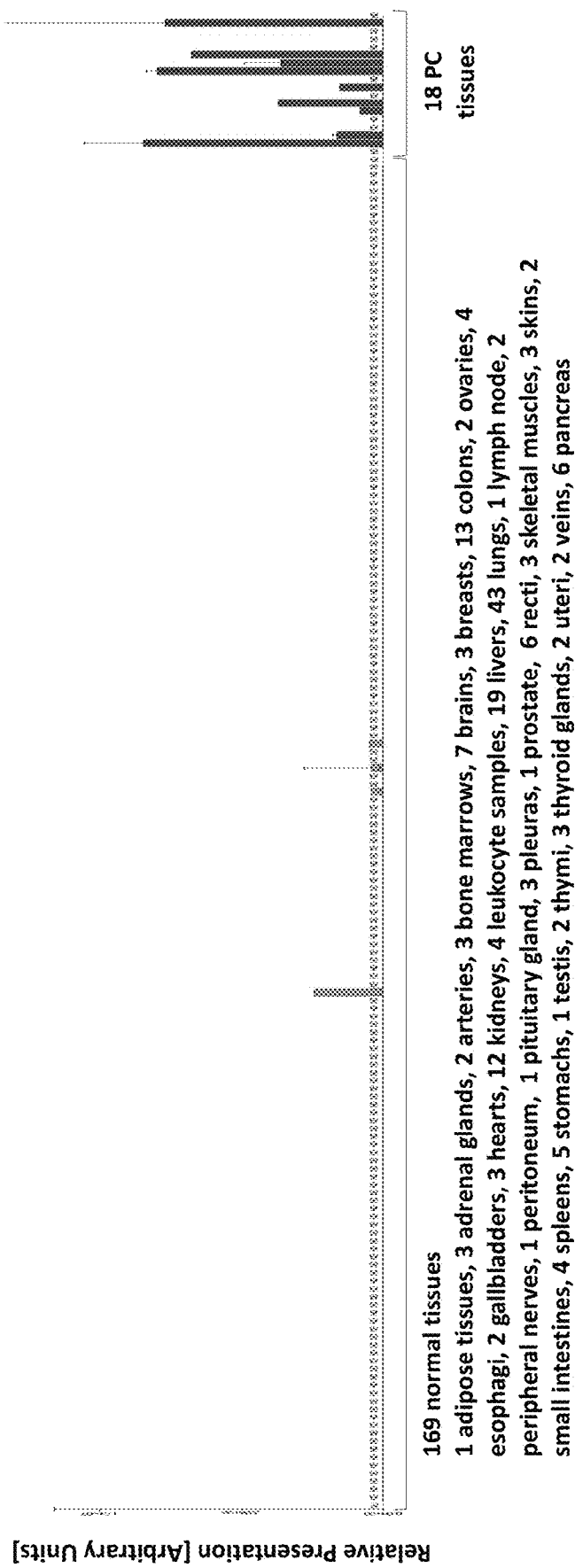

FIGS. 1A-1C shows the over-presentation of various peptides in normal tissues (dark gray) and pancreatic cancer (light gray). FIG. 1D shows all cell lines (dark gray), normal tissues (gray) and cancers tissues (light gray) where the exemplary peptide (FLFDGSANLV) (SEQ ID NO.: 9) has been detected. FIG. 1A) Gene: CTLA/CTLB, Peptide: FLAQQESEI (A*02) (SEQ ID NO.: 1); Tissues shown from left to right: 1 adipose tissues, 3 adrenal glands, 2 arteries, 3 bone marrows, 7 brains, 3 breasts, 13 colons, 1 ovary, 4 esophagi, 2 gallbladders, 3 hearts, 12 kidneys, 4 leukocyte samples, 19 livers, 43 lungs, 1 lymph node, 1 ovary, 2 peripheral nerves, 1 peritoneum, 1 pituitary gland, 3 pleuras, 1 prostate, 6 recti, 3 skeletal muscles, 3 skins, 2 small intestines, 4 spleens, 5 stomachs, 1 testis, 2 thymi, 3 thyroid glands, 2 uteri, 2 veins, 6 pancreas, 18 pancreatic cancers; FIG. 1B) Gene: PLEC, Peptide: SLQEEHVAVA (A*02), (SEQ ID NO.: 2); Tissues shown from left to right: 1 adipose tissues, 3 adrenal glands, 2 arteries, 3 bone marrows, 7 brains, 3 breasts, 13 colons, 1 ovary, 4 esophagi, 2 gallbladders, 3 hearts, 12 kidneys, 4 leukocyte samples, 19 livers, 43 lungs, 1 lymph node, 1 ovary, 2 peripheral nerves, 1 peritoneum, 1 pituitary gland, 3 pleuras, 1 prostate, 6 recti, 3 skeletal muscles, 3 skins, 2 small intestines, 4 spleens, 5 stomachs, 1 testis, 2 thymi, 3 thyroid glands, 2 uteri, 2 veins, 6 pancreas, 18 pancreatic cancers; FIG. 1C) Gene: COL6A3, Peptide: FLVDGSSAL (A*02) (SEQ ID NO.: 10); Tissues shown from left to right: 1 adipose tissues, 3 adrenal glands, 2 arteries, 3 bone marrows, 7 brains, 3 breasts, 13 colons, 1 ovary, 4 esophagi, 2 gallbladders, 3 hearts, 12 kidneys, 4 leukocyte samples, 19 livers, 43 lungs, 1 lymph node, 1 ovary, 2 peripheral nerves, 1 peritoneum, 1 pituitary gland, 3 pleuras, 1 prostate, 6 recti, 3 skeletal muscles, 3 skins, 2 small intestines, 4 spleens, 5 stomachs, 1 testis, 2 thymi, 3 thyroid glands, 2 uteri, 2 veins, 6 pancreas, 18 pancreatic cancers; FIG. 1D) COL6A3, Peptide: FLFDGSANLV (A*02) (SEQ ID NO.: 9); Tissues shown from left to right: 5 pancreatic cancer cell lines, 7 normal tissues (1 colon, 6 lungs), 85 cancer tissues (2 breast cancers, 6 colon cancers, 4 esophageal cancers, 3 liver cancers, 56 lung cancers, 5 pancreatic cancers, 3 rectal cancers, 1 melanoma, 5 gastric cancers). The set of normal tissues was the same as in A-C, but tissues without detection are not shown. Discrepancies regarding the list of tumor types between FIG. 1D and table 4 might be due to the more stringent selection criteria applied in table 4 (for details please refer to table 4). FIG. 1D shows all samples with detectable presentation of the peptide Y, regardless of over-presentation parameters and technical sample quality check.

Figure 1F:
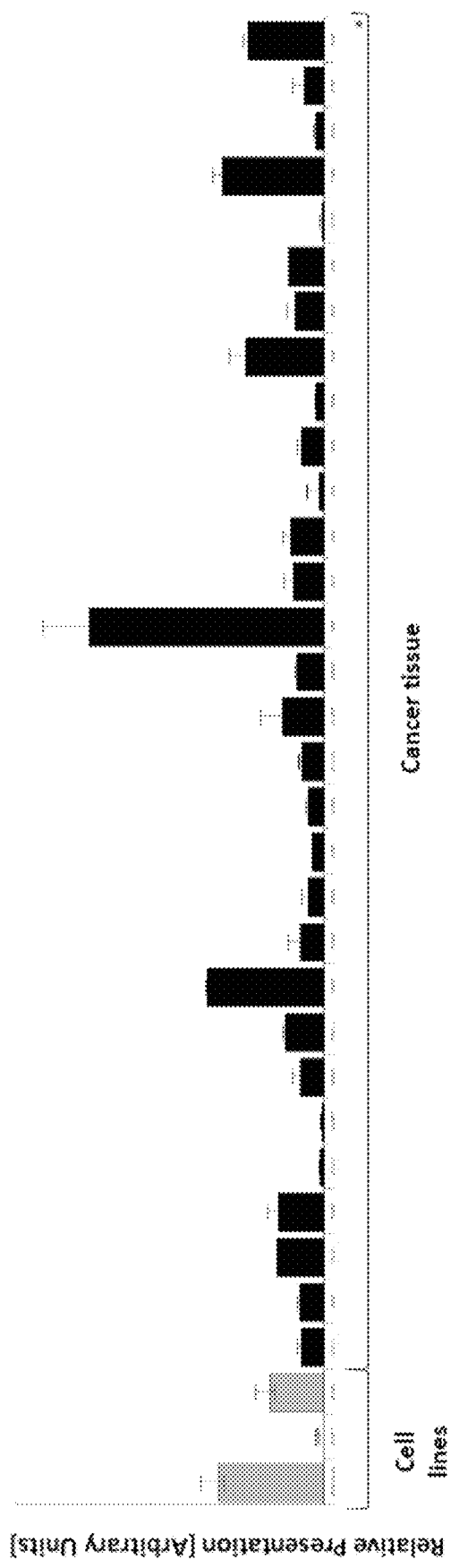
Figure 1H:
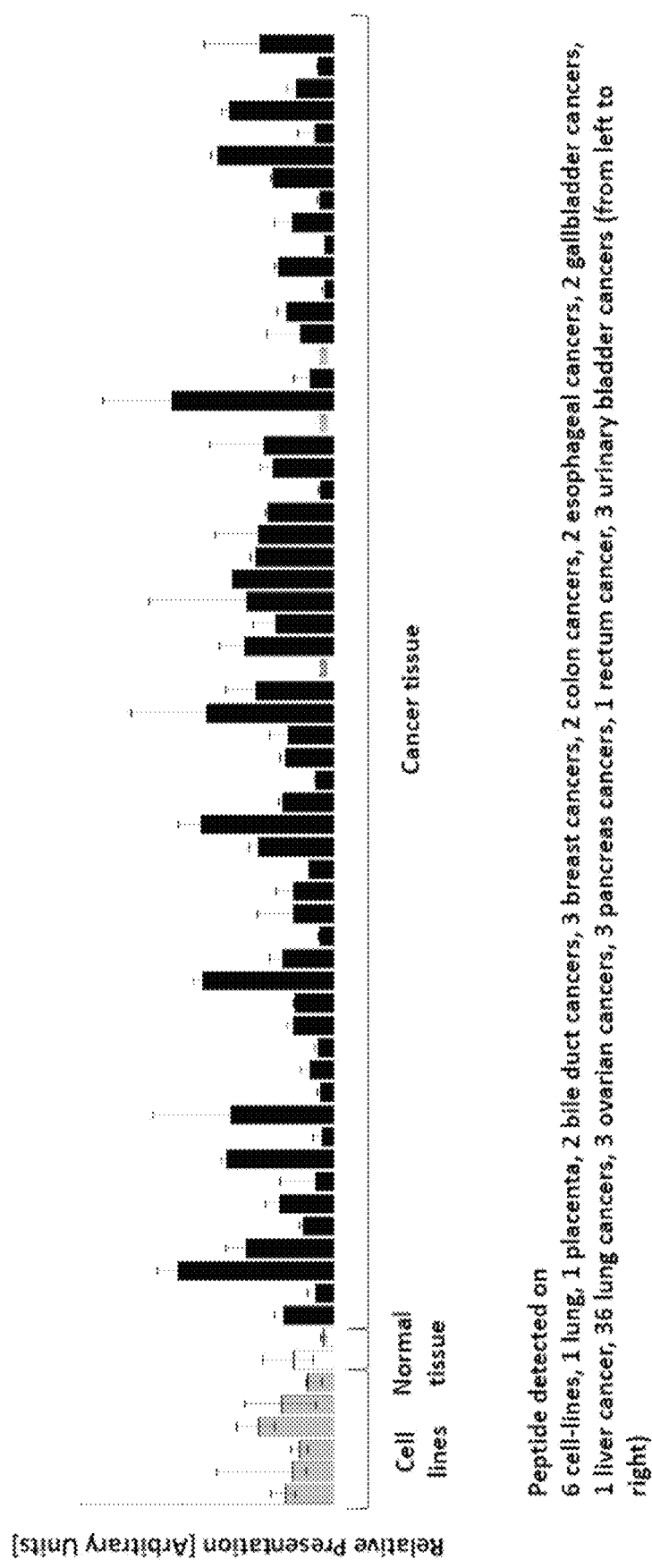

FIGS. 1E-1I show all cell lines (dark gray), normal tissues (gray) and cancers tissues (light gray) where the exemplary peptides have been detected. FIG. 1E) Peptide: SVDVSPPKV (A*02) (SEQ ID NO.: 4); Tissues shown from left to right: 1 cell-lines, 3 primary cultures, 1 skin, 1 bile duct cancer, 3 brain cancers, 1 breast cancer, 4 esophageal cancers, 5 kidney cancers, 11 lung cancers, 1 lymph node cancer, 1 ovarian cancer, 3 pancreas cancers, 1 prostate cancer, 3 skin cancers, 2 urinary bladder cancers, 3 uterus cancers; FIG. 1F) Peptide: LLVDDSFLHTV (A*02) (SEQ ID NO.: 5); Tissues shown from left to right: 2 cell-lines, 1 primary culture, 1 bile duct cancer, 2 brain cancers, 1 breast cancer, 3 esophageal cancers, 2 gallbladder cancers, 2 kidney cancers, 2 liver cancers, 3 lung cancers, 7 ovarian cancers, 2 pancreas cancers, 3 skin cancers, 1 stomach cancer, 1 uterus cancer, FIG. 1G) Peptide: IVDDLTINL (A*02) (SEQ ID NO.: 8); Tissues shown from left to right: 1 cell-line, 1 colon cancer, 2 esophageal cancers, 2 gallbladder cancers, 5 lung cancers, 1 lymph node cancer, 1 pancreas cancer, 2 skin cancers, 4 stomach cancers, 1 urinary bladder cancer, 4 uterus cancers, FIG. 1H) Peptide: LLAGQTYHV (A*02) (SEQ ID NO.: 13); Tissues shown from left to right: 6 cell-lines, 1 lung, 1 placenta, 2 bile duct cancers, 3 breast cancers, 2 colon cancers, 2 esophageal cancers, 2 gallbladder cancers, 1 liver cancer, 36 lung cancers, 3 ovarian cancers, 3 pancreas cancers, 1 rectum cancer, 3 urinary bladder cancers; and FIG. 1I) Peptide: VLAKPGVISV (A*02) (SEQ ID NO.: 14); Tissues shown from left to right: 7 cell-lines, 1 lung, 1 bile duct cancer, 4 breast cancers, 1 colon cancer, 2 esophageal cancers, 1 gallbladder cancer, 36 lung cancers, 1 ovarian cancer, 3 pancreas cancers, 2 rectum cancers, 1 stomach cancer, 1 urinary bladder cancer.

FIGS. 2A-2C shows exemplary expression profiles (relative expression compared to normal kidney) of source genes of the present invention that are highly over-expressed or exclusively expressed in pancreatic cancer in a panel of normal tissues (dark gray) and 11 pancreatic cancer samples (gray). FIG. 2A) LAMC2; Tissues from left to right: 1 adrenal gland, 1 artery, 1 bone marrow, 1 brain (whole), 1 breast, 1 colon, 1 esophagus, 1 heart, 3 kidneys, 1 leukocyte sample, 1 liver, 1 lung, 1 lymph node, 1 ovary, 1 pancreas, 1 placenta, 1 prostate, 1 salivary gland, 1 skeletal muscle, 1 skin, 1 small intestine, 1 spleen, 1 stomach, 1 testis, 1 thymus, 1 thyroid gland, 1 urinary bladder, 1 uterine cervix, 1 uterus, 1 vein, 18 pancreatic cancers; FIG. 2B) VCAN; Tissues from left to right: 1 adrenal gland, 1 artery, 1 bone marrow, 1 brain (whole), 1 breast, 1 colon, 1 esophagus, 1 heart, 3 kidneys, 1 leukocyte sample, 1 liver, 1 lung, 1 lymph node, 1 ovary, 1 pancreas, 1 placenta, 1 prostate, 1 salivary gland, 1 skeletal muscle, 1 skin, 1 small intestine, 1 spleen, 1 stomach, 1 testis, 1 thymus, 1 thyroid gland, 1 urinary bladder, 1 uterine cervix, 1 uterus, 1 vein, 18 pancreatic cancers; FIG. 2C) FAP; Tissues from left to right: 1 adrenal gland, 1 artery, 1 bone marrow, 1 brain (whole), 1 breast, 1 colon, 1 esophagus, 1 heart, 3 kidneys, 1 leukocyte sample, 1 liver, 1 lung, 1 lymph node, 1 ovary, 1 pancreas, 1 placenta, 1 prostate, 1 salivary gland, 1 skeletal muscle, 1 skin, 1 small intestine, 1 spleen, 1 stomach, 1 testis, 1 thymus, 1 thyroid gland, 1 urinary bladder, 1 uterine cervix, 1 uterus, 1 vein, 18 pancreatic cancers.

Figure 3A:
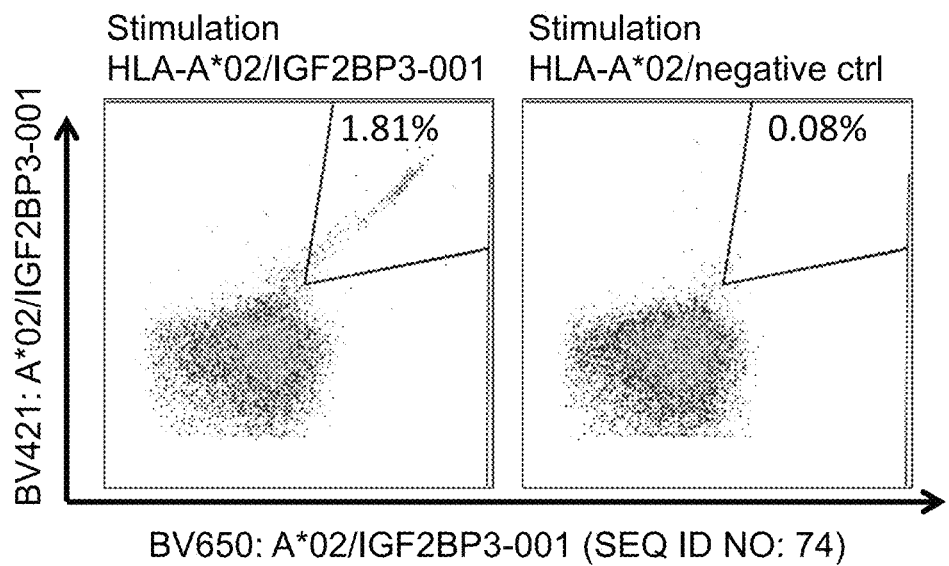
Figure 3B:
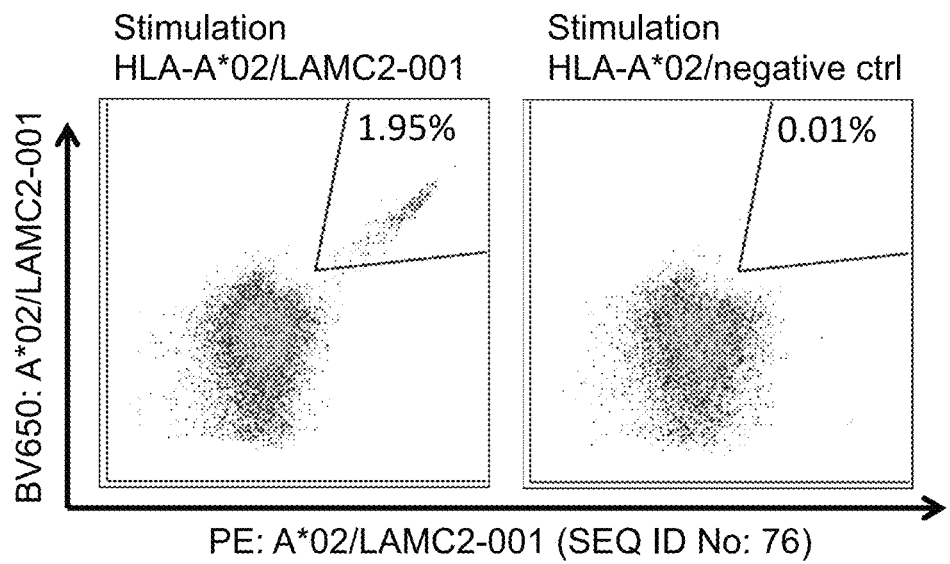
Figure 3C:
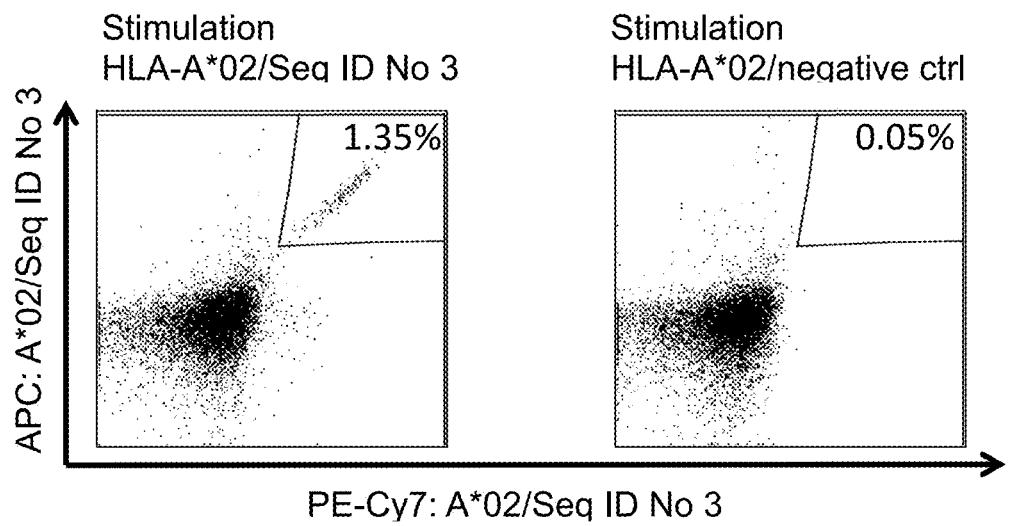
Figure 3D:
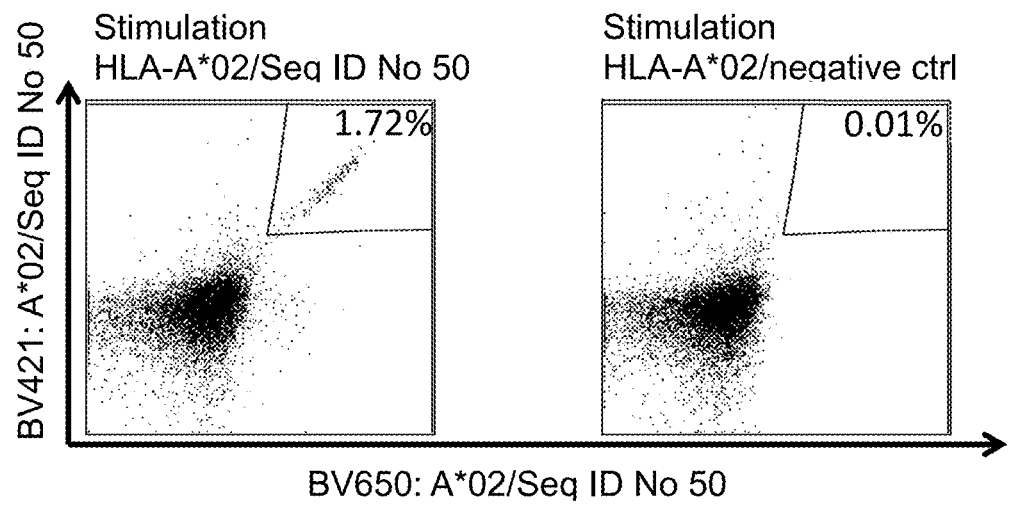

FIGS. 3A-3D shows exemplary immunogenicity data: flow cytometry results after peptide-specific multimer staining. FIGS. 3C and 3D show exemplary results of peptide-specific in vitro CD8+ T cell responses of a healthy HLA-A*02+ donor. CD8+ T cells were primed using artificial APCs coated with anti-CD28 mAb and HLA-A*02 in complex with SeqID No 3 peptide (FIG. 3C, left panel) or Seq ID No 50 peptide (FIG. 3D, left panel), respectively. After three cycles of stimulation, the detection of peptide-reactive cells was performed by 2D multimer staining with A*02/Seq ID No 3 (FIG. 3C) or A*02/Seq ID No 50 (FIG. 3D). Right panels (FIGS. 3C and 3D) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

EXAMPLES

Example 1: Identification and Quantitation of Tumor Associated Peptides Presented on the Cell Surface Tissue Samples Patients' tumor tissues were obtained from Asterand (Detroit, USA and Royston, Herts, UK); Geneticist Inc. (Glendale, Calif., USA); Hospital of Heidelberg; University Hospital of Tübingen. Normal tissues were obtained from Bio-Options Inc. (CA, USA); BioServe (Beltsville, Md., USA); Capital BioScience Inc. (Rockville, Md., USA); Geneticist Inc. (Glendale, Calif., USA); University Hospital of Geneva; University Hospital of Heidelberg; Kyoto Prefectural University of Medicine (KPUM); University Hospital Munich; ProteoGenex Inc. (Culver City, Calif., USA); University Hospital of Tübingen. Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, -B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOPS strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose pancreatic cancer samples to a baseline of normal tissue samples. Presentation profiles of exemplary over-presented peptides are shown in FIGS. 2A-2C. Presentation scores for exemplary peptides are shown in Table 8.

TABLE 8

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+).

| SEQ ID No. | Sequence | Peptide Presentation |
|---|---|---|
| 1 | FLAQQESEI | +++ |
| 2 | SLQEEHVAVA | ++ |
| 3 | ALLTFMEQV | +++ |
| 4 | SVDVSPPKV | + |
| 5 | LLVDDSFLHTV | +++ |
| 7 | AQQESEIAGI | +++ |
| 8 | IVDDLTINL | +++ |
| 9 | FLFDGSANLV | +++ |
| 10 | FLVDGSSAL | +++ |
| 11 | FLYKIIDEL | +++ |
| 12 | FVSEIVDTV | +++ |
| 13 | LLAGQTYHV | ++ |
| 14 | VLAKPGVISV | + |
| 15 | SLANNVTSV | + |
| 16 | APVNVTTEVKSV | +++ |
| 17 | FLKSGDAAIV | +++ |
| 18 | SLLDDELMSL | ++ |
| 19 | HLAPETDEDDL | +++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+).

| SEQ ID No. | Sequence | Peptide Presentation |
|---|---|---|
| 20 | RLAGDGVGAV | ++ |
| 21 | HLMDQPLSV | +++ |
| 23 | SLSAFTLFL | + |
| 24 | GLLEELVTV | +++ |
| 25 | SLKEEVGEEAI | + |
| 26 | SLKEEVGEEAIV | ++ |
| 29 | FLQEYLDAI | +++ |
| 31 | SLAAAAGKQEL | +++ |
| 32 | SLAAAAGKQELA | +++ |
| 33 | SLDSRLELA | +++ |
| 34 | MLMPVHFLL | +++ |
| 35 | VMDSGDGVTHTV | + |
| 36 | KQEYDESGPSIVH | +++ |
| 37 | GLLKKINSV | +++ |
| 38 | NLVEKTPALV | +++ |
| 39 | TLLSNLEEA | + |
| 40 | FILDSAETTTL | +++ |
| 41 | FLLDGSEGV | +++ |
| 42 | KLVDKSTEL | +++ |
| 43 | RLDQRVPQI | ++ |
| 46 | TFAPVNVTTEVKSV | + |
| 47 | KMDASLGNLFA | +++ |
| 48 | ALTQTGGPHV | +++ |
| 49 | NLKGTFATL | +++ |
| 50 | ALAAILTRL | +++ |
| 51 | ALMLQGVDL | +++ |
| 52 | RMVEEIGVEL | ++ |
| 56 | GLLDYATGAIGSV | +++ |
| 57 | FLGKVVIDV | +++ |
| 58 | GLAAFKAFL | +++ |
| 59 | KLFNLSKEDDV | +++ |
| 61 | ALEKDYEEVGV | +++ |
| 62 | ALEKDYEEV | +++ |
| 63 | FAGDDAPR | +++ |
| 64 | FLVSNMLLAEA | +++ |
| 66 | ALLSGLREA | +++ |
| 67 | KMFFLIDKV | +++ |
| 68 | KLLTEVHAA | +++ |
| 70 | FLVDGSWSV | +++ |
| 71 | FLLDGSANV | +++ |
| 74 | KIQEILTQV | +++ |
| 75 | RLDDLKMTV | ++ |
| 76 | RLLDSVSRL | + |
| 77 | GLTDNIHLV | +++ |
| 79 | VLAPRVLRA | + |
| 80 | TLYPHTSQV | + |
| 81 | AMSSKFFLV | +++ |
| 82 | SISDVIAQV | +++ |
| 83 | FLIDSSEGV | +++ |
| 84 | NLLDLDYEL | +++ |
| 85 | TVAEVIQSV | ++ |
| 86 | SLLAQNTSWLL | ++ |
| 87 | LLLGSPAAA | +++ |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immuno-therapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; Bio-Chain, Hayward, Calif., USA). The RNA from several individuals (between 2 and 123 individuals) was mixed such that RNA from each individual was equally weighted.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 μg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal kidney sample was arbitrarily set to 1.0. Exemplary expression profiles of source genes of the present invention that are highly over-expressed or exclusively expressed in pancreatic cancer are shown in FIGS. 1A-1I. Expression scores for further exemplary genes are shown in Table 9.

TABLE 9

Expression scores. The table lists peptides from genes that are very highly overexpressed in tumors compared to a panel of normal tissues (+++), highly overexpressed in tumors compared to a panel of normal tissues (++) or overexpressed in tumors compared to a panel of normal tissues (+).

| SEQ ID No | Sequence | Gene Expression |
|---|---|---|
| 3 | ALLTFMEQV | ++ |
| 4 | SVDVSPPKV | + |
| 6 | VLISLKQAPLV | + |
| 13 | LLAGQTYHV | + |
| 15 | SLANNVTSV | + |
| 16 | APVNVTTEVKSV | + |
| 20 | RLAGDGVGAV | + |
| 23 | SLSAFTLFL | + |

TABLE 9-continued

Expression scores. The table lists peptides from genes that are very highly overexpressed in tumors compared to a panel of normal tissues (+++), highly overexpressed in tumors compared to a panel of normal tissues (++) or overexpressed in tumors compared to a panel of normal tissues (+).

| SEQ ID No | Sequence | Gene Expression |
|---|---|---|
| 25 | SLKEEVGEEAI | ++ |
| 27 | YLQGQRLDNV | + |
| 30 | VVDEGPTGV | ++ |
| 36 | KQEYDESGPSIVH | + |
| 43 | RLDQRVPQI | + |
| 44 | VLLDKIKNLQV | + |
| 46 | TFAPVNVTTEVKSV | ++ |
| 47 | KMDASLGNLFA | + |
| 48 | ALTQTGGPHV | + |
| 50 | ALAAILTRL | +++ |
| 51 | ALMLQGVDL | ++ |
| 52 | RMVEEIGVEL | + |
| 57 | FLGKVVIDV | + |
| 58 | GLAAFKAFL | + |
| 59 | KLFNLSKEDDV | + |
| 61 | ALEKDYEEVGV | +++ |
| 62 | ALEKDYEEV | +++ |
| 66 | ALLSGLREA | ++ |
| 67 | KMFFLIDKV | + |
| 71 | FLLDGSANV | + |
| 73 | TLVAIVVGV | ++ |
| 75 | RLDDLKMTV | ++ |
| 76 | RLLDSVSRL | +++ |
| 78 | TLSSIKVEV | +++ |
| 81 | AMSSKFFLV | ++ |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for 22 HLA-A*0201 restricted TUMAPs of the invention so far, demonstrating that these peptides are T-cell epitopes against which CD8+ precursor T cells exist in humans (Table 10).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO 88) from modified Melan-A/MART-1) and A*0201/DDX5-001 (YLLPAIVHI (SEQ ID No. 89) from DDX5), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Pancreatic Cancer Peptides

For tested HLA class I peptides, in vitro immunogenicity could be demonstrated by generation of peptide specific T-cell lines. Exemplary flow cytometry results after TUMAP-specific multimer staining for 2 peptides of the invention are shown in FIGS. 3A-3D together with corresponding negative controls. Results for 2 peptides from the invention are summarized in Table 10.

TABLE 10 in vitro immunogenicity of HLA class I peptides of the invention
Exemplary results of in vitro immunogenicity experiments conducted by the applicant for the peptides of the invention.

| Seq ID | wells | donors |
|---|---|---|
| 69 | ++ | ++++ |
| 87 | + | +++ |

<20% = +; 20%-49% = ++; 50%-69% = +++; > = 70% = ++++

Results for 7 additional peptides from the invention are summarized in Table 10B.

TABLE 10B in vitro immunogenicity of HLA class I peptides of the invention. Exemplary results of in vitro immunogenicity experiments conducted by the applicant for the peptides of the invention.

| Seq ID No | Sequence | Wells positive [%] |
|---|---|---|
| 3 | ALLTFMEQV | ++ |
| 20 | RLAGDGVGAV | ++++ |
| 21 | HLMDQPLSV | + |
| 23 | SLSAFTLFL | ++ |
| 34 | MLMPVHFLL | + |
| 37 | GLLKKINSV | + |
| 50 | ALAAILTRL | +++ |

<20% = +; 20%-49% = ++; 50%-69% = +++; > = 70% = ++++

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 11

MHC class I binding scores.

| SEQ ID No | Sequence | Peptide exchange |
|---|---|---|
| 1 | FLAQQESEI | ++ |
| 2 | SLQEEHVAVA | ++ |
| 3 | ALLTFMEQV | +++ |
| 4 | SVDVSPPKV | ++ |
| 5 | LLVDDSFLHTV | +++ |
| 6 | VLISLKQAPLV | ++ |
| 7 | AQQESEIAGI | ++ |
| 8 | IVDDLTINL | ++ |
| 9 | FLFDGSANLV | ++ |
| 10 | FLVDGSSAL | ++ |
| 11 | FLYKIIDEL | +++ |
| 12 | FVSEIVDTV | +++ |
| 13 | LLAGQTYHV | ++ |
| 14 | VLAKPGVISV | ++ |
| 15 | SLANNVTSV | ++ |
| 16 | APVNVTTEVKSV | ++ |
| 17 | FLKSGDAAIV | ++ |
| 18 | SLLDDELMSL | ++ |
| 20 | RLAGDGVGAV | ++ |
| 21 | HLMDQPLSV | ++ |
| 22 | TLDGAAVNQV | ++ |
| 23 | SLSAFTLFL | ++ |
| 24 | GLLEELVTV | ++ |
| 25 | SLKEEVGEEAI | ++ |
| 26 | SLKEEVGEEAIV | ++ |
| 27 | YLQGQRLDNV | ++ |
| 28 | YLQGQRLDNVV | ++ |
| 29 | FLQEYLDAI | +++ |
| 30 | VVDEGPTGV | ++ |
| 31 | SLAAAAGKQEL | ++ |
| 32 | SLAAAAGKQELA | + |
| 33 | SLDSRLELA | ++ |
| 34 | MLMPVHFLL | ++++ |
| 35 | VMDSGDGVTHTV | ++ |
| 37 | GLLKKINSV | ++ |
| 38 | NLVEKTPALV | +++ |
| 39 | TLLSNLEEA | ++ |
| 40 | FILDSAETTTL | ++ |
| 41 | FLLDGSEGV | +++ |
| 42 | KLVDKSTEL | ++ |
| 43 | RLDQRVPQI | ++ |
| 44 | VLLDKIKNLQV | ++ |
| 46 | TFAPVNVTTEVKSV | ++ |
| 47 | KMDASLGNLFA | ++++ |
| 48 | ALTQTGGPHV | ++ |
| 49 | NLKGTFATL | + |
| 50 | ALAAILTRL | +++ |
| 51 | ALMLQGVDL | ++ |
| 52 | RMVEEIGVEL | ++ |
| 53 | SSFGGLGGGSV | + |
| 54 | VLLSEIEVA | ++ |
| 55 | YLDAMMNEA | ++ |
| 56 | GLLDYATGAIGSV | +++ |
| 57 | FLGKVVIDV | ++++ |
| 58 | GLAAFKAFL | +++ |
| 59 | KLFNLSKEDDV | ++ |
| 60 | YLEEDVYQL | ++ |
| 64 | FLVSNMLLAEA | +++ |
| 65 | YLYDSETKNA | ++ |
| 66 | ALLSGLREA | +++ |
| 67 | KMFFLIDKV | +++ |

<20% = + ; 20%-49% = ++; 50%-75% = +++; > = 75% = ++++

REFERENCE LIST

Agesen, T. H. et al., Gut 61 (2012)
Alhumaidi, A., Indian J Dermatol. Venereol. Leprol. 78 (2012)
Allison, J. P. et al., Science 270 (1995)
Amatschek, S. et al., Cancer Res 64 (2004)
Andersen, R. S. et al., Nat. Protoc. 7 (2012)
Appay, V. et al., Eur. J Immunol. 36 (2006)
Appetecchia, M. et al., J Exp. Clin Cancer Res 29 (2010)

Arafat, H. et al., Surgery 150 (2011)
Ariga, N. et al., Int J Cancer 95 (2001)
Baek, G. et al., Cell Rep. 9 (2014)
Bai, L. et al., J Cell Biochem. 113 (2012)
Banchereau, J. et al., Cell 106 (2001)
Bausch, D. et al., Clin Cancer Res 17 (2011)
Beatty, G. et al., J Immunol 166 (2001)
Beggs, J. D., Nature 275 (1978)
Bell, J. L. et al., Cell Mol Life Sci. 70 (2013)
Benjamini, Y. et al., Journal of the Royal Statistical Society. Series B (Methodological), Vol. 57 (1995)
Bera, T. K. et al., Cancer Res 66 (2006)
Berndt, S. I. et al., Nat Genet. 45 (2013)
Blanch, A. et al., PLoS. One. 8 (2013)
Blenk, S. et al., BMC. Cancer 8 (2008)
Bo, H. et al., BMC. Cancer 13 (2013)
Bouameur, J. E. et al., J Invest Dermatol. 134 (2014)
Boulter, J. M. et al., Protein Eng 16 (2003)
Braumuller, H. et al., Nature (2013)
Brendle, A. et al., Carcinogenesis 29 (2008)
Brossart, P. et al., Blood 90 (1997)
Brown, S. G. et al., Prostate 75 (2015)
Bruckdorfer, T. et al., Curr. Pharm. Biotechnol. 5 (2004)
Calmon, M. F. et al., Neoplasia. 11 (2009)
Cao, H. H. et al., Oncotarget. (2014)
Cappello, F. et al., Curr. Pharm. Des 19 (2013)
Cappello, F. et al., Cancer Biol. Ther 7 (2008)
Cappello, F. et al., Front Biosci. (Schol. Ed) 3 (2011)
Capulli, M. et al., J Bone Miner. Res 27 (2012)
Card, K. F. et al., Cancer Immunol Immunother. 53 (2004)
Casagrande, G. et al., Haematologica 91 (2006)
Catanzaro, J. M. et al., Nat Commun. 5 (2014)
Chang, K. W. et al., Anticancer Res. 31 (2011)
Chang, K. W. et al., Hepatol. Res 36 (2006)
Chanock, S. J. et al., Hum. Immunol. 65 (2004)
Chaudhury, A. et al., Nat Cell Biol. 12 (2010)
Che, C. L. et al., Int J Clin Exp. Pathol. 6 (2013)
Chen, B. et al., Cancer Lett. 354 (2014a)
Chen, Q. et al., PLoS. One. 9 (2014b)
Chen, R. et al., Lab Invest 95 (2015)
Chen, S. et al., Cancer Epidemiol. 37 (2013a)
Chen, S. T. et al., Cancer Sci. 102 (2011)
Chen, Y. L. et al., Int J Surg. 11 (2013b)
Cheon, D. J. et al., Clin Cancer Res 20 (2014)
Cheung, H. C. et al., BMC. Genomics 9 (2008)
Choi, W. I. et al., Cell Physiol Biochem. 23 (2009)
Chow, S. N. et al., Eur. J Gynaecol. Oncol 31 (2010)
Cine, N. et al., Oncol Rep. 32 (2014)
Clement, S. et al., Virchows Arch. 442 (2003)
Cohen, C. J. et al., J Mol Recognit. 16 (2003a)
Cohen, C. J. et al., J Immunol 170 (2003b)
Cohen, S. J. et al., Pancreas 37 (2008)
Cohen, S. N. et al., Proc. Natl. Acad. Sci. U.S.A 69 (1972)
Coligan J E et al., (1995)
Colombetti, S. et al., J Immunol. 176 (2006)
Croner, R. S. et al., Int J Cancer 135 (2014)
Csiszar, A. et al., Breast Cancer Res 16 (2014)
Cucchiarelli, V. et al., Cell Motil. Cytoskeleton 65 (2008)
Culler, M. D., Horm. Metab Res 43 (2011)
Delaval, B. et al., Nat Cell Biol. 13 (2011)
Dengjel, J. et al., Clin Cancer Res 12 (2006)
Denkberg, G. et al., J Immunol 171 (2003)
Derycke, L. et al., Int J Dev. Biol. 55 (2011)
Dhup, S. et al., Curr. Pharm. Des 18 (2012)
Draoui, N. et al., Dis. Model. Mech. 4 (2011)
Dutton-Regester, K. et al., Genes Chromosomes. Cancer 51 (2012)
Egloff, A. M. et al., Cancer Res 66 (2006)
Ellis, M. J. et al., Nature 486 (2012)
Falk, K. et al., Nature 351 (1991)
Feng, H. et al., J Clin Invest 124 (2014)
Fillmore, R. A. et al., Exp. Biol. Med. (Maywood.) 239 (2014)
Findeis-Hosey, J. J. et al., Biotech. Histochem. 87 (2012)
Fong, L. et al., Proc. Natl. Acad. Sci. U.S.A 98 (2001)
Franz, M. et al., J Oral Pathol. Med. 39 (2010)
Fu, Y. et al., Cancer Biol. Ther 5 (2006)
Gabrilovich, D. I. et al., Nat Med. 2 (1996)
Galmarini, C. M. et al., Br. J Cancer 88 (2003)
Gamez-Pozo, A. et al., PLoS. One. 7 (2012)
Gao, H. J. et al., J Cancer Res Clin Oncol (2014a)
Gao, J. et al., PLoS. One. 9 (2014b)
Gao, Z. H. et al., Histopathology 65 (2014c)
Gardina, P. J. et al., BMC. Genomics 7 (2006)
Garg, M. et al., J Clin Endocrinol. Metab 99 (2014)
Gattinoni, L. et al., Nat Rev. Immunol 6 (2006)
Geyik, E. et al., Gene 540 (2014)
Glen, A. et al., Prostate 70 (2010)
Glymph, S. et al., Infect. Genet. Evol. 16 (2013)
Gnjatic, S. et al., Proc Natl. Acad. Sci. U.S.A 100 (2003)
Godkin, A. et al., Int. Immunol 9 (1997)
Gong, Y. et al., Adv. Anat. Pathol. 21 (2014)
Gorlov, I. P. et al., Cancer Res 67 (2007)
Green M R et al., 4th, (2012)
Greenfield E A, 2nd, (2014)
Guo, C. et al., Clin Chim. Acta 417 (2013)
Guo, C. et al., Nat Commun. 6 (2015)
Gutgemann, A. et al., Arch. Dermatol. Res 293 (2001)
Hait, W. N. et al., Trans. Am Clin Climatol. Assoc. 117 (2006)
Han, J. C. et al., World J Surg. Oncol 13 (2015)
Hao, X. et al., J Membr. Biol. 247 (2014)
He, X. et al., Neoplasma 61 (2014)
He, X. et al., Cancer Res 68 (2008)
Hoffmann, N. E. et al., Cancer 112 (2008)
Hopker, K. et al., EMBO J 31 (2012a)
Hopker, K. et al., Cell Cycle 11 (2012b)
Horibe, T. et al., Chembiochem. 15 (2014)
Horinouchi, M. et al., Pediatr. Hematol. Oncol 27 (2010)
Hu, S. et al., J Cancer Res Clin Oncol 140 (2014)
Hu, W. et al., Cell Death. Dis. 4 (2013)
Huang, H. C. et al., Technol. Cancer Res Treat. 9 (2010)
Hurst, J. H. et al., Cell Mol Biol. Lett. 14 (2009)
Hussey, G. S. et al., Mol Cell 41 (2011)
Hwang, M. L. et al., J Immunol. 179 (2007)
Hyung, S. W. et al., Mol Cell Proteomics. 10 (2011)
Ii, M. et al., Exp. Biol. Med. (Maywood.) 231 (2006)
Isfort, R. J. et al., Oncogene 15 (1997)
Ishiwata, T. et al., Oncol Rep. 18 (2007)
Izaki, T. et al., Biochem. Biophys. Res Commun. 329 (2005)
Jacob, M. et al., Curr. Mol Med. 12 (2012)
Jaeger, E. et al., Nat Genet. 44 (2012)
Jain, R. et al., Appl. Immunohistochem. Mol Morphol. 18 (2010)
Januchowski, R. et al., Biomed. Res Int 2014 (2014)
Jeda, A. et al., Ginekol. Pol. 85 (2014)
Jeng, Y. M. et al., Br. J Surg. 96 (2009)
Jeong, H. C. et al., J Proteome. Res 10 (2011)
Jones, A. et al., EMBO Mol Med. 5 (2013)
Jung, G. et al., Proc Natl Acad Sci USA 84 (1987)
Kamino, H. et al., Cancer Genet. 204 (2011)
Kaneko, K. et al., Pancreas 24 (2002)
Kang, C. Y. et al., J Gastrointest. Surg. 18 (2014)
Kang, G. H. et al., Lab Invest 88 (2008)

Kanzawa, M. et al., Pathobiology 80 (2013)
Karagiannis, G. S. et al., Oncotarget. 3 (2012)
Kashyap, M. K. et al., Cancer Biol. Ther 8 (2009)
Kashyap, V. et al., Mol Oncol 7 (2013)
Katada, K. et al., J Proteomics. 75 (2012)
Kevans, D. et al., Int J Surg. Pathol. 19 (2011)
Khalaileh, A. et al., Cancer Res 73 (2013)
Khuon, S. et al., J Cell Sci. 123 (2010)
Kibbe A H, rd, (2000)
Kido, T. et al., Genes (Basel) 1 (2010)
Kim, M. et al., Mol Cancer Res 6 (2008)
Kim, S. W. et al., OMICS. 15 (2011)
Kirov, A. et al., J Cell Biochem. (2015)
Kojima, M. et al., PLoS. One. 9 (2014)
Koshikawa, K. et al., Oncogene 21 (2002)
Kraya, A. A. et al., Autophagy. 11 (2015)
Krieg, A. M., Nat Rev. Drug Discov. 5 (2006)
Kuramitsu, Y. et al., Anticancer Res 30 (2010)
Kuramitsu, Y. et al., Anticancer Res 31 (2011)
Kuroda, N. et al., Histol. Histopathol. 20 (2005)
Kuroda, N. et al., Pathol. Int 63 (2013)
Kwon, J. et al., Int J Oncol 43 (2013)
Lahsnig, C. et al., Oncogene 28 (2009)
Lee, C. W. et al., World J Surg. Oncol 11 (2013a)
Lee, H. W. et al., Clin Cancer Res 19 (2013b)
Lee, H. W. et al., Int J Oncol 41 (2012)
Lee, K. Y. et al., J Med. 35 (2004)
Lee, M. A. et al., BMC. Cancer 14 (2014)
Leivo, I. et al., Cancer Genet. Cytogenet. 156 (2005)
Leygue, E. et al., Cancer Res 58 (1998)
Li, G. H. et al., Bioinformatics. 30 (2014)
Li, X. et al., Clin Cancer Res 20 (2014)
Li, X. et al., PLoS. One. 8 (2013)
Li, Y. et al., Cancer Genet. Cytogenet. 198 (2010)
Liddy, N. et al., Nat Med. 18 (2012)
Lieveld, M. et al., Virchows Arch. 465 (2014)
Lim, R. et al., Biochem. Biophys. Res Commun. 406 (2011)
Lim, W. et al., J Cancer Prev. 18 (2013)
Lin, H. C. et al., J Proteome. Res 12 (2013a)
Lin, L. et al., Oncol Lett. 6 (2013b)
Linge, A. et al., Invest Ophthalmol. Vis. Sci. 53 (2012)
Liu, H. et al., Carcinogenesis 34 (2013a)
Liu, M. et al., Reprod. Sci. 20 (2013b)
Liu, X. F. et al., Apoptosis. 14 (2009)
Ljunggren, H. G. et al., J Exp. Med. 162 (1985)
Long, Z. W. et al., Tumour. Biol. 35 (2014)
Longenecker, B. M. et al., Ann N. Y. Acad. Sci. 690 (1993)
Lu, C. et al., Dig. Dis. Sci. 58 (2013a)
Lu, X. et al., Cancer Biother. Radiopharm. 28 (2013b)
Lukas, T. J. et al., Proc. Natl. Acad. Sci. U. S. A 78 (1981)
Lund, R. R. et al., Proteomics. 12 (2012)
Lundblad R L, 3rd, (2004)
Lung, H. L. et al., Int. J Cancer 127 (2010)
Luo, Y. et al., Mol Med. Rep. 9 (2014)
Lv, T. et al., PLoS. One. 7 (2012)
Manning, T. J., Jr. et al., Cell Motil. Cytoskeleton 45 (2000)
Marg, A. et al., Biochem. Biophys. Res Commun. 401 (2010)
Matassa, D. S. et al., Cell Death. Dis. 4 (2013)
Matchett, K. B. et al., Adv. Exp. Med. Biol. 773 (2014)
Mazieres, J. et al., Oncogene 24 (2005)
McCluggage, W. G. et al., Semin. Diagn. Pathol. 22 (2005)
McIntyre, J. C. et al., Nat Med. 18 (2012)
Medjkane, S. et al., Nat Cell Biol. 11 (2009)
Meng, F. et al., Int J Oncol 43 (2013)
Menhofer, M. H. et al., PLoS. One. 9 (2014)
Mentlein, R. et al., Biol. Chem. 392 (2011)
Meziere, C. et al., J Immunol 159 (1997)
Milani, C. et al., BMC. Cancer 13 (2013)
Miyagi, T. et al., Mol Urol. 5 (2001)
Mochizuki, S. et al., Cancer Sci. 98 (2007)
Modlin, I. M. et al., Aliment. Pharmacol. Ther 31 (2010)
Morgan, R. A. et al., Science 314 (2006)
Mori, M. et al., Transplantation 64 (1997)
Mortara, L. et al., Clin Cancer Res. 12 (2006)
Mu, Y. et al., Electrophoresis 34 (2013)
Mueller, L. N. et al., J Proteome. Res 7 (2008)
Mueller, L. N. et al., Proteomics. 7 (2007)
Mumberg, D. et al., Proc. Natl. Acad. Sci. U. S. A 96 (1999)
Mushinski, J. F. et al., J Biol. Chem. 284 (2009)
Nakamura, H. et al., Curr. Pharm. Des 19 (2013)
Nakayama, H. et al., J Clin Pathol. 55 (2002)
Nassar, Z. D. et al., Oncotarget. 4 (2013)
Niedergethmann, M. et al., Br. J Cancer 97 (2007)
Nikolova, D. N. et al., Oncol Rep. 20 (2008)
Nishioka, M. et al., Oncogene 19 (2000)
Olesen, S. H. et al., Mol Cell Proteomics. 4 (2005)
Ou, Y. et al., Urol. Oncol 32 (2014)
Pace, A. et al., Curr. Pharm. Des 19 (2013)
Pan, S. et al., OMICS. 13 (2009)
Panico, F. et al., Adv. Cancer Res 105 (2009)
Patel, R. A. et al., Cancer Res 72 (2012)
Pereira, P. M. et al., Org. Biomol. Chem. 12 (2014)
Pinheiro J et al., (2015)
Pitule, P. et al., Anticancer Res 33 (2013)
Pivonello, C. et al., Infect. Agent. Cancer 9 (2014)
Plebanski, M. et al., Eur. J Immunol 25 (1995)
Pontisso, P., Ann Hepatol. 13 (2014)
Porta, C. et al., Virology 202 (1994)
Portela-Gomes, G. M. et al., Regul. Pept. 146 (2008)
Qi, Y. et al., Proteomics. 5 (2005)
Qu, Z. et al., Cancer Med. 3 (2014)
Quinn, M. C. et al., Int J Oncol 42 (2013)
Rammensee, H. G. et al., Immunogenetics 50 (1999)
Reddy, S. P. et al., Clin Cancer Res 14 (2008)
RefSeq, The NCBI handbook [Internet], Chapter 18 (2002)
Rehman, I. et al., PLoS. One. 7 (2012)
Rini, B. I. et al., Cancer 107 (2006)
Robinson, T. J. et al., Cell Cycle 12 (2013)
Rock, K. L. et al., Science 249 (1990)
Roman-Gomez, J. et al., Blood 109 (2007)
Roustit, M. M. et al., J Endocrinol. 223 (2014)
Roy, D. et al., Blood 118 (2011)
Rucki, A. A. et al., World J Gastroenterol. 20 (2014)
S3-Leitlinie Exokrines Pankreaskarzinom, 032-010OL, (2013)
Saiki, R. K. et al., Science 239 (1988)
Salman, B. et al., Oncoimmunology. 2 (2013)
Sato, Y. et al., J Cell Sci. 126 (2013)
Savoy, R. M. et al., Endocr. Relat Cancer 20 (2013)
Schlomann, U. et al., Nat Commun. 6 (2015)
Schroder, W. A. et al., Cancer Med. 3 (2014)
Schulte, J. et al., Histochem. Cell Biol. 138 (2012)
Scrideli, C. A. et al., J Neurooncol. 88 (2008)
Seeger, F. H. et al., Immunogenetics 49 (1999)
Seya, T. et al., Oncol Rep. 16 (2006)
Sherman F et al., (1986)
Sherman-Baust, C. A. et al., Cancer Cell 3 (2003)
Simiczyjew, A. et al., Histochem. Cell Biol. 142 (2014)
Singh-Jasuja, H. et al., Cancer Immunol. Immunother. 53 (2004)
Skondra, M. et al., Anticancer Res 34 (2014)
Small, E. J. et al., J Clin Oncol. 24 (2006)
Smith, M. J. et al., Br. J Cancer 100 (2009)

Song, B. L. et al., Biochem. J 394 (2006)
Song, Q. et al., Tumour. Biol. 35 (2014)
Sood, A. K., Immunol Res 46 (2010)
Souchek, J. J. et al., Br. J Cancer 111 (2014)
Stolk, J. A. et al., Prostate 60 (2004)
Sturm, M. et al., BMC. Bioinformatics. 9 (2008)
Sun, D. W. et al., Cancer Epidemiol. (2015a)
Sun, J. et al., J Mol Histol. 46 (2015b)
Sun, Z. et al., J Proteome. Res 13 (2014)
Suzuki, H. et al., Int J Oncol 12 (1998)
Szarvas, T. et al., Int J Cancer 135 (2014)
Takahashi, K. et al., Peptides 27 (2006)
Takeuchi, A. et al., Mol Cell Endocrinol. 384 (2014)
Tatenhorst, L. et al., J Neuropathol. Exp. Neurol. 63 (2004)
Terabayashi, T. et al., PLoS. One. 7 (2012)
Terada, T. et al., J Hepatol. 24 (1996)
Teufel, R. et al., Cell Mol Life Sci. 62 (2005)
Thorsen, K. et al., Mol Cell Proteomics. 7 (2008)
Tran, E. et al., Science 344 (2014)
Trougakos, I. P., Gerontology 59 (2013)
Tummala, R. et al., Cancer Chemother. Pharmacol. 64 (2009)
Unger, K. et al., Endocr. Relat Cancer 17 (2010)
Untergasser, G. et al., Mech. Ageing Dev. 126 (2005)
Vassar, R. et al., J Neurochem. 130 (2014)
Von Hoff, D. D. et al., N. Engl. J Med. 369 (2013)
Vui-Kee, K. et al., Kaohsiung. J Med. Sci. 28 (2012)
Walker, E. J. et al., World J Gastroenterol. 20 (2014)
Walter, S. et al., J Immunol 171 (2003)
Walter, S. et al., Nat Med. 18 (2012)
Wang, G. H. et al., Oncol Lett. 5 (2013a)
Wang, H. et al., Front Oncol 4 (2014a)
Wang, J. et al., J Exp. Clin Cancer Res 34 (2015)
Wang, Q. et al., PLoS. One. 8 (2013b)
Wang, X. et al., Urol. Int. 92 (2014b)
Wang, X. Y. et al., Int J Hyperthermia 29 (2013)
Watson, M. B. et al., Acta Oncol 46 (2007)
Watt, H. L. et al., Mol Cell Endocrinol. 286 (2008)
Weber, A. M. et al., Pharmacol. Ther (2014)
Wikberg, M. L. et al., Tumour. Biol. 34 (2013)
Willcox, B. E. et al., Protein Sci. 8 (1999)
Williams, S. et al., PLoS. One. 8 (2013)
Wong, C. C. et al., Nat Genet. 46 (2014)
World Cancer Report, (2014)
Xia, Z. K. et al., Dis. Esophagus. 25 (2012)
Xie, X. et al., Oncol Lett. 7 (2014)
Xiong, D. et al., Carcinogenesis 33 (2012)
Xu, C. Z. et al., Int J Clin Exp. Pathol. 6 (2013)
Yang, C. Y. et al., J Immunol 192 (2014a)
Yang, H. et al., PLoS. One. 9 (2014b)
Yang, S. et al., Biochim. Biophys. Acta 1772 (2007)
Yasui, W. et al., Cancer Sci. 95 (2004)
Yeung, T. L. et al., Cancer Res 73 (2013)
Yu, X. et al., Cancer Res 73 (2013)
Yuan, B. et al., Immunobiology 217 (2012)
Yuan, D. et al., J Surg. Oncol 108 (2013)
Yuan, R. H. et al., Ann Surg. Oncol 16 (2009)
Zanaruddin, S. N. et al., Hum. Pathol. 44 (2013)
Zaravinos, A. et al., PLoS. One. 6 (2011)
Zaremba, S. et al., Cancer Res. 57 (1997)
Zhang, C. et al., Biochem. Biophys. Res Commun. 434 (2013)
Zhang, C. C. et al., Cancer Res 59 (1999)
Zhang, Y. et al., Zhonghua Gan Zang. Bing. Za Zhi. 14 (2006)
Zhang, Y. et al., Cancer Lett. 303 (2011)
Zhao, D. et al., J Neurooncol. 118 (2014)
Zhao, Z. K. et al., Tumour. Biol. 34 (2013)
Zhu, H. H. et al., Asian Pac. J Trop. Med. 7 (2014)
Zocchi, M. R. et al., Blood 119 (2012)
Zou, T. T. et al., Oncogene 21 (2002)

The invention claimed is:

1. A method of treating cancer in a HLA-A*02+ patient, wherein said cancer comprises cancer cells that overexpress a polypeptide and present at their surface in complex with an MHC class I molecule a peptide consisting of the amino acid sequence of SEQ ID NO: 10, said method comprising administering to said patient an effective amount of activated antigen-specific CD8+ cytotoxic T cells to kill cancer cells, wherein said activated antigen-specific CD8+ cytotoxic T cells are produced by contacting in vitro CD8+ cytotoxic T cells with an antigen presenting cell presenting at its surface in complex with an MHC class I molecule a peptide consisting of the amino acid sequence of SEQ ID NO: 10, wherein said cancer is selected from pancreatic cancer, colon or rectal cancer, melanoma, esophageal cancer, breast cancer, small cell lung cancer, stomach cancer, urinary bladder cancer, gall bladder cancer, and bile duct cancer.

2. The method of claim 1, wherein the cytotoxic T cells produced by contacting CD8+ cytotoxic T cells with said antigen presenting cell are cytotoxic T cells autologous to the patient.

3. The method of claim 1, wherein the cytotoxic T cells produced by contacting CD8+ cytotoxic T cells with said antigen presenting cell are cytotoxic T cells obtained from a healthy donor.

4. The method of claim 1, wherein the cytotoxic T cells produced by contacting CD8+ cytotoxic T cells with said antigen presenting cell are cytotoxic T cells isolated from tumor infiltrating lymphocytes or peripheral blood mononuclear cells.

5. The method of claim 1, wherein the cytotoxic T cells produced by contacting CD8+ cytotoxic T cells with said antigen presenting cell are expanded in vitro before being administered to the patient.

6. The method of claim 1, wherein the cytotoxic T cells are expanded in vitro in the presence of an anti-CD28 antibody and IL-12.

7. The method of claim 1, wherein the effective amount of activated antigen-specific CD8+ cytotoxic T cells to kill the cancer cells are administered in the form of a composition.

8. The method of claim 7, wherein said composition further comprises an adjuvant.

9. The method of claim 8, wherein said adjuvant is selected from agonistic anti-CD40 antibody, imiquimod, resiquimod, GM-CSF, cyclophosphamide, sunitinib, interferon-alpha, interferon-beta, CpG oligonucleotides, poly-(I:C), RNA, sildenafil, particulate formulations with poly (lactide co-glycolide) (PLG), virosomes, interleukin (IL)-1, IL-2, IL-4, IL-7, IL-12, IL-13, IL-15, IL-21, and IL-23.

10. The method of claim 8, wherein the adjuvant comprises IL-2.

11. The method of claim 8, wherein the adjuvant comprises IL-21.

12. The method of claim 1, wherein the antigen presenting cell is a dendritic cell or a macrophage.

13. The method of claim 1, wherein the antigen presenting cell is infected with a recombinant virus expressing a peptide consisting of the amino acid sequence of SEQ ID NO: 10.

14. The method of claim 1, wherein the antigen presenting cell is an artificial antigen presenting cell (aAPC) comprising an anti-CD28 antibody coupled to its surface.

15. The method of claim 1, wherein the cancer is pancreatic cancer.

16. The method of claim 1, wherein the cancer is colon or rectal cancer.

17. The method of claim 1, wherein the cancer is melanoma.

18. The method of claim 1, wherein the cancer is breast cancer.

19. The method of claim 1, wherein the cancer is small cell lung cancer.

20. The method of claim 1, wherein the cancer is esophageal cancer.

* * * * *

SEQUENCE LISTING

```
<160> NUMBER OF SEQ ID NOS: 89

<210> SEQ ID NO 1
<211> LENGTH: 9
<212> TYPE: PRT
<213> ORGANISM: Homo sapiens

<400> SEQUENCE: 1

Phe Leu Ala Gln Gln Glu Ser Glu Ile
1               5

<210> SEQ ID NO 2
<211> LENGTH: 10
<212> TYPE: PRT
<213> ORGANISM: Homo sapiens

<400> SEQUENCE: 2

Ser Leu Gln Glu Glu His Val Ala Val Ala
1               5                   10

<210> SEQ ID NO 3
<211> LENGTH: 9
<212> TYPE: PRT
<213> ORGANISM: Homo sapiens

<400> SEQUENCE: 3

Ala Leu Leu Thr Phe Met Glu Gln Val
1               5
```

```
<210> SEQ ID NO 4
<211> LENGTH: 9
<212> TYPE: PRT
<213> ORGANISM: Homo sapiens

<400> SEQUENCE: 4

Ser Val Asp Val Ser Pro Pro Lys Val
1               5

<210> SEQ ID NO 5
<211> LENGTH: 11
<212> TYPE: PRT
<213> ORGANISM: Homo sapiens

<400> SEQUENCE: 5

Leu Leu Val Asp Asp Ser Phe Leu His Thr Val
1               5                   10

<210> SEQ ID NO 6
<211> LENGTH: 11
<212> TYPE: PRT
<213> ORGANISM: Homo sapiens

<400> SEQUENCE: 6

Val Leu Ile Ser Leu Lys Gln Ala Pro Leu Val
1               5                   10

<210> SEQ ID NO 7
<211> LENGTH: 10
<212> TYPE: PRT
<213> ORGANISM: Homo sapiens

<400> SEQUENCE: 7

Ala Gln Gln Glu Ser Glu Ile Ala Gly Ile
1               5                   10

<210> SEQ ID NO 8
<211> LENGTH: 9
<212> TYPE: PRT
<213> ORGANISM: Homo sapiens

<400> SEQUENCE: 8

Ile Val Asp Asp Leu Thr Ile Asn Leu
1               5

<210> SEQ ID NO 9
<211> LENGTH: 10
<212> TYPE: PRT
<213> ORGANISM: Homo sapiens

<400> SEQUENCE: 9

Phe Leu Phe Asp Gly Ser Ala Asn Leu Val
1               5                   10

<210> SEQ ID NO 10
<211> LENGTH: 9
<212> TYPE: PRT
<213> ORGANISM: Homo sapiens

<400> SEQUENCE: 10

Phe Leu Val Asp Gly Ser Ser Ala Leu
1               5
```

```
<210> SEQ ID NO 11
<211> LENGTH: 9
<212> TYPE: PRT
<213> ORGANISM: Homo sapiens

<400> SEQUENCE: 11

Phe Leu Tyr Lys Ile Ile Asp Glu Leu
1               5

<210> SEQ ID NO 12
<211> LENGTH: 9
<212> TYPE: PRT
<213> ORGANISM: Homo sapiens

<400> SEQUENCE: 12

Phe Val Ser Glu Ile Val Asp Thr Val
1               5

<210> SEQ ID NO 13
<211> LENGTH: 9
<212> TYPE: PRT
<213> ORGANISM: Homo sapiens

<400> SEQUENCE: 13

Leu Leu Ala Gly Gln Thr Tyr His Val
1               5

<210> SEQ ID NO 14
<211> LENGTH: 10
<212> TYPE: PRT
<213> ORGANISM: Homo sapiens

<400> SEQUENCE: 14

Val Leu Ala Lys Pro Gly Val Ile Ser Val
1               5                   10

<210> SEQ ID NO 15
<211> LENGTH: 9
<212> TYPE: PRT
<213> ORGANISM: Homo sapiens

<400> SEQUENCE: 15

Ser Leu Ala Asn Asn Val Thr Ser Val
1               5

<210> SEQ ID NO 16
<211> LENGTH: 12
<212> TYPE: PRT
<213> ORGANISM: Homo sapiens

<400> SEQUENCE: 16

Ala Pro Val Asn Val Thr Thr Glu Val Lys Ser Val
1               5                   10

<210> SEQ ID NO 17
<211> LENGTH: 10
<212> TYPE: PRT
<213> ORGANISM: Homo sapiens

<400> SEQUENCE: 17

Phe Leu Lys Ser Gly Asp Ala Ala Ile Val
1               5                   10

<210> SEQ ID NO 18
<211> LENGTH: 10
```

```
<212> TYPE: PRT
<213> ORGANISM: Homo sapiens

<400> SEQUENCE: 18

Ser Leu Leu Asp Asp Glu Leu Met Ser Leu
1               5                   10

<210> SEQ ID NO 19
<211> LENGTH: 11
<212> TYPE: PRT
<213> ORGANISM: Homo sapiens

<400> SEQUENCE: 19

His Leu Ala Pro Glu Thr Asp Glu Asp Leu
1               5                   10

<210> SEQ ID NO 20
<211> LENGTH: 10
<212> TYPE: PRT
<213> ORGANISM: Homo sapiens

<400> SEQUENCE: 20

Arg Leu Ala Gly Asp Gly Val Gly Ala Val
1               5                   10

<210> SEQ ID NO 21
<211> LENGTH: 9
<212> TYPE: PRT
<213> ORGANISM: Homo sapiens

<400> SEQUENCE: 21

His Leu Met Asp Gln Pro Leu Ser Val
1               5

<210> SEQ ID NO 22
<211> LENGTH: 10
<212> TYPE: PRT
<213> ORGANISM: Homo sapiens

<400> SEQUENCE: 22

Thr Leu Asp Gly Ala Ala Val Asn Gln Val
1               5                   10

<210> SEQ ID NO 23
<211> LENGTH: 9
<212> TYPE: PRT
<213> ORGANISM: Homo sapiens

<400> SEQUENCE: 23

Ser Leu Ser Ala Phe Thr Leu Phe Leu
1               5

<210> SEQ ID NO 24
<211> LENGTH: 9
<212> TYPE: PRT
<213> ORGANISM: Homo sapiens

<400> SEQUENCE: 24

Gly Leu Leu Glu Glu Leu Val Thr Val
1               5

<210> SEQ ID NO 25
<211> LENGTH: 11
<212> TYPE: PRT
<213> ORGANISM: Homo sapiens
```

<400> SEQUENCE: 25

Ser Leu Lys Glu Glu Val Gly Glu Glu Ala Ile
1               5                   10

<210> SEQ ID NO 26
<211> LENGTH: 12
<212> TYPE: PRT
<213> ORGANISM: Homo sapiens

<400> SEQUENCE: 26

Ser Leu Lys Glu Glu Val Gly Glu Glu Ala Ile Val
1               5                   10

<210> SEQ ID NO 27
<211> LENGTH: 10
<212> TYPE: PRT
<213> ORGANISM: Homo sapiens

<400> SEQUENCE: 27

Tyr Leu Gln Gly Gln Arg Leu Asp Asn Val
1               5                   10

<210> SEQ ID NO 28
<211> LENGTH: 11
<212> TYPE: PRT
<213> ORGANISM: Homo sapiens

<400> SEQUENCE: 28

Tyr Leu Gln Gly Gln Arg Leu Asp Asn Val Val
1               5                   10

<210> SEQ ID NO 29
<211> LENGTH: 9
<212> TYPE: PRT
<213> ORGANISM: Homo sapiens

<400> SEQUENCE: 29

Phe Leu Gln Glu Tyr Leu Asp Ala Ile
1               5

<210> SEQ ID NO 30
<211> LENGTH: 9
<212> TYPE: PRT
<213> ORGANISM: Homo sapiens

<400> SEQUENCE: 30

Val Val Asp Glu Gly Pro Thr Gly Val
1               5

<210> SEQ ID NO 31
<211> LENGTH: 11
<212> TYPE: PRT
<213> ORGANISM: Homo sapiens

<400> SEQUENCE: 31

Ser Leu Ala Ala Ala Ala Gly Lys Gln Glu Leu
1               5                   10

<210> SEQ ID NO 32
<211> LENGTH: 12
<212> TYPE: PRT
<213> ORGANISM: Homo sapiens

<400> SEQUENCE: 32

```
Ser Leu Ala Ala Ala Gly Lys Gln Glu Leu Ala
1               5                   10
```

<210> SEQ ID NO 33
<211> LENGTH: 9
<212> TYPE: PRT
<213> ORGANISM: Homo sapiens

<400> SEQUENCE: 33

```
Ser Leu Asp Ser Arg Leu Glu Leu Ala
1               5
```

<210> SEQ ID NO 34
<211> LENGTH: 9
<212> TYPE: PRT
<213> ORGANISM: Homo sapiens

<400> SEQUENCE: 34

```
Met Leu Met Pro Val His Phe Leu Leu
1               5
```

<210> SEQ ID NO 35
<211> LENGTH: 12
<212> TYPE: PRT
<213> ORGANISM: Homo sapiens

<400> SEQUENCE: 35

```
Val Met Asp Ser Gly Asp Gly Val Thr His Thr Val
1               5                   10
```

<210> SEQ ID NO 36
<211> LENGTH: 13
<212> TYPE: PRT
<213> ORGANISM: Homo sapiens

<400> SEQUENCE: 36

```
Lys Gln Glu Tyr Asp Glu Ser Gly Pro Ser Ile Val His
1               5                   10
```

<210> SEQ ID NO 37
<211> LENGTH: 9
<212> TYPE: PRT
<213> ORGANISM: Homo sapiens

<400> SEQUENCE: 37

```
Gly Leu Leu Lys Lys Ile Asn Ser Val
1               5
```

<210> SEQ ID NO 38
<211> LENGTH: 10
<212> TYPE: PRT
<213> ORGANISM: Homo sapiens

<400> SEQUENCE: 38

```
Asn Leu Val Glu Lys Thr Pro Ala Leu Val
1               5                   10
```

<210> SEQ ID NO 39
<211> LENGTH: 9
<212> TYPE: PRT
<213> ORGANISM: Homo sapiens

<400> SEQUENCE: 39

```
Thr Leu Leu Ser Asn Leu Glu Glu Ala
```

<210> SEQ ID NO 40
<211> LENGTH: 11
<212> TYPE: PRT
<213> ORGANISM: Homo sapiens

<400> SEQUENCE: 40

Phe Ile Leu Asp Ser Ala Glu Thr Thr Thr Leu
1               5                   10

<210> SEQ ID NO 41
<211> LENGTH: 9
<212> TYPE: PRT
<213> ORGANISM: Homo sapiens

<400> SEQUENCE: 41

Phe Leu Leu Asp Gly Ser Glu Gly Val
1               5

<210> SEQ ID NO 42
<211> LENGTH: 9
<212> TYPE: PRT
<213> ORGANISM: Homo sapiens

<400> SEQUENCE: 42

Lys Leu Val Asp Lys Ser Thr Glu Leu
1               5

<210> SEQ ID NO 43
<211> LENGTH: 9
<212> TYPE: PRT
<213> ORGANISM: Homo sapiens

<400> SEQUENCE: 43

Arg Leu Asp Gln Arg Val Pro Gln Ile
1               5

<210> SEQ ID NO 44
<211> LENGTH: 11
<212> TYPE: PRT
<213> ORGANISM: Homo sapiens

<400> SEQUENCE: 44

Val Leu Leu Asp Lys Ile Lys Asn Leu Gln Val
1               5                   10

<210> SEQ ID NO 45
<211> LENGTH: 8
<212> TYPE: PRT
<213> ORGANISM: Homo sapiens

<400> SEQUENCE: 45

Val Ala Asp Lys Ile His Ser Val
1               5

<210> SEQ ID NO 46
<211> LENGTH: 14
<212> TYPE: PRT
<213> ORGANISM: Homo sapiens

<400> SEQUENCE: 46

Thr Phe Ala Pro Val Asn Val Thr Thr Glu Val Lys Ser Val
1               5                   10

```
<210> SEQ ID NO 47
<211> LENGTH: 11
<212> TYPE: PRT
<213> ORGANISM: Homo sapiens

<400> SEQUENCE: 47

Lys Met Asp Ala Ser Leu Gly Asn Leu Phe Ala
1               5                   10

<210> SEQ ID NO 48
<211> LENGTH: 10
<212> TYPE: PRT
<213> ORGANISM: Homo sapiens

<400> SEQUENCE: 48

Ala Leu Thr Gln Thr Gly Gly Pro His Val
1               5                   10

<210> SEQ ID NO 49
<211> LENGTH: 9
<212> TYPE: PRT
<213> ORGANISM: Homo sapiens

<400> SEQUENCE: 49

Asn Leu Lys Gly Thr Phe Ala Thr Leu
1               5

<210> SEQ ID NO 50
<211> LENGTH: 9
<212> TYPE: PRT
<213> ORGANISM: Homo sapiens

<400> SEQUENCE: 50

Ala Leu Ala Ala Ile Leu Thr Arg Leu
1               5

<210> SEQ ID NO 51
<211> LENGTH: 9
<212> TYPE: PRT
<213> ORGANISM: Homo sapiens

<400> SEQUENCE: 51

Ala Leu Met Leu Gln Gly Val Asp Leu
1               5

<210> SEQ ID NO 52
<211> LENGTH: 10
<212> TYPE: PRT
<213> ORGANISM: Homo sapiens

<400> SEQUENCE: 52

Arg Met Val Glu Glu Ile Gly Val Glu Leu
1               5                   10

<210> SEQ ID NO 53
<211> LENGTH: 11
<212> TYPE: PRT
<213> ORGANISM: Homo sapiens

<400> SEQUENCE: 53

Ser Ser Phe Gly Gly Leu Gly Gly Gly Ser Val
1               5                   10

<210> SEQ ID NO 54
```

```
<210> SEQ ID NO 54
<211> LENGTH: 9
<212> TYPE: PRT
<213> ORGANISM: Homo sapiens

<400> SEQUENCE: 54

Val Leu Leu Ser Glu Ile Glu Val Ala
1               5

<210> SEQ ID NO 55
<211> LENGTH: 9
<212> TYPE: PRT
<213> ORGANISM: Homo sapiens

<400> SEQUENCE: 55

Tyr Leu Asp Ala Met Met Asn Glu Ala
1               5

<210> SEQ ID NO 56
<211> LENGTH: 13
<212> TYPE: PRT
<213> ORGANISM: Homo sapiens

<400> SEQUENCE: 56

Gly Leu Leu Asp Tyr Ala Thr Gly Ala Ile Gly Ser Val
1               5                   10

<210> SEQ ID NO 57
<211> LENGTH: 9
<212> TYPE: PRT
<213> ORGANISM: Homo sapiens

<400> SEQUENCE: 57

Phe Leu Gly Lys Val Val Ile Asp Val
1               5

<210> SEQ ID NO 58
<211> LENGTH: 9
<212> TYPE: PRT
<213> ORGANISM: Homo sapiens

<400> SEQUENCE: 58

Gly Leu Ala Ala Phe Lys Ala Phe Leu
1               5

<210> SEQ ID NO 59
<211> LENGTH: 11
<212> TYPE: PRT
<213> ORGANISM: Homo sapiens

<400> SEQUENCE: 59

Lys Leu Phe Asn Leu Ser Lys Glu Asp Asp Val
1               5                   10

<210> SEQ ID NO 60
<211> LENGTH: 9
<212> TYPE: PRT
<213> ORGANISM: Homo sapiens

<400> SEQUENCE: 60

Tyr Leu Glu Glu Asp Val Tyr Gln Leu
1               5

<210> SEQ ID NO 61
<211> LENGTH: 11
<212> TYPE: PRT
```

```
<213> ORGANISM: Homo sapiens

<400> SEQUENCE: 61

Ala Leu Glu Lys Asp Tyr Glu Glu Val Gly Val
1               5                   10

<210> SEQ ID NO 62
<211> LENGTH: 9
<212> TYPE: PRT
<213> ORGANISM: Homo sapiens

<400> SEQUENCE: 62

Ala Leu Glu Lys Asp Tyr Glu Glu Val
1               5

<210> SEQ ID NO 63
<211> LENGTH: 8
<212> TYPE: PRT
<213> ORGANISM: Homo sapiens

<400> SEQUENCE: 63

Phe Ala Gly Asp Asp Ala Pro Arg
1               5

<210> SEQ ID NO 64
<211> LENGTH: 11
<212> TYPE: PRT
<213> ORGANISM: Homo sapiens

<400> SEQUENCE: 64

Phe Leu Val Ser Asn Met Leu Leu Ala Glu Ala
1               5                   10

<210> SEQ ID NO 65
<211> LENGTH: 10
<212> TYPE: PRT
<213> ORGANISM: Homo sapiens

<400> SEQUENCE: 65

Tyr Leu Tyr Asp Ser Glu Thr Lys Asn Ala
1               5                   10

<210> SEQ ID NO 66
<211> LENGTH: 9
<212> TYPE: PRT
<213> ORGANISM: Homo sapiens

<400> SEQUENCE: 66

Ala Leu Leu Ser Gly Leu Arg Glu Ala
1               5

<210> SEQ ID NO 67
<211> LENGTH: 9
<212> TYPE: PRT
<213> ORGANISM: Homo sapiens

<400> SEQUENCE: 67

Lys Met Phe Phe Leu Ile Asp Lys Val
1               5

<210> SEQ ID NO 68
<211> LENGTH: 9
<212> TYPE: PRT
<213> ORGANISM: Homo sapiens
```

<400> SEQUENCE: 68

Lys Leu Leu Thr Glu Val His Ala Ala
1               5

<210> SEQ ID NO 69
<211> LENGTH: 9
<212> TYPE: PRT
<213> ORGANISM: Homo sapiens

<400> SEQUENCE: 69

Val Met Ala Pro Phe Thr Met Thr Ile
1               5

<210> SEQ ID NO 70
<211> LENGTH: 9
<212> TYPE: PRT
<213> ORGANISM: Homo sapiens

<400> SEQUENCE: 70

Phe Leu Val Asp Gly Ser Trp Ser Val
1               5

<210> SEQ ID NO 71
<211> LENGTH: 9
<212> TYPE: PRT
<213> ORGANISM: Homo sapiens

<400> SEQUENCE: 71

Phe Leu Leu Asp Gly Ser Ala Asn Val
1               5

<210> SEQ ID NO 72
<211> LENGTH: 9
<212> TYPE: PRT
<213> ORGANISM: Homo sapiens

<400> SEQUENCE: 72

Tyr Val Tyr Gln Asn Asn Ile Tyr Leu
1               5

<210> SEQ ID NO 73
<211> LENGTH: 9
<212> TYPE: PRT
<213> ORGANISM: Homo sapiens

<400> SEQUENCE: 73

Thr Leu Val Ala Ile Val Val Gly Val
1               5

<210> SEQ ID NO 74
<211> LENGTH: 9
<212> TYPE: PRT
<213> ORGANISM: Homo sapiens

<400> SEQUENCE: 74

Lys Ile Gln Glu Ile Leu Thr Gln Val
1               5

<210> SEQ ID NO 75
<211> LENGTH: 9
<212> TYPE: PRT
<213> ORGANISM: Homo sapiens

<400> SEQUENCE: 75

Arg Leu Asp Asp Leu Lys Met Thr Val
1               5

<210> SEQ ID NO 76
<211> LENGTH: 9
<212> TYPE: PRT
<213> ORGANISM: Homo sapiens

<400> SEQUENCE: 76

Arg Leu Leu Asp Ser Val Ser Arg Leu
1               5

<210> SEQ ID NO 77
<211> LENGTH: 9
<212> TYPE: PRT
<213> ORGANISM: Homo sapiens

<400> SEQUENCE: 77

Gly Leu Thr Asp Asn Ile His Leu Val
1               5

<210> SEQ ID NO 78
<211> LENGTH: 9
<212> TYPE: PRT
<213> ORGANISM: Homo sapiens

<400> SEQUENCE: 78

Thr Leu Ser Ser Ile Lys Val Glu Val
1               5

<210> SEQ ID NO 79
<211> LENGTH: 9
<212> TYPE: PRT
<213> ORGANISM: Homo sapiens

<400> SEQUENCE: 79

Val Leu Ala Pro Arg Val Leu Arg Ala
1               5

<210> SEQ ID NO 80
<211> LENGTH: 9
<212> TYPE: PRT
<213> ORGANISM: Homo sapiens

<400> SEQUENCE: 80

Thr Leu Tyr Pro His Thr Ser Gln Val
1               5

<210> SEQ ID NO 81
<211> LENGTH: 9
<212> TYPE: PRT
<213> ORGANISM: Homo sapiens

<400> SEQUENCE: 81

Ala Met Ser Ser Lys Phe Phe Leu Val
1               5

<210> SEQ ID NO 82
<211> LENGTH: 9
<212> TYPE: PRT
<213> ORGANISM: Homo sapiens

<400> SEQUENCE: 82

Ser Ile Ser Asp Val Ile Ala Gln Val
1               5

<210> SEQ ID NO 83
<211> LENGTH: 9
<212> TYPE: PRT
<213> ORGANISM: Homo sapiens

<400> SEQUENCE: 83

Phe Leu Ile Asp Ser Ser Glu Gly Val
1               5

<210> SEQ ID NO 84
<211> LENGTH: 9
<212> TYPE: PRT
<213> ORGANISM: Homo sapiens

<400> SEQUENCE: 84

Asn Leu Leu Asp Leu Asp Tyr Glu Leu
1               5

<210> SEQ ID NO 85
<211> LENGTH: 9
<212> TYPE: PRT
<213> ORGANISM: Homo sapiens

<400> SEQUENCE: 85

Thr Val Ala Glu Val Ile Gln Ser Val
1               5

<210> SEQ ID NO 86
<211> LENGTH: 11
<212> TYPE: PRT
<213> ORGANISM: Homo sapiens

<400> SEQUENCE: 86

Ser Leu Leu Ala Gln Asn Thr Ser Trp Leu Leu
1               5                   10

<210> SEQ ID NO 87
<211> LENGTH: 9
<212> TYPE: PRT
<213> ORGANISM: Homo sapiens

<400> SEQUENCE: 87

Leu Leu Leu Gly Ser Pro Ala Ala Ala
1               5

<210> SEQ ID NO 88
<211> LENGTH: 10
<212> TYPE: PRT
<213> ORGANISM: Homo sapiens

<400> SEQUENCE: 88

Glu Leu Ala Gly Ile Gly Ile Leu Thr Val
1               5                   10

<210> SEQ ID NO 89
<211> LENGTH: 9
<212> TYPE: PRT
<213> ORGANISM: Homo sapiens

<400> SEQUENCE: 89

Tyr Leu Leu Pro Ala Ile Val His Ile
1               5